United States Patent
Gravely et al.

(10) Patent No.: US 8,255,039 B2
(45) Date of Patent: *Aug. 28, 2012

(54) MEIBOMIAN GLAND ILLUMINATING AND IMAGING

(75) Inventors: Benjamin T. Gravely, Raleigh, NC (US); Stephen M. Grenon, Hillsborough, NC (US); Timothy R. Willis, Raleigh, NC (US); John M. Jans, Hillsborough, NC (US); Donald R. Korb, Boston, MA (US)

(73) Assignee: TearScience, Inc., Morrisville, NC (US)

( * ) Notice: Subject to any disclaimer, the term of this patent is extended or adjusted under 35 U.S.C. 154(b) by 1237 days.

This patent is subject to a terminal disclaimer.

(21) Appl. No.: 11/893,669

(22) Filed: Aug. 17, 2007

(65) Prior Publication Data
US 2008/0081999 A1    Apr. 3, 2008

Related U.S. Application Data

(63) Continuation-in-part of application No. 11/540,422, filed on Sep. 29, 2006.

(60) Provisional application No. 60/880,850, filed on Jan. 17, 2007.

(51) Int. Cl.
*A61B 6/00*    (2006.01)

(52) U.S. Cl. .............. 600/473; 600/407; 600/476; 607/1

(58) Field of Classification Search .................. 600/407, 600/476, 452, 427, 437, 473, 474; 607/1
See application file for complete search history.

(56) References Cited

U.S. PATENT DOCUMENTS

| | | |
|---|---|---|
| 3,909,771 A | 9/1975 | Pickering et al. |
| 4,261,364 A | 4/1981 | Haddad et al. |
| 4,274,421 A | 6/1981 | Dory |
| 4,567,898 A | 2/1986 | Plugge et al. |
| 4,584,880 A | 4/1986 | Matzuk |
| 5,137,355 A | 8/1992 | Barbour et al. |
| 5,557,351 A | 9/1996 | Kasahara et al. |
| 5,621,523 A | 4/1997 | Oobayashi et al. |
| 5,958,912 A | 9/1999 | Sullivan |
| 5,993,391 A | 11/1999 | Kamiyama |

(Continued)

FOREIGN PATENT DOCUMENTS
EP    2189108 A1    5/2010
(Continued)

OTHER PUBLICATIONS

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

(Continued)

*Primary Examiner* — Brian Casler
*Assistant Examiner* — Daniel Huntley
(74) *Attorney, Agent, or Firm* — Withrow & Terranova, PLLC

(57) ABSTRACT

In an illustrative embodiment, an apparatus for imaging a portion of a mammalian eyelid has an eye contact lenspiece configured to direct the light through an eyelid from posterior to anterior surface to thereby trans-illuminate the eyelid, when the light source illuminates the contact lens. An imaging device receives an image of the eyelid as it is trans-illuminated. Other methods and apparatus are presented in various embodiments, hence this abstract is not to be considered limiting, since other embodiments may deviate from the features described in this abstract.

51 Claims, 23 Drawing Sheets

U.S. PATENT DOCUMENTS

| | | | |
|---|---|---|---|
| 6,024,095 | A | 2/2000 | Stanley, III |
| 6,072,180 | A | 6/2000 | Kramer et al. |
| 6,107,289 | A | 8/2000 | Sullivan |
| 6,153,607 | A | 11/2000 | Pflugfelder et al. |
| 6,228,029 | B1 | 5/2001 | Eccardt et al. |
| 6,419,361 | B2 | 7/2002 | Cabib et al. |
| 6,455,583 | B1 | 9/2002 | Pflugfelder et al. |
| 6,500,123 | B1 | 12/2002 | Holloway et al. |
| 6,556,853 | B1 | 4/2003 | Cabib et al. |
| 6,949,071 | B1 | 9/2005 | Saied et al. |
| 7,060,061 | B2 | 6/2006 | Altshuler et al. |
| 7,111,980 | B2 | 9/2006 | Pavlidis et al. |
| 7,281,801 | B2 | 10/2007 | Wang |
| 2002/0180929 | A1 | 12/2002 | Tseng et al. |
| 2003/0018271 | A1 | 1/2003 | Kimble |
| 2003/0067249 | A1 | 4/2003 | Lockwood et al. |
| 2003/0069489 | A1* | 4/2003 | Abreu .................. 600/405 |
| 2003/0114426 | A1 | 6/2003 | Pflugfelder et al. |
| 2003/0195438 | A1 | 10/2003 | Petillo |
| 2003/0233135 | A1 | 12/2003 | Yee |
| 2004/0238969 | A1 | 12/2004 | Chen |
| 2005/0203421 | A1* | 9/2005 | Zeng et al. ............... 600/476 |
| 2006/0106283 | A1* | 5/2006 | Wallace et al. ........... 600/109 |
| 2006/0109423 | A1 | 5/2006 | Wang |
| 2006/0173360 | A1 | 8/2006 | Kalafut et al. |
| 2006/0187462 | A1 | 8/2006 | Srinivasan et al. |
| 2006/0223032 | A1* | 10/2006 | Fried et al. .............. 433/215 |
| 2011/0273550 | A1 | 11/2011 | Amano et al. |

FOREIGN PATENT DOCUMENTS

| | | | |
|---|---|---|---|
| JP | 2002515593 | A | 5/2002 |
| JP | 2004236727 | A | 8/2004 |
| JP | 2004536653 | A | 12/2004 |
| JP | 2006198249 | A | 8/2008 |
| JP | 2009134276 | | 6/2009 |
| WO | 99/58131 | | 11/1999 |
| WO | 9960331 | A1 | 11/1999 |
| WO | 03011135 | A1 | 2/2003 |
| WO | 2004/041134 | A1 | 5/2004 |

OTHER PUBLICATIONS

Mansour, Ahmad M., "Meibomian Gland Secretion" Orbit, vol. 7, Issue 3, Sep. 1988, 1 page.

Korb, Donald R. et al., "Increase in Tear Film Lipid Layer Thickness Following Treatment of Meibomian Gland Dysfunction" Lacrimal Gland, Tear Film and Dry Eye Syndromes: Basic Science Clinical Relevance. Adv. Exp. Med. Biol., vol. 350, 1994, 6 pages (pp. 293-298).

Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).

Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).

Matsuoka, Tooru et al., "Value of Meibography of the Upper Eyelid in Meibomian Gland Dysfunction" Congress of Clinical Ophthalmology, vol. 53, No. 3, Oct. 1998, 1 page.

Bucsko, J.K. "Imaging the Eye with Very-High-Frequency Ultrasound" Radiology Today, vol. 5, No. 19, p. 10, Sep. 13, 2004, http://www.radiologytoday.net/archive/rt_091304p10.shtml.

VanVelthoven, Mirjam Ej, et al., "Overlay of Conventional Angiographic and en-face OCT Images Enhances their Interpretation" BMC Ophthalmol. 2005: 5: 12. Published Online Jun. 13, 2005, 13 pages.

Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.

Arndt, G. Dickey et al., "Microwave Treatment of Prostate Cancer and Hyperplasia," NASA Tech Briefs, Jun. 2005, 1 page.

King-Smith, P. Ewen et al., "The Thickness of the Human Precorneal Tear Film: Evidence from Reflection Spectra," Investigative Ophthalmology & Visual Science, Oct. 2000, vol. 41, No. 11, 12 pages.

Knop, E. et al., "Meibomian Glands: Part III—Dysfunction—Argument for a Discrete Disease Entity and as an Important Cause of Dry Eye," Ophthalmologe, Vol. 106, No. 11, Nov. 2009, (Abstract Only).

Knop, E. et al., "Meibomian Glands: Part IV—Functional Interactions in the Pathogenesis of Meibormian Gland Dysfunction (MGD)," Ophthalmologe, vol. 106, No. 11, Nov. 2009, (Abstract Only).

Hrynchak, Patricia, Od, FAAO et al., "Optical Coherence Tomography: An Introduction to the Technique and its Use," Optometry and Vision Science, vol. 77, No. 7, Jul. 2000, pp. 347-356.

Korb, Donald R. et al., "Lid Wiper Epitheliopathy and Dry Eye Symptoms," Eye & Contact Lens, vol. 31, No. 1, 2005, pp. 2-8.

Alsuhaibani, Adel et al. "Utility of Meibography in the Evaluation of Meibomian Glands Morphology in Normal and Diseased Eyelids," Saudi Journal of Opthalmology, vol. 25, No. 1, Jan.-Mar. 2011, pp. 61-66.

Unknown, "ArcScan | Products," ArcScan, Inc., copyright 2007, accessed Jan. 9, 2008, http://www.arcscan.com/products.html, 5 pages.

Unknown, "VisualSonics—High Resolution Imaging," VisualSonics, accessed Jan. 9, 2008, http://www.visualsonics.com, 2 pages.

Unknown, "P45," Paradigm Medical Industries, Inc., Feb. 7, 2006, accessed Jan. 9, 2008, through the Internet Archive Wayback Machine, http://www.paradigm-medical.com/products/P45.htm, 2 pages.

Unknown, "OCT/SLO Technical Specifications," OTI Ophthalmic Technologies Inc., copyright 2003, accessed Jan. 9, 2008, through the Internet Archive Wayback Machine, http://www.oti-canada.com/octspecs.htm, 2 pages.

Unknown, "New Ophthalmic Products!," Quantel Medical, Feb. 21, 2006, accessed Jan. 9, 2008, through the Internet Archive Wayback Machine, http://www.quantelmedical.com/index.htm, 4 pages.

Unknown, "Stratus OCT—The Vision of Technology," Carl Zeiss Ophthalmic Systems, Inc., P/N. 54183, DOCT3 Rev A, May 2002, 6 pages.

Komuro, A. et al., "Examination of the Meibomian Gland," New Ophthalmology, vol. 18, No. 3, Mar. 31, 2001, pp. 301-306 (Japanese version and partial translation).

* cited by examiner

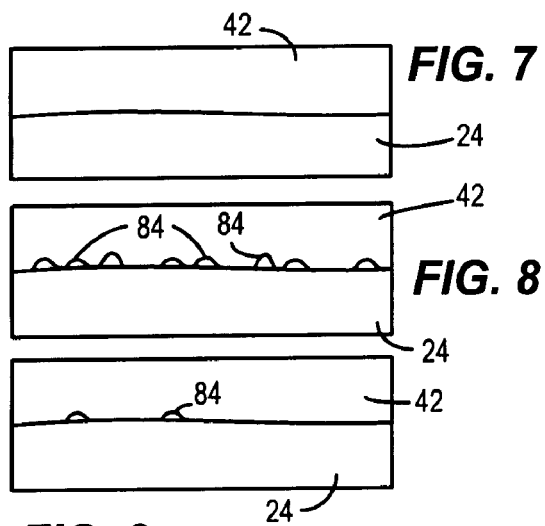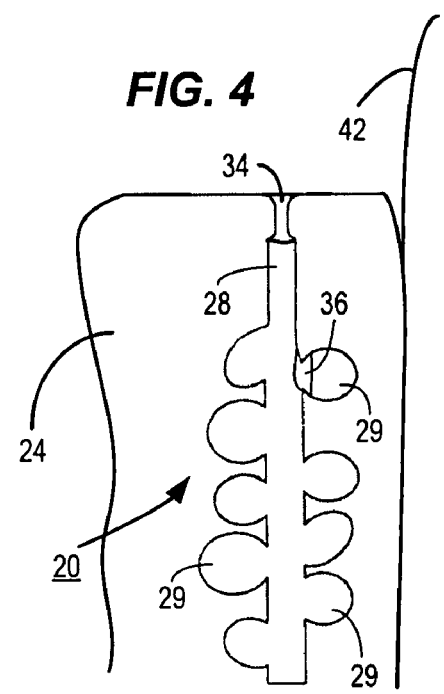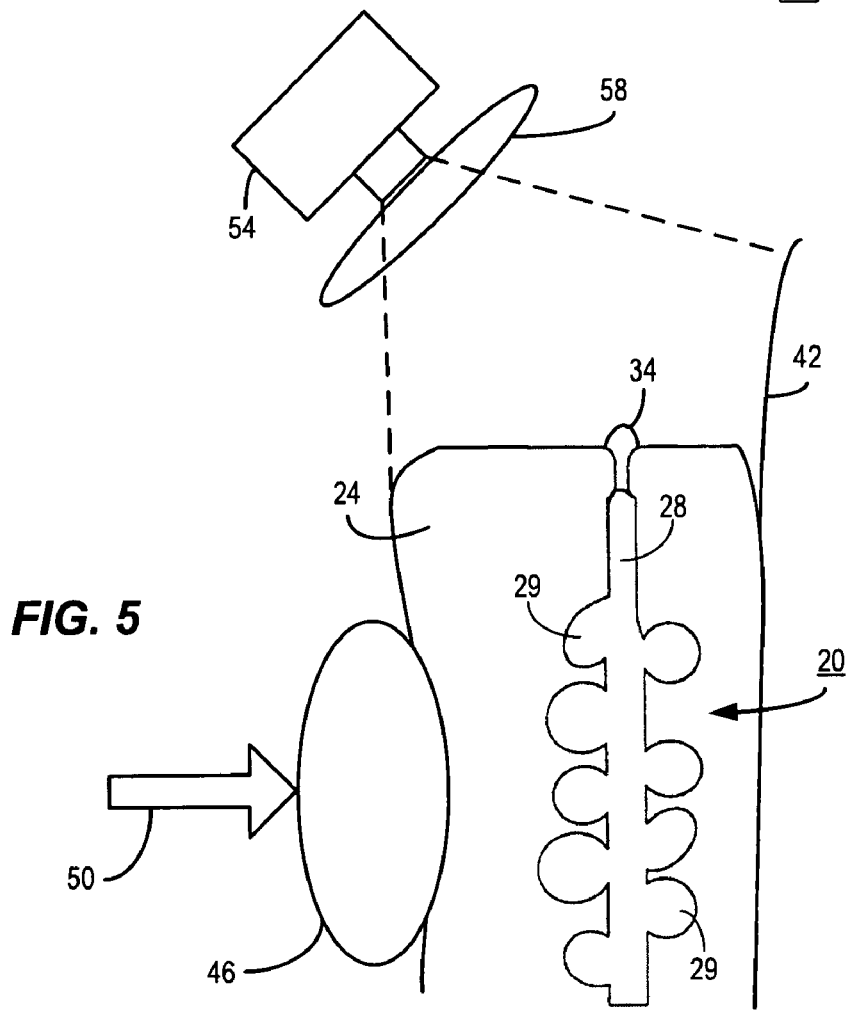

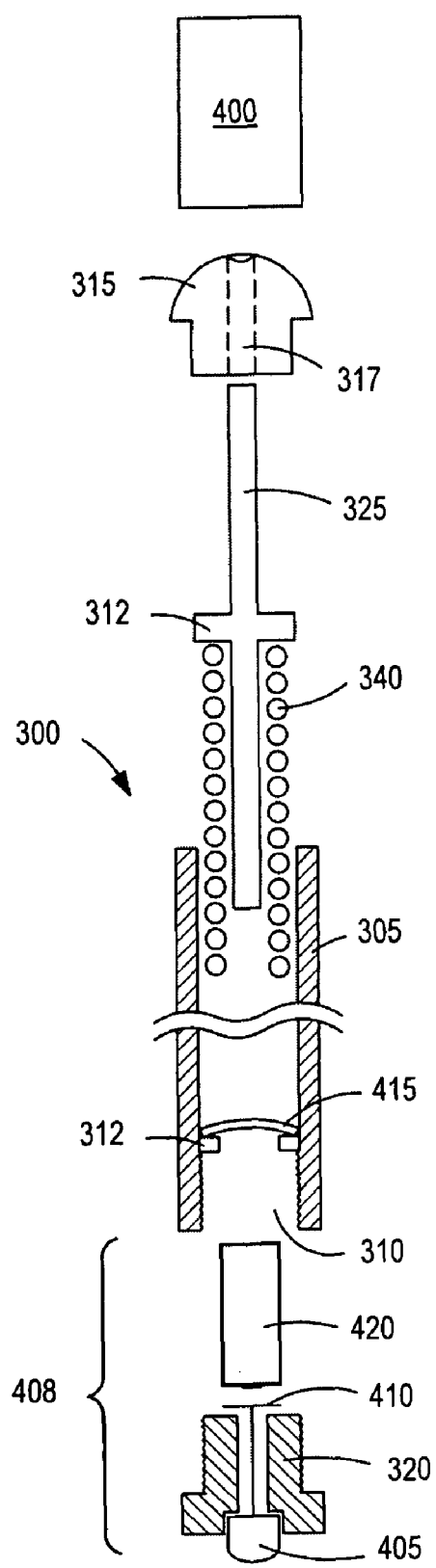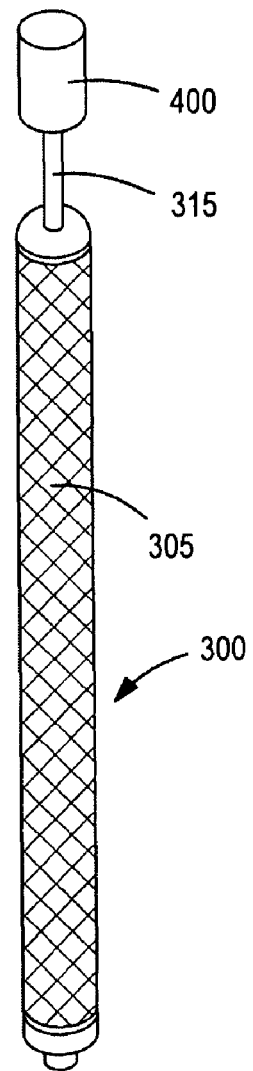
FIG. 16
FIG. 17

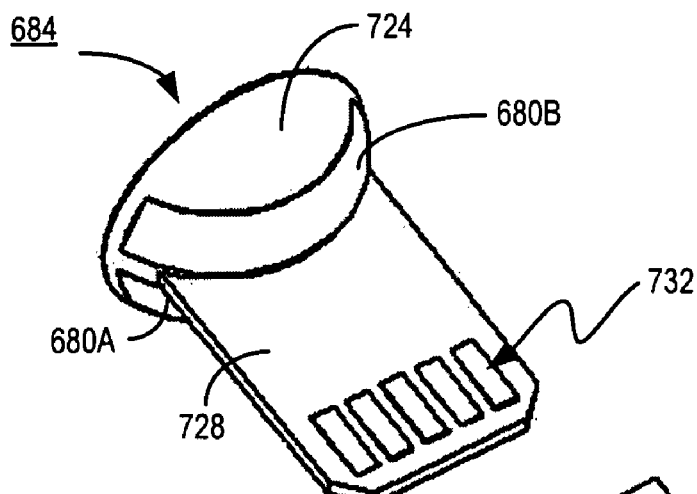
FIG. 32
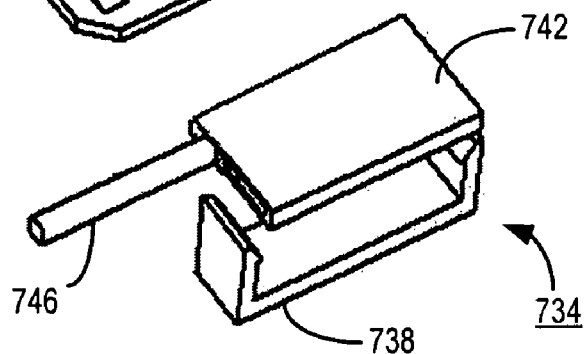
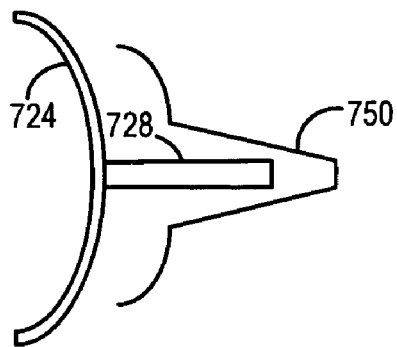
FIG. 34
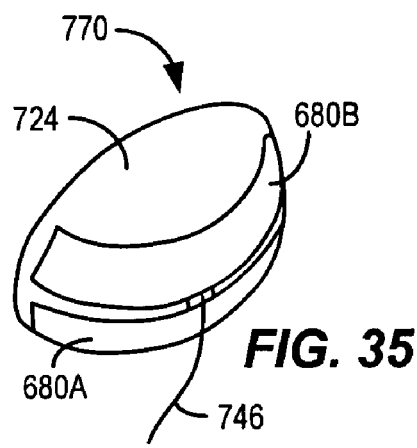
FIG. 35

MEIBOMIAN GLAND ILLUMINATING AND IMAGING

CROSS REFERENCE TO RELATED DOCUMENTS

This application is a continuation-in-part of and claims priority benefit of U.S. patent application Ser. No. 11/540,422 filed Sep. 29, 2006, and is further related to and claims priority benefit of U.S. Provisional Patent Application No. 60/880,850 filed Jan. 17, 2007, both of which are hereby incorporated by reference.

FIELD

This invention relates generally to the field of illuminating and imaging of eyelids of mammals. In particular, certain embodiments consistent with the invention relate to imaging of mammalian meibomian glands (also known as tarsal glands) or other structures or abnormalities of the eyelid including imaging of the meibomian glands to determine a degree of secretory function, dysfunction obstruction, full or partial obstruction, occlusion, dropout, diagnosis or effectiveness of treatment of such glands.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located on both the upper and lower eye lids, with orifices designed to discharge the lipid secretions onto the lid margins, thus forming the lipid layer of the tear film. The typical upper eyelid has about 25-30 meibomian glands and the lower eyelid has about 20-25 meibomian glands, which are somewhat larger than those located in the upper lid. The precise number varies with each individual. The meibomian gland is comprised of various sac-like acini which discharge the secretion into the main central duct of the gland. The secretion is then discharged through the orifice onto the lid margin. The duct is surrounded by smooth muscle tissue and the muscle of Riolan, whose contraction is presumed to aid in the expression of sebum. The meibomian gland orifices open onto the lid margin at and around the junction of the inner mucous membrane and the outer skin of the eyelids termed the mucocutaneous junction.

Specifically, each meibomian gland has a straight long central duct lined with four epithelial layers on the inner surface of the duct. At the opening of the duct, the four layers increase to six with these layers containing more keratin than the layers further from the gland orifice Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

Blinking causes the upper lid to pull a sheet of the lipids secreted by the meibomian glands over the other two layers of the tear film, thus forming a type of protective coating which limits the rate at which the underlying layers evaporate. When the lipid layer is pulled up by the blink, the aqueous layer may also be pulled up since the lipid layer utilizes a form of attachment to the aqueous layer with specialized interfacial molecules. When this occurs the lipid layer is readily visualized with interferometry, however, the movement of the aqueous layer, particularly regarding its correlation to then lipid layer cannot be observed. Thus, it will be seen that a defective lipid layer or an incorrect quantity of such lipids can result in accelerated evaporation of the aqueous layer which, in turn, causes symptoms such as itchiness, burning, irritation, and dryness, which symptoms suggest a condition or state of "dry eye".

Dry eye states have many etiologies. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infective state, or may be otherwise compromised so that the resulting lipid protective film of the tear layer is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combination of bacteria, sebaceous ground substance, dead, and/or desquamated epithelial cells, see, Korb et al., Meibomian Gland Dysfunction and Contact Lens Intolerance, Journal of the Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in obstructed meibomian glands ducts and orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, tear Film, ad Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

It is noted that partial obstruction in incipient stages may not lead to detectable dysfunction until obstruction crosses a threshold of detectable glandular efficacy—analogous to coronary occlusion from incipient to infarction.

It is further noted that the term "dropout" is used to refer to absence of one or more glands due to congenital, surgical or atrophic factors. Dropout is presently the word used to describe the partial or complete absence of the meibomian gland(s).

To summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice of the gland, in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication no. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover) to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in keratoconjuctivitis sicca as disclosed in U.S. Pat. No. 5,958,912 and U.S. Pat. No. 6,107,289 both titled "Ocular Therapy in Keratoconjunctivitis Sicca Using Topically Applied Androgens or TGF-β" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., Treatment of Non-Inflamed Obstructive Meibomian Gland dysfunction by an Infrared Warm Compression Device, British Journal of Opthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the cornea which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat. And furthermore, the device has no way of knowing how hot the tissue is getting. The temperature of the tissue and that of the meibomian glands being treated depends upon blood flow rate in the eyelid as well as eyelid thickness which are different from patient to patient.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in *Eye*, (2004) at pages 1-4. The problems associated with this invention are similar to those of the IR goggles in that no pressure or force is administered to the glands during heating.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

SUMMARY OF CERTAIN EMBODIMENTS

In view of the above, a need for an imaging technique for imaging the eyelid, and particularly the meibomian glands of the eyelids is needed. It is therefore an object of embodiments consistent with the present invention to provide an imaging method and apparatus for illuminating or imaging mammalian eyelids including meibomian glands.

It is a further object of certain embodiments to provide images of the meibomian glands.

It is another object of certain embodiments to provide illuminating and imaging techniques that produce images that can be stored and later retrieved or displayed.

It is still another object of embodiments consistent with the present invention to provide a method of illuminating or imaging meibomian glands that can be used to view or produce images that can be used to compare before and after treatment of the meibomian glands to determine a degree of effectiveness of treatment.

These and other objects and advantages will become evident upon review of the embodiments disclosed. It is noted that not all embodiments disclosed, taught or claimed herein necessarily meet each one of the objectives noted above, but that in no way should be construed to place the embodiment within or outside of the bounds of the inventions presented herein.

A method of near infrared (NIR) imaging of a meibomian gland consistent with certain illustrative embodiments involves illuminating the meibomian glands with NIR radiation using an NIR light source; focusing an NIR camera on a region of an eyelid containing the meibomian gland; making a first NIR image of the meibomian gland; applying a pressure suitable for simulating blinking pressure on the meibomian gland; optionally refocusing the NIR camera on the region of the eyelid containing the meibomian gland; and making a second NIR image of the meibomian gland while the pressure is being applied.

In certain embodiments, the NIR camera has an objective lens magnification of between about 60× and 10× between about 650 and 900 nm wavelength. As an example the range of 16× to 25× is the most common range used with a slit lamp for imaging one or several glands. However, it would also be desirable to image the entire lid to see the general characteristics of all of the meibomian glands. In certain embodiments, the imaging is carried out using NIR optical imaging approximately in the 0.650 to 2.5 micron wavelength range. In certain embodiments, the imaging is carried out using trans-illumination photography. In certain embodiments, the trans-illumination is produced by oblique illumination of the eyelid from an anterior surface thereof. In certain embodiments, the trans-illumination is produced by lighting the eyelid from a posterior surface thereof. In certain embodiments, the trans-illumination is produced by use of a scleral lens serving as a light source from the posterior surface of the eyelid. In certain embodiments, the trans-illuminating is carried out using a lenspiece comprises an array of light emitting elements mounted to a substrate suitable for contact with eyeball. In certain embodiments, the NIR radiation includes radiation having wavelength that is either absorbed or transmitted preferentially through lipid rich material versus tissue surrounding lipid rich tissue. In certain embodiments, at least one of the imaging and re-imaging is carried out while pressure is applied to the eyelid that simulates an amount of pressure caused by blinking the eyelid.

In another illustrative embodiment, a method of imaging a mammalian meibomian gland or other section of an eyelid involves shining a near infrared light on the eyelid in order to trans-illuminate at least a portion of the eyelid with NIR illumination; and from the outer surface of the eyelid, imaging the trans-illuminated portion of the eyelid using NIR microscopic imaging.

In certain embodiments, the shining and capturing are repeated at an adjacent location of the outer surface of the eyelid and further comprising combining the images from the first and adjacent locations. In certain embodiments, the combining is selected from the group consisting of stitching, adding, and averaging the images from the first and adjacent locations to produce a resultant image of a larger area of the eyelid. In certain embodiments, the NIR microscopy imaging is carried out using a camera having an objective lens magnification of between about 60× and 10× between about 650 and 900 nm wavelength. In certain embodiments, the imaging is carried out using NIR optical imaging in approximately the 0.650 to 2.5 micron wavelength. In certain embodiments, the trans-illumination is produced by lighting the eyelid from a posterior surface thereof. In certain embodiments, the transillumination is produced by use of a scleral lens serving as a light source from the posterior surface of the eyelid. In certain embodiments, the trans-illumination is produced by use of a contact lenspiece comprising an array of light emitting elements mounted to a substrate suitable for contact with eyeball. In certain embodiments, the NIR radiation includes radiation having wavelength that is either absorbed or transmitted preferentially through lipid rich material versus tissue surrounding lipid rich tissue.

In another illustrative embodiment, a method of imaging a mammalian patient's meibomian gland or other section of an eyelid of an eye involves placing a contact light source in contact with the eye; having the patient close the eye; illuminating the contact light source light emitting from the light source through the eyelid from the posterior surface of the eyelid to trans-illuminate a portion of the eyelid; and from the outer surface of the eyelid, imaging the trans-illuminated portion of the eyelid.

In certain embodiments, the process further involves repeating the illumination and capturing of an image at a second location on the eyelid, and processing the images to produce a single composite image. In certain embodiments, the contact light source produces NIR light and wherein imaging is carried out using a NIR camera having an objective lens magnification of between about 60× and 10× between about 650 and 900 nm wavelength. In certain embodiments, the imaging is carried out using NIR optical imaging in approximately the 0.650 to 2.5 micron wavelength. In certain embodiments, the trans-illumination is produced by lighting the eyelid from a posterior surface thereof. In certain embodiments, the trans-illumination is produced by use of a scleral lens serving as a light source from the posterior surface of the eyelid. In certain embodiments, the trans-illumination is produced by a contact lenspiece that comprises an array of light emitting elements mounted to a substrate suitable for contact with eyeball. In certain embodiments, the NIR radiation includes radiation having wavelength that is either absorbed or transmitted preferentially through lipid rich material versus tissue surrounding lipid rich tissue.

In another illustrative embodiment, an apparatus for imaging a portion of a mammalian eyelid has a light source suitable for directing near infrared light to a portion of the eyelid to illuminate a portion of the eyelid. A microscopic optical receiver suitable for receiving light from the eyelid and producing an output signal depicting an NIR image of the eyelid, the microscopic optical receiver receives light from the outer surface of the eyelid. An image processor receives the output signal that captures an image from the light receiver.

In certain embodiments, the light source is arranged to provide oblique illumination in order to trans-illuminate the portion of the eyelid. In certain embodiments, the light source directs light to the portion of the outer surface of the eyelid via a first optical fiber. In certain embodiments, the optical receiver receives light from the outer surface of the eyelid via a second optical fiber. In certain embodiments, the trans-illumination is produced by lighting the eyelid from a posterior surface thereof. In certain embodiments, the light source comprises a scleral lens serving as a light source from the posterior surface of the eyelid. In certain embodiments, the light source produces light having wavelength that is either absorbed or transmitted preferentially through lipid rich material versus tissue surrounding lipid rich tissue. In certain embodiments, the light source comprises a lenspiece having an array of light emitting elements mounted to a substrate suitable for contact with eyeball. In certain embodiments, the light source directs light to the portion of the outer surface of the eyelid via a first optical fiber, and wherein the optical receiver receives light from the outer surface of the eyelid via a second optical fiber, and wherein the first and second optical fibers are positioned in a fixed geometric relationship with one another.

In another illustrative embodiment, an apparatus for imaging a portion of a mammalian eyelid has an eye contact lenspiece configured to direct the light through an eyelid from posterior to anterior surface to thereby trans-illuminate the eyelid, when the light source illuminates the contact lens. An imaging device receives an image of the eyelid as it is trans-illuminated.

In certain embodiments, an image processor, receiving an output signal from the camera and processes the output signal to enhance the image. In certain embodiments, the light source comprises an infrared light source and wherein the imaging device is compatible with infrared light. In certain embodiments, the light source comprises a visible light source and wherein the imaging device is compatible with visible light. In certain embodiments, the trans-illumination is produced by lighting the eyelid from a posterior surface thereof. In certain embodiments, the light source comprises a scleral lens serving as a light source from the posterior surface of the eyelid. In certain embodiments, the light source produces light having wavelength that is either absorbed or transmitted preferentially through lipid rich material versus tissue surrounding lipid rich tissue. In certain embodiments, the light source comprises a lenspiece having an array of light emitting elements mounted to a substrate suitable for contact with eyeball.

in another exemplary embodiment, an apparatus for imaging a portion of a mammalian eyelid has a light source configured to direct near infrared light through an eyelid to thereby trans-illuminate the eyelid. A NIR microscopic camera records an image of the eyelid as it is trans-illuminated. The light source is automatically positioned at a plurality of locations adjacent the eyelid and records a plurality of images at each of the plurality of locations using the camera. A processor averages the plurality of images to produce a resultant image.

In certain embodiments, the NIR microscopic camera has an objective lens magnification of between about 60× and 10× between about 650 and 900 nm wavelength. In certain embodiments, the imaging is carried out using NIR optical imaging in approximately the 0.650 to 2.5 micron wavelength. In certain embodiments, the trans-illumination is produced by lighting the eyelid from a posterior surface thereof. In certain embodiments, the light source comprises a scleral lens serving as a light source from the posterior surface of the eyelid. In certain embodiments, the light source comprises a lenspiece having an array of light emitting elements mounted to a substrate suitable for contact with eyeball. In certain embodiments, the light source produces light having wavelength that is either absorbed or transmitted preferentially through lipid rich material versus tissue surrounding lipid rich tissue.

In another exemplary embodiment, an apparatus for facilitating trans-illumination of an eyelid covering an eye has an eye shield having curvature that is configured to approximately match a portion of a curvature of the external surface sclera of the eye, the eye shield having an inner surface that contacts the eye and an outer surface. The eye shield has properties that render the eye shield opaque to light of a particular spectrum. An array of light sources is disposed on the outer surface to produce light in the particular spectrum in order to trans-illuminate the eyelid from a posterior side of the eyelid.

In certain embodiments, the array of light sources comprises an array of light emitting diodes (LEDs). In certain embodiments, the LEDs comprise surface mount LEDs. In certain embodiments, a flexible circuit board is affixed to the outer surface and wherein the LEDs in the array of LEDs are attached to the flexible circuit board. In certain embodiments, an outer mold covers the array of LEDs in a manner that produces a smooth surface. In certain embodiments, the flexible circuit board is reflective of light of the specified spectrum. In certain embodiments, an outer mold covers the array of light sources in a manner that produces a smooth surface. In certain embodiments, the outer mold has light filtering or diffusing properties. In certain embodiments, the outer mold is transparent to the light of the particular spectrum. In certain embodiments, an electrical connector provides electrical current to the array of light sources. In certain embodiments, means are provided for supplying electrical current to the array of light sources. In certain embodiments, the outer surface is reflective of light of the specified spectrum.

In another exemplary embodiment, an apparatus for facilitating trans-illumination of an eyelid covering an eye has an eye shield having curvature that is configured to approximately match a portion of a curvature of the external surface sclera of the eye, the eye shield having an inner surface that contacts the eye and an outer surface. The eye shield has properties that render the eye shield opaque to light of a particular spectrum. A flexible circuit board is affixed to the outer surface. An array of surface mount light emitting diodes is disposed on the flexible circuit board to produce light in the particular spectrum in order to trans-illuminate the eyelid from a posterior side of the eyelid. An outer mold covers the array of LEDs in a manner that produces a smooth surface. Electrical current is supplied to the array of LEDs.

In certain embodiments, the flexible circuit board is reflective of light of the specified spectrum. In certain embodiments, the outer mold has light filtering or diffusing properties. In certain embodiments, the outer mold is transparent to the light of the particular spectrum. In certain embodiments, the outer surface is reflective of light of the specified spectrum.

In another exemplary embodiment, an apparatus for facilitating trans-illumination of an eyelid covering an eye has an elongated handle having an end. An eye shield is affixed to the end of the handle, the eye shield having opposing lighting and shielding surfaces. The eye shield has properties that render the eye shield opaque to light of a particular spectrum. An array of light sources is disposed on the lighting surface to produce light in the particular spectrum in order to trans-illuminate the eyelid from a posterior side of the eyelid when the eye shield is placed between the eyelid and the eye, and simultaneously shield the eye from direct light emanating from the light sources. The eye shield and the array of light sources are flat enough to fit between the eyelid and the eye.

In certain embodiments, the array of light sources comprises an array of light emitting diodes. In certain embodiments, the LEDs comprise surface mount LEDs. In certain embodiments, a flexible circuit board is affixed to the lighting surface and wherein the LEDs in the array of LEDs are attached to the flexible circuit board. In certain embodiments, an outer mold covers the array of LEDs in a manner that produces a smooth surface. In certain embodiments, the flexible circuit board is reflective of light of the specified spectrum. In certain embodiments, an outer mold covers the array of light sources in a manner that produces a smooth surface. In certain embodiments, the outer mold has light filtering or diffusing properties. In certain embodiments, the outer mold is transparent to the light of the particular spectrum. In certain embodiments, the handle includes a source of electrical current that supplies electrical current to the array of light sources. In certain embodiments, electrical current is supplied to the array of light sources.

The above overviews are intended to illustrate some of the many exemplary embodiments which will be best understood in conjunction with the detailed description to follow, and are not intended to limit the scope or meaning of the appended claims.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which:

FIG. 4 is another cutaway view of meibomian gland 20 illustrating approximate positioning of the eyelid and the eyeball.

FIG. 5 is another cutaway view of meibomian gland 20 having a bulging plug in its orifice when pressure is applied that is imaged in a manner consistent with certain embodiments of the present invention.

FIG. 7 is a two dimensional depiction of an image of an eyelid having plugged meibomian glands prior to application of a pressure suitable for causing physical deformities at or about the orifice of the meibomian gland in a manner consistent with certain embodiments of the present invention.

FIG. 8 is a two dimensional depiction of an image of an eyelid with plugged meibomian glands with a pressure applied to cause physical deformities at or about the orifice in manner consistent with certain embodiments of the present invention.

FIG. 9 is a two dimensional depiction of an image of the eyelid of FIG. 8 after treatment to unplug the meibomian glands with pressure again applied to cause any remaining orifice obstructions to become observable in a manner consistent with certain embodiments of the present invention.

FIG. 16 a broken away side view of an embodiment of the meibomian gland evaluation tool according to the present invention.

FIG. 17 is another view of an embodiment of the meibomian gland evaluation tool according to the present invention.

FIG. 32 illustrates a light array assembly consistent with certain embodiments of the present invention.

FIG. 34 is a cross-sectional view showing assembly of the flex circuit on the lenspiece and connector in a manner consistent with certain embodiments of the present invention.

FIG. 35 is an illustration of another embodiment of an eyepiece and light array assembly consistent with the present invention.

DETAILED DESCRIPTION

Figure 1:
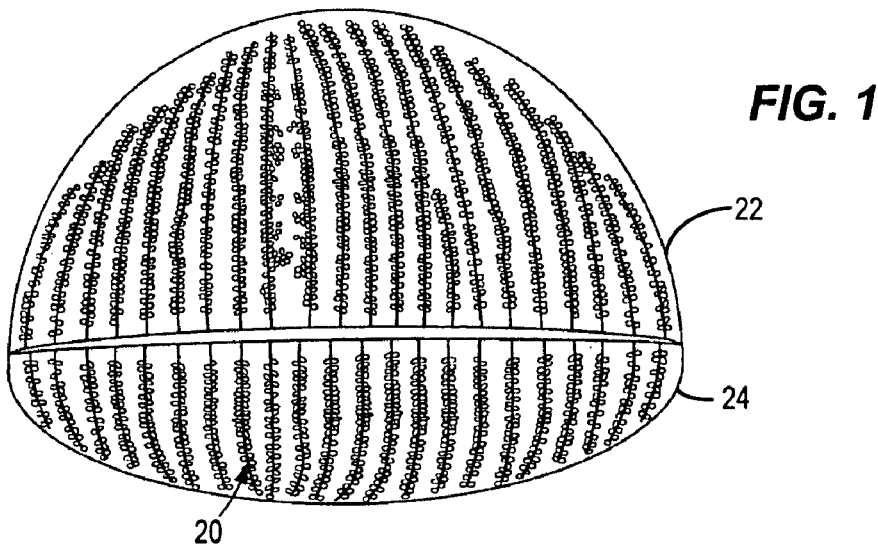
FIG. 1 depicts upper and lower human eyelids showing the meibomian glands.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The term "program" or "computer program" or similar terms, as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system, and may be stored in a form of software or firmware.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

As noted above, dry eye states have many etiologies. A common cause of common dry eye states is the condition known as "meibomian gland dysfunction", a disorder where the glands are obstructed or occluded. As employed herein the terms "occluded" and "obstruction" as they relate to meibomian gland dysfunction are defined as partially or completely blocked or plugged meibomian glands having a solid, semi-solid or thickened congealed secretion and/or plug of any composition, leading to a compromise, or more specifically, a decrease or cessation of secretion. Also with a reduced or limited secretion the meibomian gland may be compromised by the occluded or obstructive condition as evidenced by a yellowish color indicating a possible infective state, or may be otherwise compromised so that the resulting protective lipid film of the tear film layer is not adequate.

Imaging of the meibomian glands of the human eyelid as well as imaging while simultaneously applying pressure to mimic the normal expression of secretion from the meibomian glands by blinking enables study of the dynamic function of the meibomian glands and resulting pathology. The imaging of the meibomian glands while simultaneously applying pressure permits the viewing of the anatomical features of the gland with and without pressure and the observation of the effects of the pressure on the movement of the secretory material within and out of the gland. The latter observations permit the diagnosis of gland dysfunction and obstruction and the specific diagnosis of the site of the pathology within the gland or over the gland orifice.

As noted earlier, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells manufacture the secretions of the meibomian gland. The secretions flow from each acinus to the duct. While currently it has not been established with certainty, there appears to be a valve system between each acinus and the central duct to retain the secretion until it is required, at which time it is discharged in to the central duct. The meibomian secretion is then stored in the central duct and is released through an orifice of each gland onto the surface of the eyelid at the eyelid margin. The central duct leading to the orifice is on the order of 100 microns or less in diameter. Blinking and the squeezing action of the muscle of Riolan surrounding the meibomian glands are currently believed to be the primary mechanism to open the orifice for the release of secretion from the meibomian gland.

There is currently no truly acceptable method of imaging the meibomian gland and related structures or other abnormalities of the eyelid in order to evaluate the function of the glands. Moreover, there is currently no truly acceptable mechanism to evaluate the dynamic function and resulting pathology of the meibomian gland.

In order to better understand the dynamic function and resulting pathology of the meibomian glands, certain embodiments consistent with the present invention utilize the application of varying levels of pressure to the glands in order to observe the gland when a pressure comparable to that exerted by the blink is applied over the meibomian glands. The pressures of the lids during normal blinking are minimal—perhaps on the order of only several grams per square mm of pressure. Many individuals with dry eye conditions practice forced blinking where the lids are squeezed together tightly with maximum pressure as an aid in expression of the meibomian secretion which are not adequately expressed with normal blinking due to partial meibomian gland obstruction. It should also be noted that there may be a wide variance in the efficacy of the approximately 50 meibomian glands of both eyelids, where some glands will be totally obstructed, some partially obstructed with minimal secretion, and some with varying degrees of normal secretion.

The application of a pressure of varying degrees to the external surface of the eyelids while simultaneously imaging the meibomian glands allows the visualization of the dynamic status of the gland relative to the following:

Whether the secretory material with the application of a pressure to the external lid flows from the acini to the central duct or the secretory material is trapped and stagnated within the acini. One cause for this is an obstruction in valves that may be present in the acini at their junction to the central duct.—According to literature Mansour (1988) along with Virchow (1910) and Dryja (1986) published on valves in the Meibomian gland. Mansour described the valves and postulated that if the valves malfunctioned, chalazia might occur. (Mansour A M (1988). Meibomian Gland Secretion. Orbit—An International Journal On Orbital Disorders And Facial Reconstructive Surgery 7 (3): 201-209.)

Chalazion is usually thought of a swelling, engorgement or increase in size of a meibomian gland and pertinent descriptions and definitions follow: Patients will generally present with one or many focal, hard, painless nodules in the upper or lower eyelid. They may report some enlargement over time, and there may be a history of a painful lid infection prior to the chalazion development, but this isn't always the case. A chalazion is a non-infectious, granulomatous inflammation of the meibomian glands. The nodule itself consists of many types of steroid-responsive immune cells, including connective tissue macrophages known as histiocytes, multinucleate giant cells, plasma cells, polymorphonuclear leukocytes and eosinophils. A chalazion may be a residual aggregation of inflammatory cells following an eyelid infection such as hordeola and preseptal cellulitis, or may develop from the retention of meibomian gland secretions.

Heretofore, this observation and diagnosis has never been reported. It may also be possible to observe the anatomical features which regulate flow from the acini into the central duct and their actions observed under application of varying pressures leading to a diagnosis that will facilitate treatment methods.

The central duct should be open without obstruction or adhesions and contain the liquid contents of the secretions from the acini. Imaging and observation will identity the nature and the location of any obstruction or adhesion. The diagnosis of the status of the central duct has never been reported (other than with biopsy specimens). Imaging of the central duct will facilitate development and utilization of treatment methods.

The central duct should discharge the secretory contents through the orifice onto the lid margin and to the tear film with the application of a pressure to the external lid mimicking the pressures of a blink. The discharge occurs through the orifices of the meibomian glands, which are situated in the lid margin and are closed unless a pressure is applied either through blinking or by manual means. Imaging of the gland simultaneously with the application of pressure will reveal the flow characteristics within the gland and the nature of the flow through the central duct and the terminal duct ending at the orifice.

If the application of a pressure to the external lid does not result in the expression of secretion from the gland, appropriate imaging will reveal whether the application of the pressure results in a pouting, bulging or a change in shape of the orifice. When the secretory material is compressed into the orifice, if there is overgrowth of tissue over the gland orifice, there will be pouting or other physical deformation of the contents at the end of the orifice, the pouting resulting from the overgrowth of epithelium over the gland which will extend with the pressure from the compression of the contents. This indicates that the primary obstructive process is not primarily within the duct, but is the result of obstruction of the duct by the overgrowth of epithelium of the lid margin over the duct. Secondary obstruction within the duct will then occur, since the secretions are unable to be discharged due to the obstruction over the orifice on the lid margin. Specific treatment to relieve the overgrowth is therefore indicated. If on the other hand there is no pouting of the gland or other physical deformation at the orifice surface, the obstruction would more likely be internal, and the location of such obstruction would advantageously be shown by certain of the imaging techniques consistent with certain embodiments of the present invention (or could at least be deduced by a lack of observable pouting or other deformities of the orifice). Treatment could then therefore be directed to the internal cause.

Application of pressure also may result in secretion of materials whose color, consistency and other characteristics can facilitate diagnosis.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland and compromise the secretory functions of the individual meibomian glands. More particularly, these keratotic obstructions can comprise combination of bacteria, sebaceous ground substance, dead, and/or desquamated epithelial cells. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction may be limited to subtle alterations of the meibomian gland orifices, overgrowth of epithelium over the orifices, and pouting of the orifices of the glands with congealed material acting as obstructions, for example.

In view of the difficulty of diagnosis of the function of the meibomian glands by the usual slit-lamp visual inspection utilizing magnification, and the lack of existing criteria for evaluation of the degree of dysfunction of the meibomian glands, the inventors have determined that there is a need for imaging techniques that can be employed in the diagnostic processes. While imaging of various portions of the human anatomy have been studied and developed extensively, techniques for suitable imaging the meibomian glands of a living subject, other than the slit-lamp magnified visual examination, are non-existent. Illuminating and imaging of the meibomian glands present unusual and specific problems.

Several different mechanisms can be provided for imaging the eyelid to provide imaging to assist in diagnostic as well as pre and post treatment evaluation of the proper function of the meibomian glands of the eyelid. While the human eye is of greatest interest, the techniques described herein may also be applied to other mammalian eyelids as well as other similar glands, with human eyes being referenced by way of example herein.

The typical human eyelid is less than 5 mm in thickness, and is most often less than about 4 mm in thickness. An eyelid that is 5 mm or more in thickness constitutes a quite thick eyelid for a human subject. The upper eyelid contains approximately 25-30 meibomian glands while the lower eyelid contains approximately 20-25 meibomian glands. In most instances, the meibomian glands are situated within the eyelid approximately ⅔ of the way from the front to the rear of the eyelid. The central tube of a small sample of glands that have been measured are roughly 100 microns in diameter (with a great deal of variation anticipated since only a limited number of glands have actually been measured at this writing). Also to identify a full or partial meibomian gland obstruction, either fully or partially, the imaging should preferably have a resolution down to approximately 1 to 10 microns with 1 to 5 being desired. This presents a rather unusual imaging problem in that the gland is quite small, is situated on a curved surface, is located at a very sensitive part of the body and requires rather high resolution imaging to actually observe. Hence, one or more techniques that can be used with relative comfort to the patient and which result in resolution that is high enough to be of value to the clinician are needed. Imaging these glands is further complicated by the relatively small size of the glands and lack of clear reference points to identify one particular gland and distinguish it from other glands. Currently, no numbering or other identification system to isolate a single gland exists, partially due to the variation in number of such glands, and difficulty in establishing standards in the absence of satisfactory imaging.

As noted, these glands can become obstructed or clogged to produce varying degrees of "dry eye syndrome". Normally, the meibomian glands produce clear oil which, together with tears, serves to keep the eye lubricated and cleansed. However, meibomian glands can become clogged for a variety of reasons (many even potentially unknown). In such circumstances, the secretion of natural oils is inhibited or stopped altogether. The obstructive materials or plugs that occlude the glands when examined after their expression from the gland take on various physical appearances including, but not limited to, clear gel, a petroleum jelly like appearance, milky colored or hard white wire-like appearance. Also the physical appearance is dependent upon temperature and can be oil; inspissated jelly like; globular or bead like; filamentary from thin wire like to thicker filaments resembling tooth paste expressed from the tube. The color can be clear, tinged off white varying to yellow indicating infection and pus. Each such obstruction, whether total or partial, reduces the amount of oil available to lubricate the eye, leading to increased evaporation of the tear film, and inflammation and/or discomfort and dry eye states when the number of compromised meibomian glands fails to provide an adequate lipid layer to maintain the tear film.

In most instances the lower eyelids are of most interest since they appear to generally be a primary source of secretion of the natural oils, and are most frequently the culprit when a patient presents with dry eye syndrome related to occluded meibomian glands. The upper eyelids tend to be less problematic—perhaps due to their movement during blinking or gravity assisting in the flow of lipids therefrom.

Current diagnosis techniques are limited to microscopic visual inspection of the top of the glands at the lid margin, or trans-illumination by inverting the eyelid and viewing the eyelid from the inner surface (which has been inverted for viewing—which presents difficulty for the physician in manipulation of the eyelid and patient discomfort). There is no known technique that can provide imaging that can provide before and after images in order to assess the success of any given treatment. The lack of a consistent diagnosis tool to obtain before and after comparison images of the operation of the glands and treatment success further leads to problems in insurance reimbursement for the physician.

Several variations of visualization of the meibomian glands are presented herein. It will be understood that many variations of the embodiments taught will be evident to those skilled in the art upon consideration of the present teachings. Each of the technologies described herein can be implemented using either stationary apparatus into which the patient places his or her eye during imaging (e.g., with stabilization of the patient's head by chin and forehead rests), and handheld apparatus which is placed in appropriate proximity to the eyelid by the physician or technician during testing.

Figure 2:
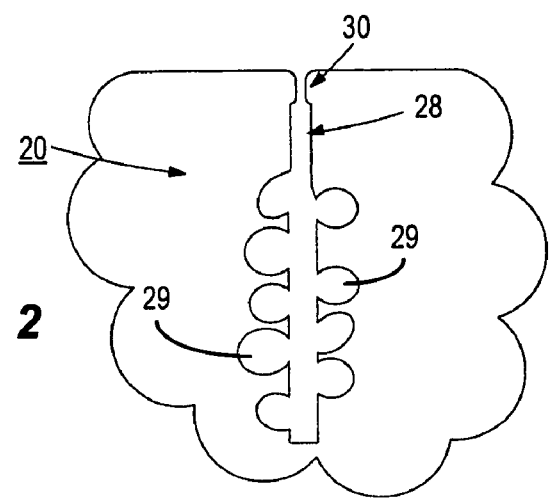
FIG. 2 is a cutaway view of an illustrative meibomian gland 20.

Referring now to FIG. 1, the location of the meibomian glands 20 are shown on the upper and lower eyelids 22 and 24 respectively. As briefly stated herein above, the upper lid contains about 25 meibomian glands and the lower lid contains about 20 meibomian glands, with significant variation. As shown in cross-sectional view of one gland 20 in FIG. 2, each gland includes a central duct or channel 28 into which the secretion flows from acini 29 and an orifice 30 which opens on to the eyelid margin and through which the secretion flows in order to be added to the tear film upon blinking. It will be seen that the glands are of different size, depending upon the location in the eyelid and that the orifice 30 is narrower than the central duct 28.

Figure 3:
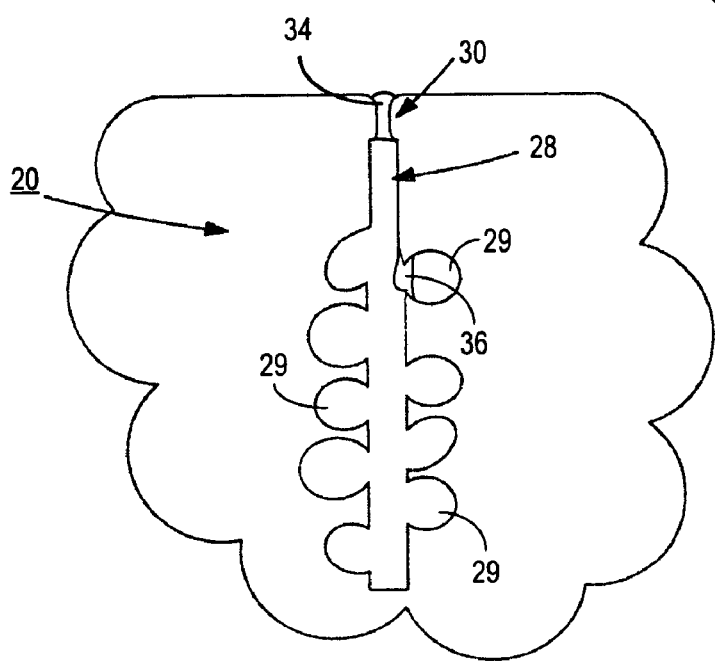
FIG. 3 is a cutaway view of meibomian gland 20 illustrating a plugged orifice.

Obstruction composition will vary with the etiology which produced it. However, the obstruction will, in most cases observed to the present, be a combination of, dead cells, bacteria, desquamated cells, desquamated cells aggregating in keratotic clusters, milky fluid, inspissated or creamy secretions, or any combination of the foregoing in solid, semi-solid and thickened forms. Referring to FIG. 3, a simplified view of exemplary obstructions to gland 20 is depicted. In this example, which is by no means necessarily representative of all meibomian gland obstructions, as explained above, a solid or semi-solid or thickened plug 34 is depicted which is fully occluding the orifice 30 of gland 20. Another obstruction 36 is shown at a junction from one of the acini with the central duct. As previously noted, this may be the site of a valve in the gland structure, but embodiments consistent with the present invention should not be limited by theories of the actual meibomian gland structure.

Surface Imaging

One mechanism for providing imaging of meibomian glands for both diagnosis and post treatment evaluation is depicted in FIGS. 4-9. FIG. 4 depicts a cutaway view of meibomian gland 20 illustrating approximate positioning of the lower eyelid 24 and the eyeball 42. Details such as the eyelashes have been omitted for illustrative clarity. In some instances, microscopic observation can detect the presence of a plug 34 in meibomian gland 20, or adjacent meibomian glands. However, in many instances, simple visual observation is inadequate to clearly document and specifically identify the location or locations of an occluded meibomian gland 20, particularly depending upon the nature of the plug 34. It is also noted that magnification levels of 25× to 50× at least are advantageous in observation of the orifice at the surface of a meibomian gland. However, such high magnification is difficult to use due to the great exaggeration of even very small movements of the patient.

However, plugged glands such as gland 20 can be more readily identified using the technique illustrated in FIG. 5, which depicts another cutaway view of meibomian gland 20 having a bulging plug 34 or puckering or other physical deformation at the orifice 30 in its orifice that is imaged in a manner consistent with certain embodiments of the present invention. In this embodiment, a tool 46 (which may simply be a finger, but is preferably a calibrated instrument as will be described later) is pressed against lower eyelid 24 in a controlled manner, while the upper eyelid is held open, with the pressure illustrated by arrow 50. This pressure compresses the eyelid from the anterior surface, and thus the meibomian gland 20 so that fluid present inside the gland 20, exerts upward pressure on the plug 34 to produce a bulge, pucker or other physical deformation at the surface of the eyelid at or about the location of the orifice as illustrated. This technique provides the physician with an indication of the actual functioning of the glands.

Images can be made using a camera 54 with suitable magnification (depicted as 58), e.g., attached to an ophthalmologic microscope or macro focus lens of suitable focal length, lighting and magnification to image a desired region of the eyelid and freeze or minimize the effects of patient movement. Flash photography or high light—high shutter speed photography can be used to freeze motion if needed. In other embodiments, pressure can be exerted from either or both the anterior and posterior surfaces of the eyelid to thereby squeeze the meibomian glands. The application of pressure on the eyelid and imaging of the secretion is also useful in diagnosis. Depending on the color, consistency and presence of the secretion one can categorize the amount of meibomian gland dysfunction (MGD). The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained. As noted above, obstruction composition will vary with the etiology which produced it. However, the obstruction will, in most cases observed to the present, be a combination of, dead cells, bacteria, desquamated cells, desquamated cells aggregating in keratotic clusters, milky fluid, inspissated or creamy secretions, or any combination of the foregoing in solid, semi-solid and thickened forms.

A similar procedure can be carried out for imaging the upper eyelid, however it is believed at present that approximately 70% of dry eye problems are associated with meibomian gland dysfunction with the lower eyelid. Accordingly, diagnosis and treatment of the lower eyelid may be of most significance in many cases. However, this is not intended to preclude imaging of the upper or both eyelids.

Figure 6:
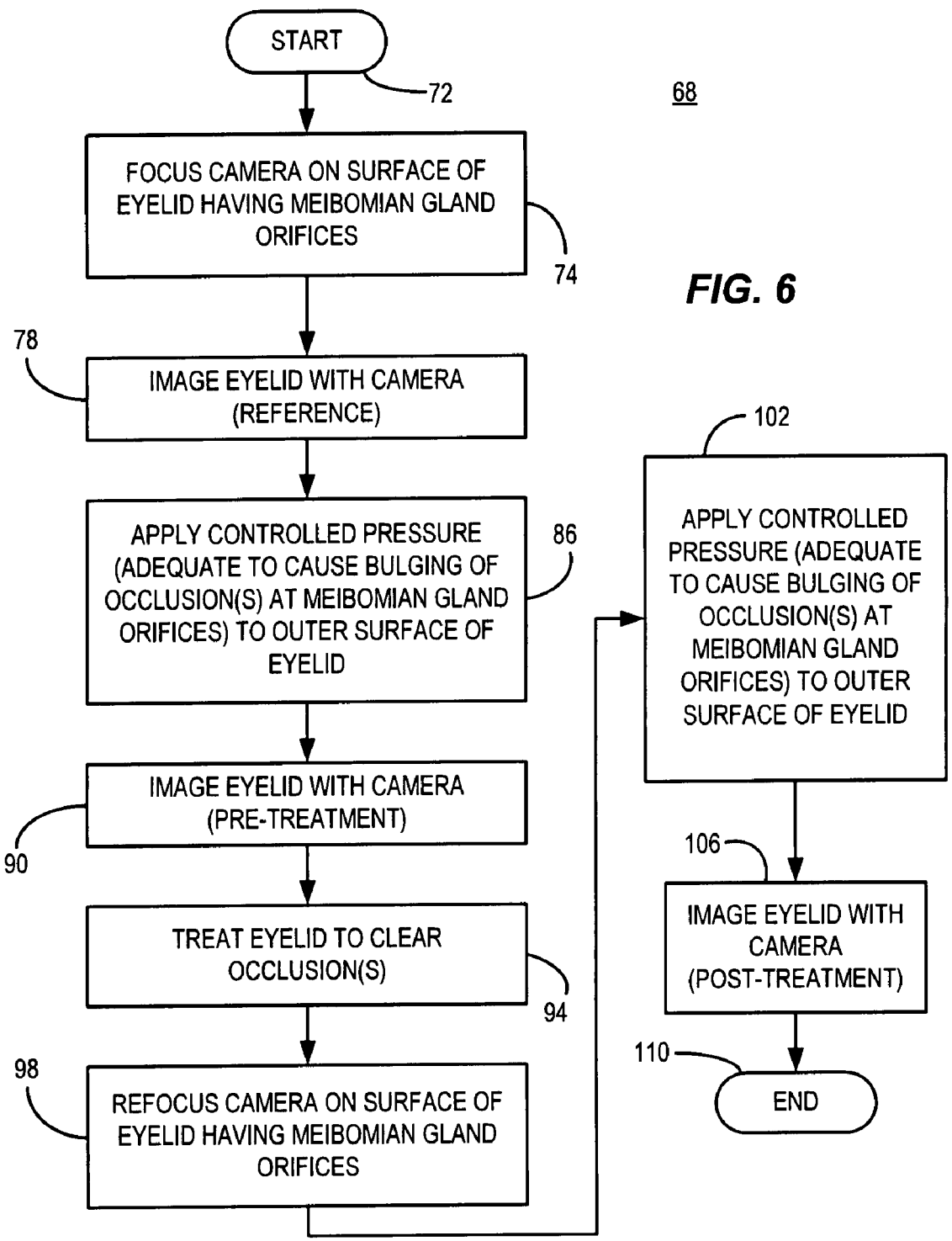
FIG. 6 is a flow chart of an exemplary orifice surface imaging process consistent with certain embodiments of the present invention.

FIG. 6 is a flow chart of an exemplary orifice surface imaging process 68 consistent with certain embodiments of the present invention starting at 72. Many variations of this process are possible depending upon what images are desired for a particular purpose. At 74, camera 54 is focused on the eyelid surface carrying the meibomian glands (in this example, the upper surface of the lower eyelid 24 at an angle suitable to produce perspective of the raised bulge or pucker or other physical deformation 34 at the surface). If desired, at 78 an image can be generated at this stage to document the normal state of the glands. Certain of the glands may appear clearly occluded in this image, but the image may not reveal all occlusions (e.g., 36).

FIG. 7 is a two dimensional depiction of an image of the eyelid having plugged meibomian glands at this stage of the process and prior to application of a pressure suitable for causing the plugs of the meibomian glands to bulge or the orifice to pucker or produce other observable physical changes in a manner consistent with certain embodiments of the present invention. For ease of illustration, the image is depicted as being taken from approximately normal to the outer surface of the eyelid, rather than at an angle showing perspective of the surface containing the orifice. Any variety of angles can be used for the images depending upon the patient, diagnostician preferences, etc. This image, if desired and taken, can be used for reference and for detection of obvious occlusions which show up as visible bulges or puckers representing a plug which may produce a recognizable pattern and colorations for comparison when a post treatment image is taken. This image can also be compared with the image of FIG. 8 as will be described later, to determine the presence of occlusions that would not be visible without application of pressure to create bulges or puckers 84 (an analogous physical deformation at the surface wherein the tissue surrounding a plugged orifice bulges around the plug to create a "pucker" effect) as illustrated.

Referring back to FIG. 6, at 86, a controlled pressure is applied to cause bulging or puckering or other physical deformation of occluded meibomian gland orifices. This pressure can be applied in a number of ways as will be described later, but are generally in the range of pressures that would simulate or mimic a patient blinking his eyes. Once the bulges or other physical deformations are apparent, at 90 they may be imaged using camera 54 to produce, for example, an image as depicted in FIG. 8 which shows a two dimensional depiction of an image of an eyelid with plugged meibomian glands with a pressure applied to cause the plug 34 to bulge or pucker to produce the physical deformations illustrated as 84 in FIG. 8 in a manner consistent with certain embodiments of the present invention. The images of FIGS. 7-8 can be used to gauge the degree, location and number of observable dysfunctional meibomian glands and to create a record thereof. Analogous records are often necessary to assure insurance reimbursement and to establish nature and degree of occlusion of the meibomian glands for diagnostic purposes.

Referring back to FIG. 6, a treatment can be conducted, as at 94, the success of the treatment can also be gauged using post treatment imaging. Thus, at 98, the camera can be refocused on the same eyelid and the controlled pressure again applied at 102 to induce bulging or puckering or other surface deformations at the orifice of occluded meibomian glands. A post treatment image can then be made at 106 with this exemplary process ending at 110.

FIG. 9 is a two dimensional depiction of an image of the eyelid of FIG. 8 after treatment to unplug the meibomian glands with pressure again applied as in 102 to cause any remaining obstructions to cause bulges or puckers 84 (two depicted) in a manner consistent with certain embodiments of the present invention.

While the above description may be construed to imply the use of still images, moving images can also be utilized, for example, to produce a pan across the eyelid at a microscopic level to image the entire eyelid. Alternatively, a suitably wide angle image with high enough visual resolution can be captured to provide ease of reference for relocation of clogged glands. The diagnostician may also apply markings to the eyelids to serve as reference points in the images to more readily identify a particular gland. It is additionally noted that the surface image may be acquired using a light source to illuminate the eyelid in a number of ways as will be described later. Such light source may be full spectrum visible light, near infrared (NIR) or other suitable spectrum or combination of spectra. In one embodiment, the light spectrum can be chosen for minimum attenuation of light when passed through human tissue such as the eyelid.

In order to assure clarity of the microscopic images, the image should preferably be produced under circumstances wherein the object being imaged is as stable as possible with exposure times being minimized. In this case, the head can be stabilized in a conventional manner using conventional ophthalmologic chin and forehead braces as are used in conventional ophthalmologic exams, with the examination braces fitted with suitable visual light photography instruments as described herein.

Figure 10:
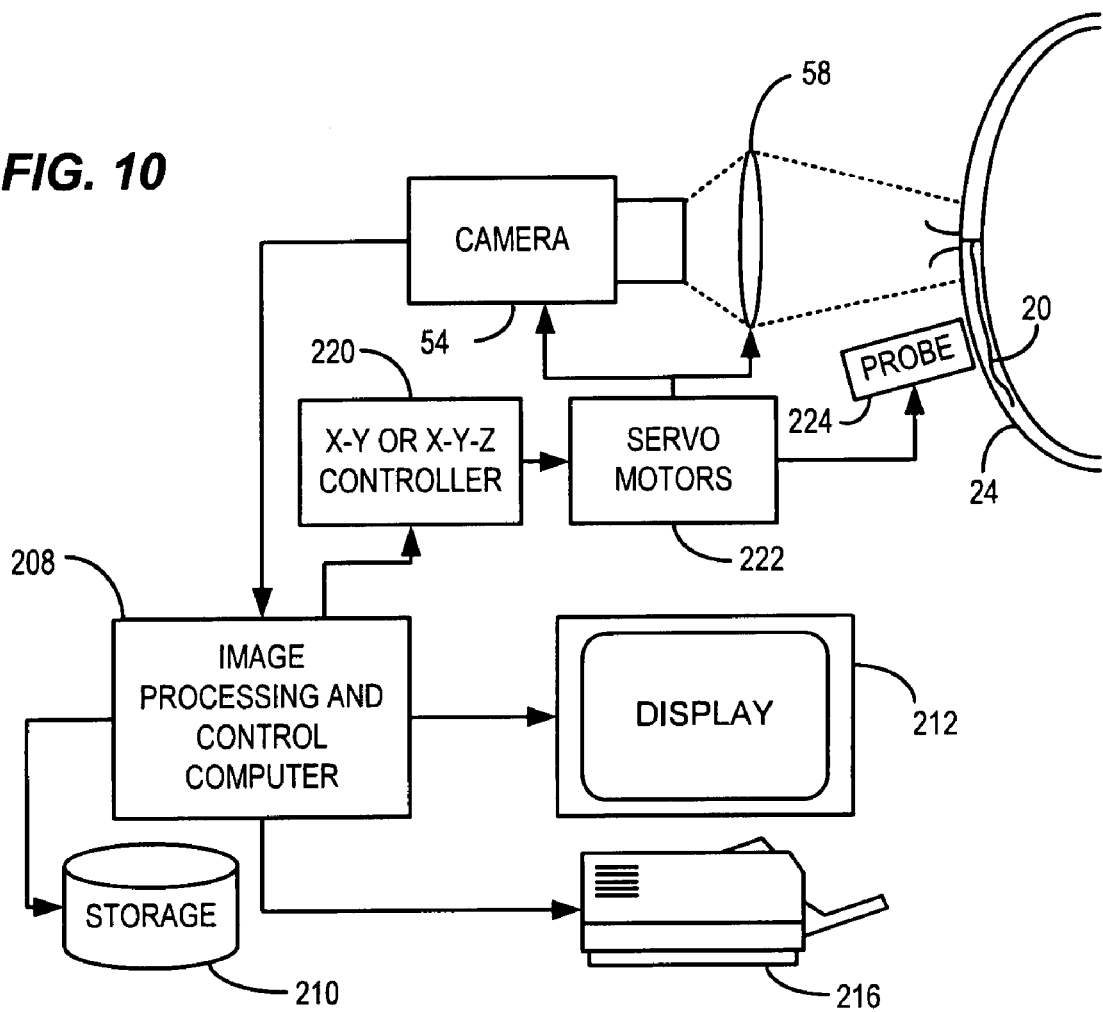
FIG. 10 is an example of a visualization system consistent with certain embodiments of the present invention.

FIG. 10 depicts a more detailed setup for visible light imaging according to certain embodiments in which camera 54 is used, through suitable magnification represented by 58, to capture an image of the eyelid (e.g., lower eyelid 24) and associated meibomian gland 20. Images from camera 54 may be rendered using either conventional photographic processes or can be directed to an image processing computer 208 that can then process and possibly enhance the image, for example by shifting of brightness, color, gamma function, sharpness or contrast or by use of tomography. The image can then be displayed on a display monitor 212, and/or stored on disk or other storage 210, or printed on a photographic quality printer 216 or any or all of the above. In addition to still images, moving images can similarly be captured in this manner to produce, for example, a pan across the eyelid in which individual frames can be captured and printed if desired. Due to the high magnification, a step and repeat process that captures a portion of the eyelid and then steps across can be used, with focusing being carried out as the camera is swept about an arc to remain normal to a selected profile of surface being imaged.

In certain embodiments, as further depicted in FIG. 10, a camera 54 and possibly light source(s) (not shown) can be moved across the eyelid in an organized manner (i.e., in a suitable arc) using an X-Y or X-Y-Z controller 220 and a suitable servo motor arrangement 222 under control of a programmed processor such as computer 208 in order to scan the entire eyelid. Scanning the eyelid can thus be accomplished manually or by use of an X-Y-Z control system. Similarly, the application of pressure to the eyelid can be effected either manually, with manual control determining when to create the image, or by coordinated action of a pressure applying probe also operating under control of the computer 208 via servo control. In other embodiments, a single probe device can apply pressure to the entire eyelid as the camera 54 is manipulated manually or by step and repeat actions under control of the computer 208 in conjunction with controller 220 and servos 222. Many variations are possible without departing from embodiments consistent with the present invention.

In order to provide references for identification of the meibomian glands, a reference scale or markings can be imaged along with the surface in order to be able to later identify the location of particular glands.

Figure 11:
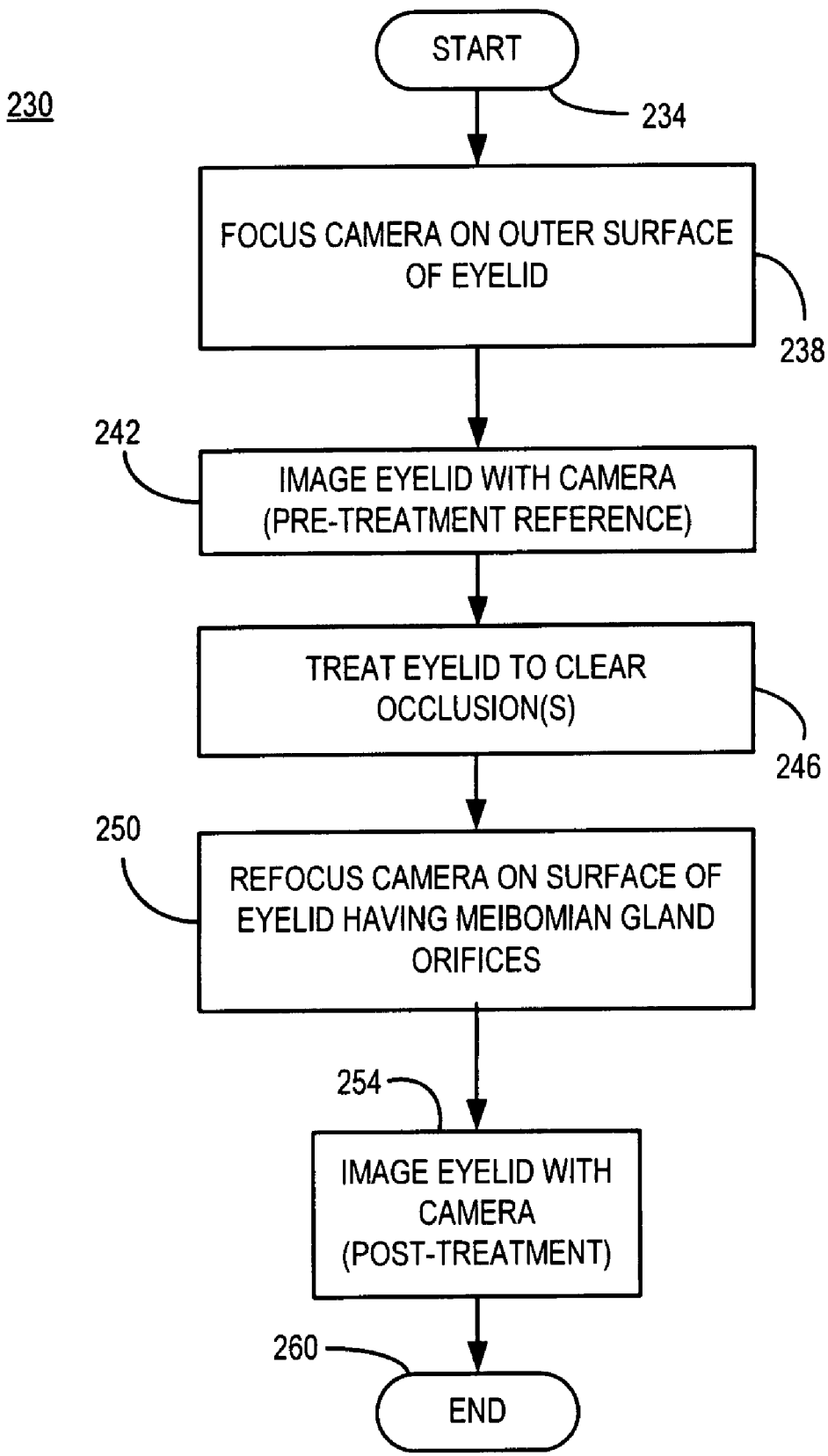
FIG. 11 is an example of a method consistent with certain embodiments of the present invention.

FIG. 11 depicts an exemplary process 230 for imaging the meibomian glands in a manner consistent with certain embodiments of the present invention starting at 234 after which the camera 200 is focused on the surface of the eyelid. One or more images are then created at 242 to create a pre-treatment reference image. This image may be processed as described above, either by fully automated means or with the assistance of manual intervention to highlight significant attributes by color modification or enhancement by computer processing. The glands may then be treated using any suitable treatment mechanism at 246. The effectiveness of the treatment can then be evaluated by imaging the eyelid in the same manner as previously by refocusing the camera on the eyelid at 250 and re-imaging the eyelid and enhancing as needed at 254. The process ends at 260. A similar process can be used with any of the imaging techniques discussed herein.

Figure 12:
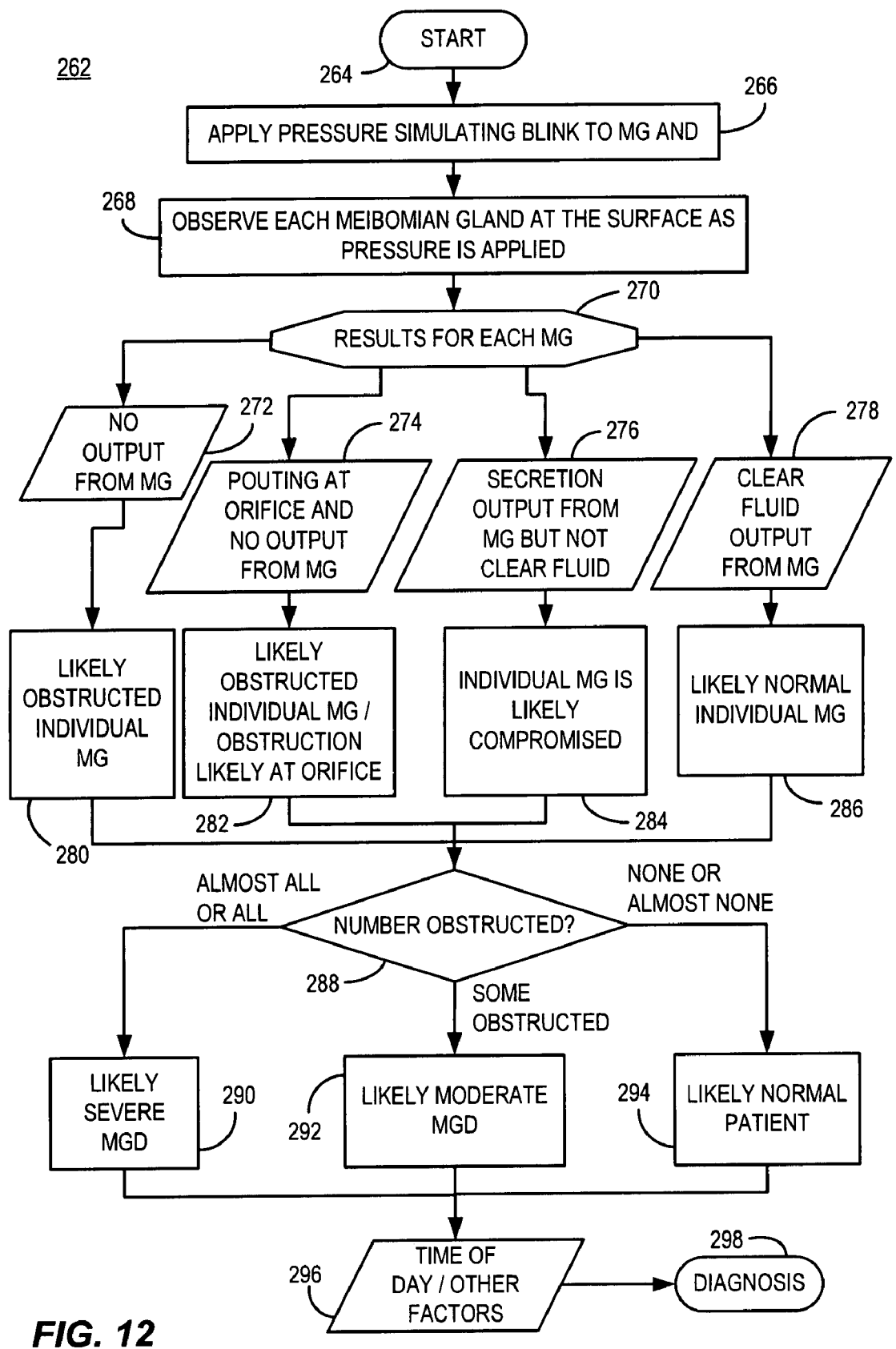
FIG. 12 is an example of a diagnosis tree consistent with certain embodiments of the present invention.

Diagnosis of the condition can be made with a reasonable degree of accuracy using the present methods in conjunction with a decision system such as the flow chart depiction of a decision tree 262 of FIG. 12 starting at 264. At 266 where the physician or technician applies pressure to the eyelid adequate to mimic the pressure applied when a person blinks. At 268, each meibomian gland is observed at the surface as the pressure is applied for results at 270. Any of several results can be observed as follows. No output from the individual MG at 272, no output from the individual MG accompanied by pouting or other physical deformation at the orifice when pressure is applied at 274, secretion output from the MG—but the secretion is not clear fluid at 276, or clear fluid output is secreted by the MG at 278.

When there is no output from the individual MG at 272, it can be tentatively concluded that the individual MG is likely obstructed at 280. When there is pouting or other physical deformity at the orifice, it can be concluded that the MG is likely obstructed and it is further likely that the obstruction is at or near the orifice at 282. If the individual MG secretes output, but it is not a clear fluid, at 276, it can be concluded at 284 that the individual MG is likely compromised (e.g., by obstruction, inflammation, infection, etc.). When clear fluid is output from the MG at 278, the individual MG is likely to be functioning normally or nearly normally at 286.

Since this assessment is made on a gland by gland basis, it is difficult for a doctor or technician to make the assessment while continually moving and refocusing his microscope, and moving the probe used to simulate the blinking pressure. Also, since the probe may repeatedly stimulate secretion from adjacent glands, it is possible to reduce or deplete the available fluids from one or more glands, skewing the test results. Hence, it is advantageous for the surface to be imaged during this process so that the assessment can be made on multiple glands with a single application of pressure and so that a reliable accounting for all or most glands can be made. This is extremely difficult to effect accurately without imaging of the surface.

Once all of the glands have been imaged and the results evaluated for each gland, an overall assessment can be made at 288. If almost all or all glands are obstructed at 288, it is likely that the patient has severe MGD at 290. If a moderate number of the glands are obstructed at 288, the likelihood is that the patient has moderate MGD at 292. If none of the glands are obstructed or only a few are obstructed, the patient likely has normal meibomian gland function at 294. The greater the number of obstructed or compromised meibomian glands, the more severe the MGD. It is difficult or impossible to provide an accurate absolute number of normally functioning glands that constitute normal MG function, since the number of glands per patient varies, as does the glandular output. Thus, some level of experience and judgment should be factored into the ultimate diagnosis. However, if all, or the great majority yield clear oil, there is probably no MGD.

At 296, other factors should be taken into consideration in making a final determination as to the presence of MGD and its severity at 298. For example, it is possible for a gland to be normal, but all of the secretion has been previously secreted during the day. In this case, the evaluation might not show any secretion upon the application of the pressure, but the gland would still be normal if it were evaluated early in the day before all of the secretion had been used. This may happen with a few or with all of the glands at any given time. The later in the day or evening the greater the probability of this phenomenon, since the gland is believed to refill during sleep when there is no blinking and no normal secretion from the gland during sleep. Other factors that may be considered are the age of the patient, observable inflammation of growth over the orifice, history, hormonal conditions, etc.

Figures 13, 14:
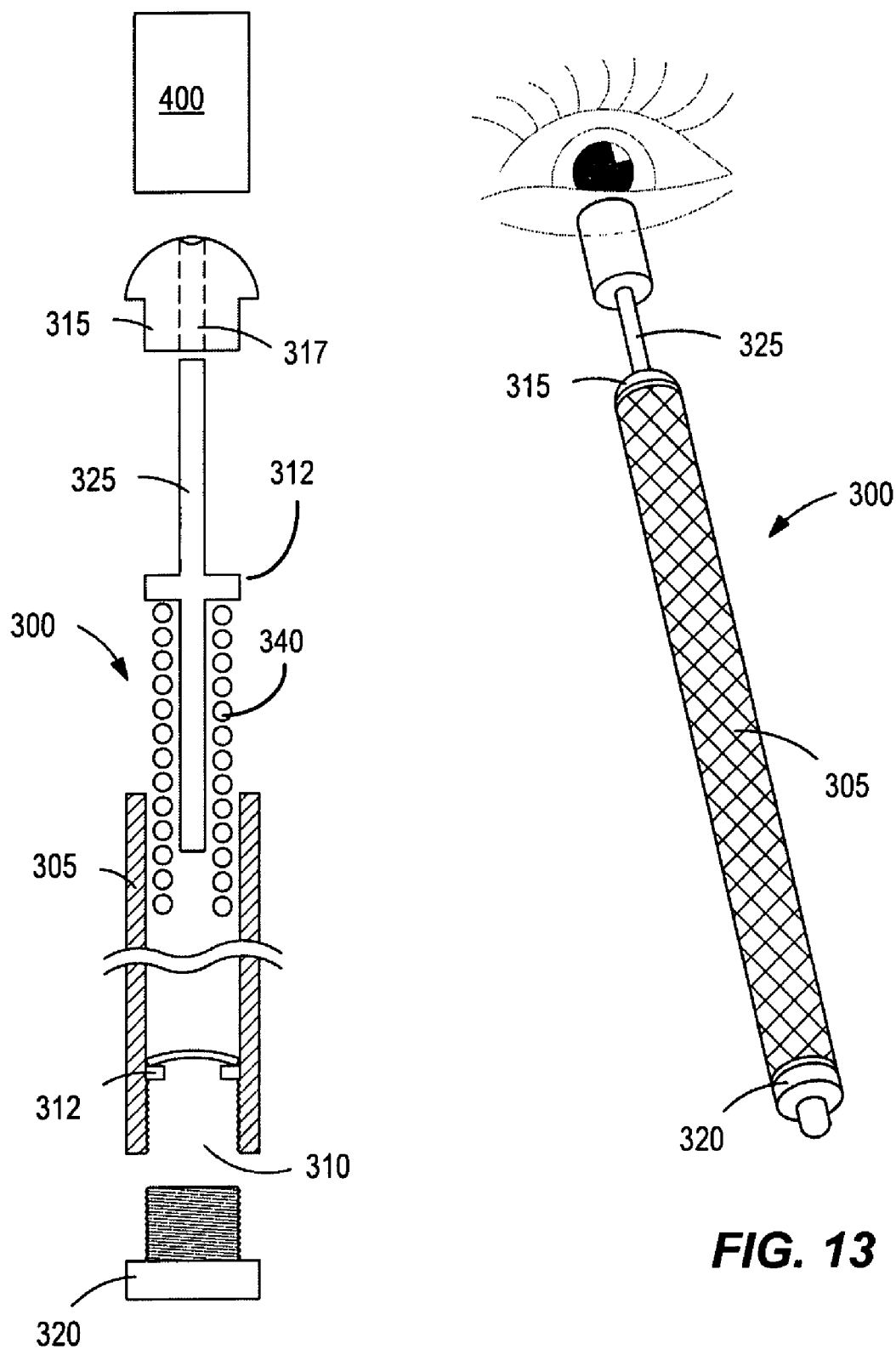
FIG. 13 is a perspective view of a first embodiment of the meibomian gland evaluation tool according to the present invention.
FIG. 14 is a broken away side view of an embodiment of the meibomian gland evaluation tool according to the present invention.

Referring now to FIGS. 13 and 14 in which a first embodiment of a device for simulating blinking pressure on the eyelid is shown, the meibomian gland evaluation apparatus generally indicated at 300 comprises an elongate shaft or handle 305 having a bore 310 there through. Located at one end of handle 305 is an annulus 312 the purpose of which will become evident as the description proceeds. One end of handle 305 mounts a cap 315 having a bore there through 317 and the opposite end of handle 305 mounts a second end cap 320. The caps may be threaded, press fitted or otherwise connected, depending upon the particular fabrication technique and materials employed. For purposes of illustration only, cap 315 is press fitted and cap 320 is threaded.

Figure 15:
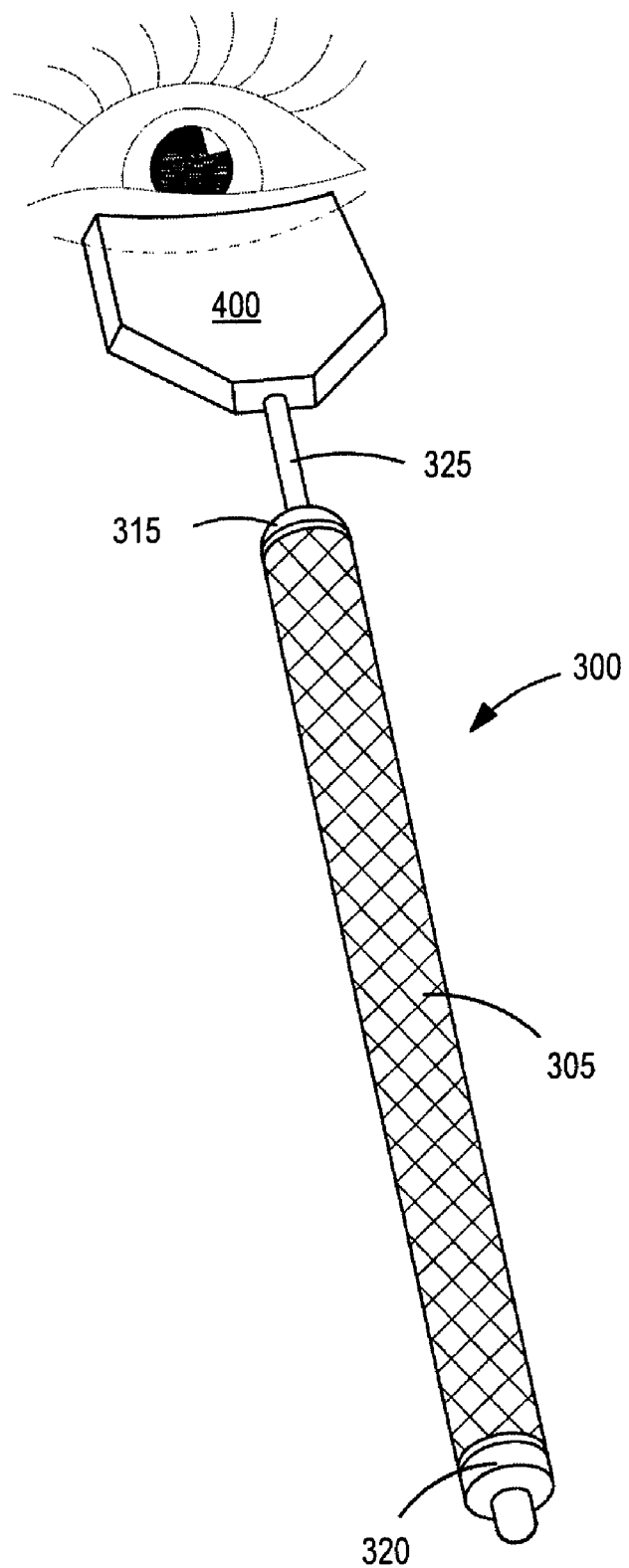
FIG. 15 is a perspective view of another embodiment of the meibomian gland evaluation tool according to the present invention.

A probe tip 400 is mounted on shaft 325 for longitudinal movement relative to the handle 305 such that when the probe tip 400 is placed against the eyelid and compressive force is applied, movement of the handle 305 a preselected distance replicates the approximate force required for natural expression of secretion from the meibomian gland. Testing has determined that this force is approximately 15 grams per 30 $mm^2$ however; depending upon the age, gender, race or other factors, this force may vary somewhat and be between approximately 10 grams per 30 $mm^2$ and 20 grams per 30 $mm^2$. Probe tip 400 is detachably connected to one end of a shaft 325 which is operatively associated with handle 305. Probe tip 400 is fabricated from a soft biocompatible material such as natural or synthetic rubber, Polyester® or other inert/non-allergenic or biocompatible materials, well known to those skilled in the art. As shown in FIG. 13, probe tip 400 is cylindrical and may be dimensioned to as to overlie one or more meibomian glands. An alternate embodiment of probe tip 400 is shown connected to the handle as illustrated in FIG. 15 and in that embodiment is designed to test a larger section of the eyelid to simultaneously evaluate multiple meibomian glands for gland function. Probe tip 400 may be press fit, snapped or threaded on to the end of shaft 325.

Per FIG. 14 shaft 325 also includes an annulus 312 proximate the tip mounting end. As shown, shaft 325 is inserted within bore 310 for longitudinal movement. A helical spring 335 is operatively associated with shaft 325 and surrounds a section thereof, biasing the shaft out of the housing. Annulus 312 serves as a support or bearing surface for spring 340.

As illustrated in the second embodiment of the invention, shown in FIGS. 16-17, the apparatus may also include an indicator means or indicator generally indicated at 408 for indicating when handle 305 has moved the preselected distance. The indicator means 408 may be selected from the group consisting of auditory, visual and tactile signals. Any of the just mentioned signal means may be employed so long as activation thereof does not significantly impact the force required to move the handle to ensure that the pressure delivered to the eyelid remains in the required range. The indicator means 408 comprises a visual indicator means or light emitting diode (LED) 405 mounted in end cap 320 such that the light emitting portion is at least partially external of the cap and the electrical leads 410 (schematically shown) extend down into the bore 310 and are connected to a battery contact plate 415 also within handle 305. A battery 420 is provided proximate the battery contact plate 415. The LED is activated by movement of the handle 305 which causes the end of shaft 325 to complete the electrical circuit and illuminate the LED. Movement of the handle 305 away from the eyelid opens the electrical circuit and turns off the LED. Circuits of this nature are well known the art and a detailed discussion thereof is not deemed necessary. Buzzers, vibrators or other indicator means may also be employed as visual indicator means.

Figure 18:
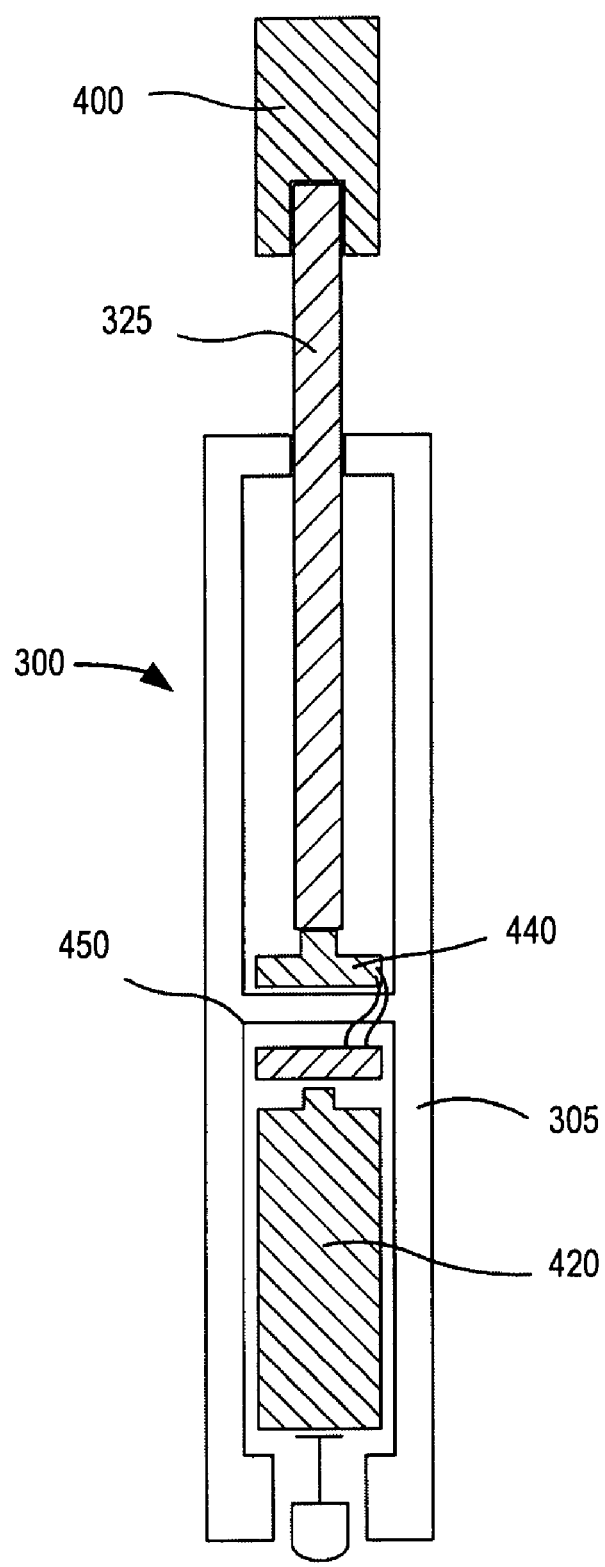
FIG. 18 is a cutaway side view of an embodiment of the meibomian gland evaluation tool according to the present invention.

In the embodiment of FIG. 18, the meibomian gland evaluation tool 300 is generally similar to the previously described embodiment except that the shaft 325 is substantially stationary and the means for sensing when the preselected pressure has been reached comprises a piezo-electric or other similar strain gauge device 440 in combination with an amplification circuit 450 (shown schematically) and which is well known to those skilled in the art. When the preselected pressure has been exerted on the eyelid, the amplifier is activated and the indicator means 408 is triggered. It is believed that this embodiment will be produced using molding techniques wherein the cylindrical handle 305 will be produced in two longitudinal halves and can be press fitted together.

Figure 19:
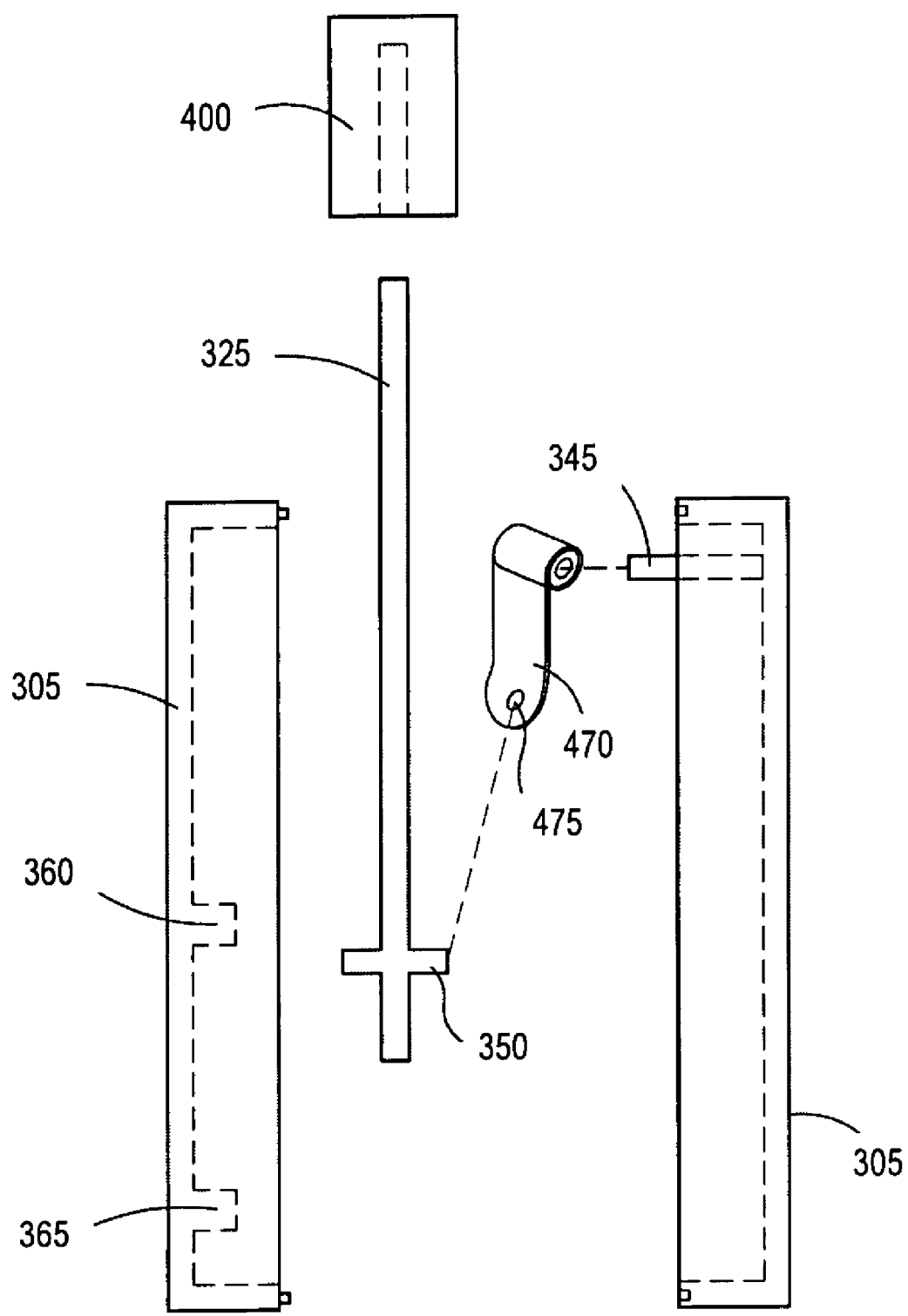
FIG. 19 is an exploded view of an embodiment of the meibomian gland evaluation tool consistent with embodiments of the present invention.

In the embodiment of FIG. 19, the preselected pressure is supplied by a spring means or constant force spring 470 which has a spring constant selected to deliver the preselected pressure to the eyelid. The constant force spring is coiled and has a connection opening 475 at the outer end. In this embodiment, it is again believed that the handle 305 will be molded in two opposing longitudinal sections that can be press fitted together. One half of handle 305 is provided with upper stop 360 and lower stop 365 in the form of protuberances extending into the bore 310 which operate to limit the travel of probe shaft 325, as will be described more fully herein below. In addition, one side of the handle includes a tang 345 extending from the inner handle wall towards the center of the bore 310. The tang 340 should be of a diameter to receive the opening in the center of constant force spring 470 and should be of a length sufficient to maintain the spring in place when the two halves of the handle are connected together. The other end of spring 470 is connected to a tang 350 located on shaft 325. In the "at rest" state of this embodiment, the spring 470 is in the coiled position and tang 350 is in contact with upper stop 360. Pressure exerted on the probe tip by movement of the handle 305 causes the spring to uncoil until tang 350 contacts lower stop 365. An indicator means is not provided as the constant force is delivered merely by unwinding spring 470. Further, it is believed that the clinician will sense when the shaft has reached its maximum path of travel when tang 350 contacts lower stop 365, but the indicator means which could buzz, flash, vibrate, or illuminate when shaft 325 is in the operating range between stops 360 and 365 could also be included with this embodiment of the invention.

Figure 20:
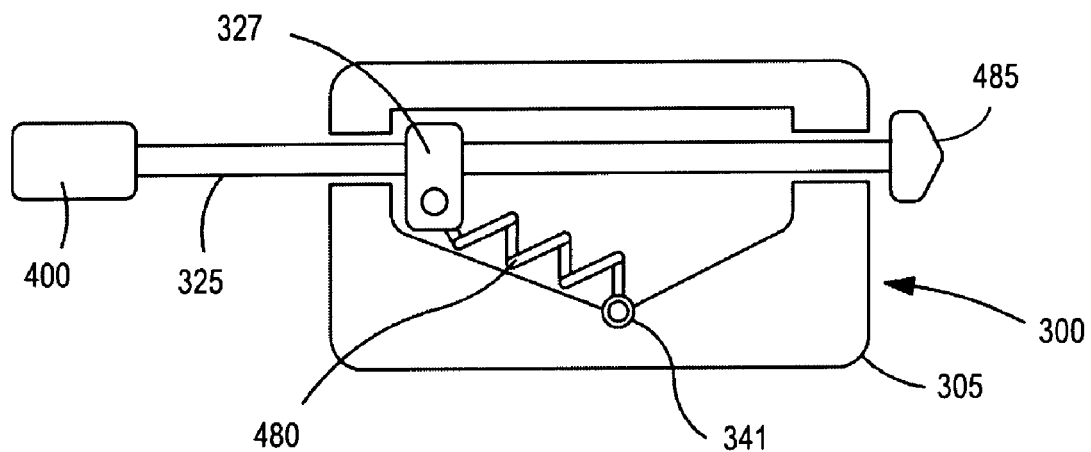
FIG. 20 is broken away side view of another embodiment of the meibomian gland evaluation tool according to the present invention.

FIG. 20 illustrates an alternate embodiment wherein the handle shape is rectangular and box-like. Shaft 325 includes a mounting bracket 327 to which one end of an over center spring or compression spring 480 is connected. As a compression spring is normally expanded, the first end rests in a cavity or pocket 341 in handle 305. The opposite end of spring 480 is connected to the bracket 327 by means of a pin or tang formed in the bracket and the shaft is biased in the extended or outward position. Pressure on the eyelid acts to compress the spring 480. When shaft 325 is pushed such that 327 is past the position of 341, shaft 325 will retract away from the eyelid. The device may be reset by pressing a reset button 485, as will be appreciated by those skilled in the art upon consideration of the present teachings.

Figure 21:
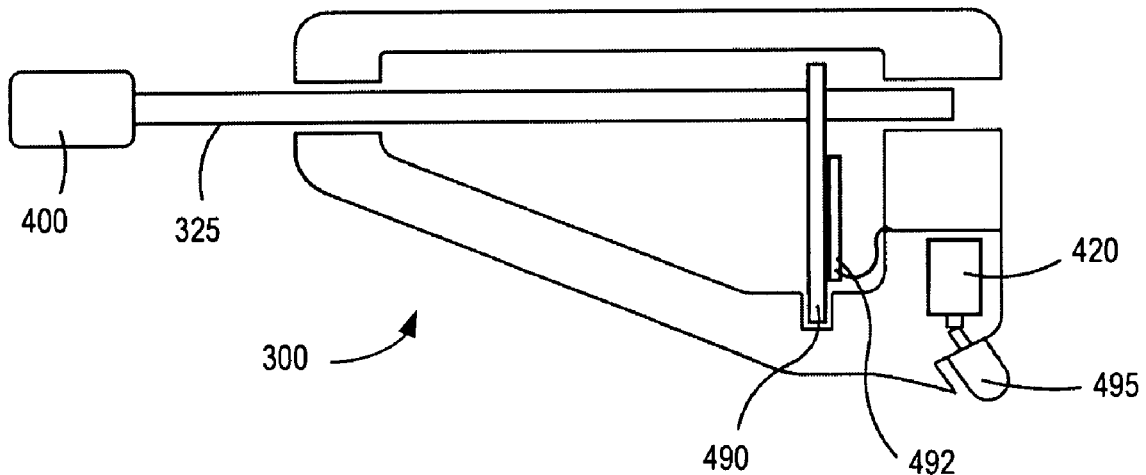
FIG. 21 is broken away side view of another embodiment of the meibomian gland evaluation tool according to the present invention.

FIG. 21 illustrates another embodiment of the meibomian gland evaluation tool 300 wherein the shaft 325 is connected to handle 305 with a cantilever beam 490. A piezoelectric transducer or strain gauge 492 together with actuator circuitry identical to that discussed in connection with the embodiment of FIG. 18. Pressure on probe tip 400 causes strain gauge to output a signal proportional to the applied pressure. When the preselected pressure has been reached, the actuator circuit activates LED 495.

In operation, considering for example the device of FIG. 16, the clinician selects the handle 300 having the desired probe tip 400 or mounts the desired probe tip 400 at the end of shaft 325. The probe tip 400 is then placed on the external surface of that section of the eyelid to be tested for meibomian gland function. The clinician also equips himself with the proper equipment (appropriate magnification from a hand held lens, head magnifier, slit lamp, microscope etc.) to be able to observe the meibomian gland orifice(s). A compressive force in the form of gentle pressure is exerted upon the eyelid by pressing the handle 305 towards the eyelid which compresses spring 340. Just prior to the end of travel shaft 325 makes contact with the battery contact plate 415, the force of about 15 grams per 30 mm$^2$ is reached in a user independent manner and the clinician observes whether the meibomian gland is properly secreting or not. The apparatus is designed so that just prior to activation of the indicator means, the cumulative force or energy stored in the spring is substantially equivalent to the force required for natural meibomian gland secretion. Of course, the other indicator means are actuated in the aforementioned manner as well.

In another embodiment (not shown) of the meibomian gland evaluation tool 300, the shaft 325 may be connected to handle 305 which is attached to a coil spring of constant force which rotates and provides force either directly on the eyelid or by pushing a linear rod attached to the handle 305 which applies force on the eyelid.

It will be noted that this apparatus of the present invention may be fabricated as a disposable, single use item primarily from plastic materials, or alternatively, may be fabricated as a multiple use probe with disposable tips, in which case that portion of the device that is re-used will be fabricated from materials of sufficient durability to withstand repeated autoclaving. Many other variations of such a tool will occur to those skilled in the art upon consideration of the present teachings.

Thus, in one embodiment consistent with the present invention a method of imaging a mammalian meibomian gland of the eyelid involves focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause a fully occluded gland to exhibit physical deformities that are observable at the surface; and from the outer surface of the eyelid, capturing a diagnostic image of the surface of the eyelid.

In certain embodiments, the captured diagnostic image is stored in an electronic storage medium or displayed on a video display. In certain embodiments, the process further involves treating the occluded meibomian glands in an attempt to clear the occlusion; and repeating the focusing, applying pressure and capturing image to capture a post treatment image to thereby document a degree of success of the treating. In certain embodiments, the diagnostic image is compared with the post treatment image to determine a degree of effectiveness of the treatment. In certain embodiments, the pressure is applied using an instrument that applies a controlled amount of pressure in coordination with capturing the image. In certain embodiments, the pressure is between approximately 10 and 30 grams/30 mm$^2$. In certain embodiments, the pressure is applied using a hand-held instrument. In certain embodiments, the process further involves relating observable conditions in the image with symptoms of meibomian gland dysfunction to make a diagnosis. In certain embodiments, a proportion of meibomian glands that exhibit symptoms of compromised function to make a determination as to a severity of meibomian gland dysfunction. In certain embodiments, the proportions of meibomian glands that exhibit symptoms of compromised function comprise those meibomian glands that do not produce clear fluid. In certain embodiments, multiple images are taken of the eyelid in order to image multiple meibomian glands. In certain embodiments, multiple images are taken by a step and repeat action under automated control. In certain embodiments, a computer readable storage medium can store instructions which, when executed on a programmed processor, carry out any of the embodiments of the method.

In another embodiment, a method of diagnosing function of a human meibomian gland of the eyelid, involves providing a diagnosis decision tree; focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause an occluded gland to exhibit physical deformities that are observable at the surface; from the outer surface of the eyelid, capturing a diagnostic image of the surface of the eyelid; and relating observable conditions in the image with symptoms of meibomian gland dysfunction to make the diagnosis. In certain embodiments, the relating involves determining a proportion of meibomian glands that exhibit symptoms of compromised function to make a determination as to a severity of meibomian gland dysfunction. In certain embodiments, the proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportion of glands that exhibit symptoms of compromised function comprise glands that secrete no fluid. In certain embodiments, the proportions of glands that exhibit symptoms of compromised function comprise glands that secrete no fluid and exhibit physical deformation at the meibomian gland orifice. In certain embodiments, the captured diagnostic image can be stored in an electronic storage medium or displayed or rendered on a display or printed. In certain embodiments, the process further involves treating the occluded meibomian glands in an attempt to clear the occlusion; and repeating the focusing, applying pressure and capturing to capture a post treatment image to thereby document a degree of success of the treating. In certain embodiments, the pressure is applied using an instrument that applies a controlled amount of pressure in coordination with capturing the image. In certain embodiments, the pressure is applied using a hand-held instrument. In certain embodiments, the pressure is between approximately 10 and 30 grams/30 mm$^2$. In certain embodiments, multiple images are captured under automated control using a step and repeat process.

In another embodiment, a method of diagnosing function of a human meibomian gland of the eyelid involves providing a diagnosis decision tree; focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause an occluded gland to exhibit physical deformities that are observable at the surface; from the outer surface of the eyelid, capturing a diagnostic image of the surface of the eyelid; rendering the diagnostic image to a viewable image display medium; relating observable conditions in the image with symptoms of compromised function by determining a proportion of meibomian glands that exhibit symptoms of compromised function to make a determination as to a severity of meibomian gland dysfunction.

In certain embodiments, the proportion of glands that exhibit symptoms of compromised function comprise glands that secrete fluid that is not clear. In certain embodiments, the proportions of glands that exhibit symptoms of compromised function comprise glands that secrete no fluid. In certain embodiments, the proportions of glands that exhibit symptoms of compromised function comprise glands that secrete no fluid and exhibit physical deformation at the meibomian gland orifice. In certain embodiments, the method further involves treating the occluded meibomian glands in an attempt to clear the occlusion; and repeating the focusing, applying pressure and capturing to capture a post treatment image to thereby document a degree of success of the treating. In certain embodiments, the pressure is applied using an instrument that applies a controlled amount of pressure in coordination with capturing the image. In certain embodiments, the pressure is applied using a hand-held instrument. In certain embodiments, the pressure is between approximately 10 and 30 grams/30 mm$^2$. In certain embodiments, multiple images are captured under automated control using a step and repeat process.

In another embodiment consistent with the present invention, an apparatus for imaging of mammalian meibomian glands of an eyelid, consistent with certain embodiments has an instrument that applies pressure to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that the outer surface of the eyelid an image containing the physical deformities of the meibomian gland orifice can be captured when pressure is applied to the eyelid.

In certain embodiments, an image processor receives an output signal from the camera and processes the image to thereby electronically enhance the image. In certain embodiments, an electronic storage device stores the captured image. In certain embodiments, a display displays the captured image, or a printer or other rendering device renders the image. In certain embodiments, the instrument is a hand-held instrument. In certain embodiments, the instrument applies a controlled amount of pressure in coordination with capturing the image. In certain embodiments, the pressure is between approximately 10 and 30 grams/30 mm$^2$. In certain embodiments, a decision tree provides a reference for comparison of image characteristics to diagnose the condition of the meibomian glands. In certain embodiments, the decision tree defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportions of glands that exhibit symptoms of compromised function comprise glands that secrete no fluid. In certain embodiments, the proportions of glands that exhibit symptoms of compromised function comprise glands that secrete no fluid and exhibit physical deformation at the meibomian gland orifice.

In another embodiment, an apparatus for imaging of mammalian meibomian glands of an eyelid, has a hand held tool to apply pressure to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that the outer surface of the eyelid an image containing the physical deformities of the meibomian gland orifice can be captured as an image. A storage device stores the captured image; and a display displays the captured image.

In certain embodiments, an image processor, receives an output signal from the camera and processes the image to thereby electronically enhance the image. In certain embodiments, the pressure is between approximately 10 and 30 grams/30 mm$^2$. In certain embodiments, a decision tree that defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportions of glands that exhibit symptoms of compromised function comprise glands that secrete no fluid. In certain embodiments, the proportions of glands that exhibit symptoms of compromised function comprise glands that secrete no fluid and exhibit physical deformation at the meibomian gland orifice.

In another embodiment, an apparatus for imaging of mammalian meibomian glands of an eyelid has a hand held tool to apply pressure between approximately 10 and 30 grams/30 mm$^2$ to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that from the outer surface of the eyelid an image containing the physical deformities of the meibomian gland orifice can be captured. A storage device stores the captured image and a display displays the captured image; an image processor, receives an output signal from the camera and processes the image to thereby electronically enhance the image.

In certain embodiments, a decision tree defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid, glands that secrete fluid that is not clear, glands that secrete no fluid and glands that both secrete no fluid and exhibit physical deformation at the meibomian gland orifice.

NIR Imaging

NIR optical imaging is an extension of visual light imaging, where the sample is illuminated with Near Infra Red (NIR) light (about 0.650-2.5 microns), either transmitted through the object, or reflected from the object, and the light is focused onto a typical red sensitive CCD camera (out to about 1.2 microns) to produce a monochromatic image. These images show the spatial resolution of structures, not the temperature profile. The spatial resolution of these images is proportional to the wavelength of light, so an image taken with 1 micron (NIR) wavelength light will have half the resolution of an image taken with 0.5 micron wavelength (green) light, all other things being equal (for example). Penetration depths in human tissue of the IR illumination can vary with in the range of a few mm to a few cm.

NIR optical imaging can be accomplished using a suitable infrared light source and highly sensitive CCD (charge-couple device) camera that records light reflected from the eyelid. For example, NIR light from a tungsten-halogen bulb penetrates human tissue to a depth adequate to illuminate the meibomian glands. A portion of the light traveling through human tissue is absorbed by chromophores, or light-absorbing molecules, in the skin's layers. By beaming light onto the patient's eyelids and measuring reflected light, differences between light reflected by chromophores and other body tissues and the fluid and/or tissue of the meibomian glands can be visualized.

NIR cameras are readily available and have a penetration depth more than enough to see through eyelids. By use of optics of a typical slit lamp microscope that are able to pass NIR frequencies (and are suitably modified if necessary to pass NIR frequencies), NIR cameras can be used to image the meibomian glands. Illumination with NIR lighting can be either from behind the eyelid for transmission, or in front of the eyelid as illustrated below for reflected light imaging.

Figure 22:
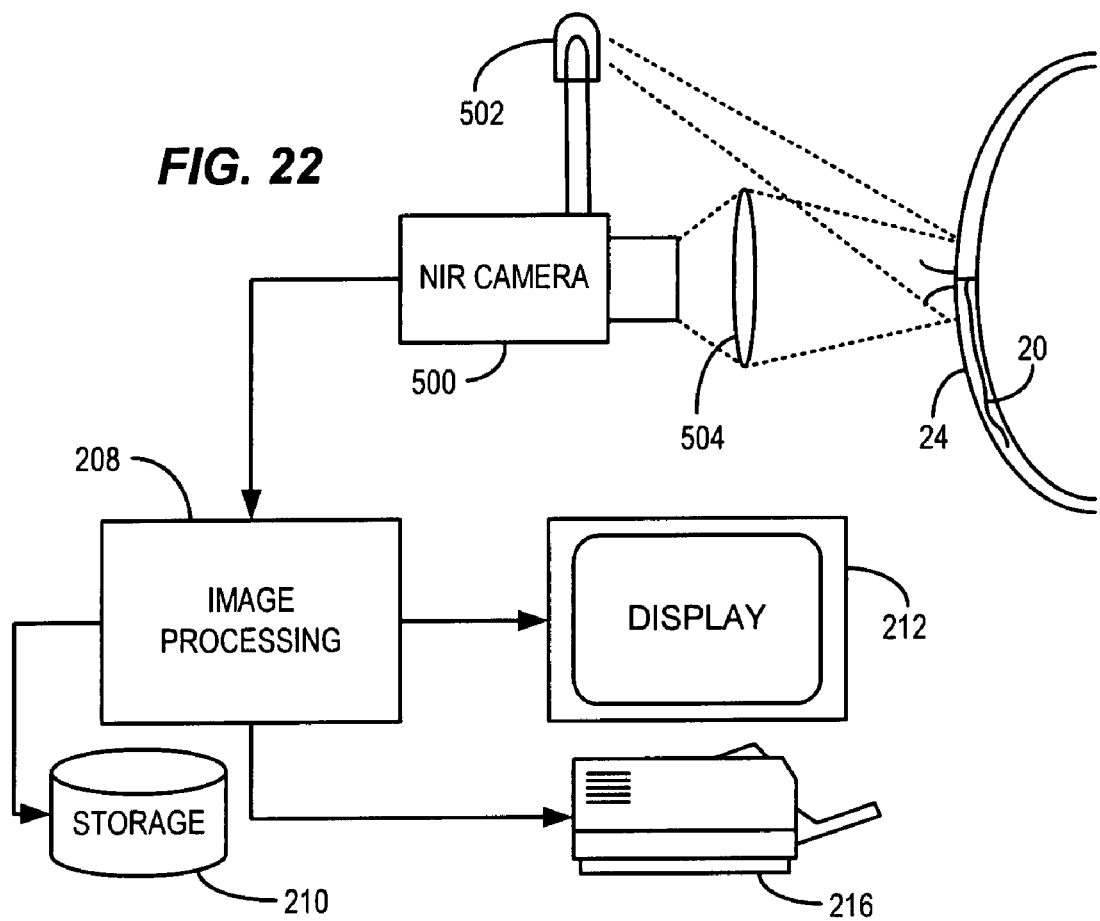
FIG. 22 illustrates an exemplary optical Infrared imaging system for imaging meibomian glands in a manner consistent with certain embodiments of the present invention.

Near Infrared imaging can be utilized to ascertain the condition and function of the meibomian glands as depicted in FIG. 22. NIR cameras, and in particular high resolution NIR photography, can be used to image the eyelid to some depth inside the tissue. The blood vessels located in the eyelid will be denser in areas outside the meibomian glands and the glands themselves will be filled with material which will have a different NIR response than the surrounding tissue. Using a High Resolution NIR camera should result in the ability to differentiate between the various tissue, the glands and material causing occlusion of the gland orifice.

In NIR imaging, the eyelids can be imaged using near infrared photography techniques, generally in approximately the 0.650 to 2.50 micron wavelength to detect differences in the transmission or reflection of infrared light from the meibomian glands. This is in comparison to the approximately the 3-8 micron wavelength used in night vision infrared imaging, where thermal radiation from the body is the imaging energy.

In this process, a near infrared (NIR) camera 500 is used in conjunction with a NIR light source 502, through suitable magnification represented by 504, to capture an image of the eyelid (e.g., lower eyelid 24) and associated meibomian gland 20. The camera 500 may produce conventional optical photographic images that can either be developed and viewed or can be directed to an image processing computer 208 that can then process and possibly enhance (e.g., by use of pseudocolor color assignment techniques to assign different colors or color ranges to different fray levels emitted from the target image) the image. The image can then either be displayed on a display monitor 212, or stored on disk or other storage 210, or printed on a photographic quality printer 216 or any or all of the above. In addition to still NIR images, moving NIR images can similarly be captured in this manner to produce, for example, a pan across the eyelid in which individual frames can be captured and printed if desired.

In accordance with certain embodiments consistent with the present invention, the NIR camera may be based upon readily available high resolution NIR cameras. Either a conventional lens can be used with multiple images taken to image various areas of the eyelid, or a specially designed lens can be provided which provides for focus on the curved surface of the eye, and thereby compensate for the curvature of the eye.

An NIR camera can be utilized to image the eyelid to some depth inside the tissue. The blood vessels located in the eyelid will be denser in areas outside the Meibomian glands and the glands themselves will be filled with material which will have a different NIR response than the tissue around it. A High Resolution NIR camera should be able to differentiate between areas of tissue and areas of glands. The wavelength and optics used for the NIR camera should be selected to provide suitable imaging of the meibomian glands and can be optimized by experimentation. Additionally, it may be advantageous to digitally process the resulting images to enhance the contrast level and/or assign coloration to distinguish between the NIR responses of the various tissues.

In addition to the NIR photography technique using a slit lamp microscope, imaging can be carried out using a suitable microscopic objective lens. As noted previously, the central duct of a meibomian gland is on the order of about 100 microns in diameter. Additionally, the glands are separated by approximately 1 mm and have an orifice on the order of approximately 0.1 mm (based upon a limited sampling of human subjects). The orifice is closed when not secreting—the size of the orifice of approximately 0.1 mm is obtained by placing pressure on the gland to open the orifice and then making the estimation of the 0.1 mm size. The TABLE 1 below shows the resolution of objective lenses for light at 900 nm (0.9 microns) wavelength. Based upon these data, a microscopic objective lens having between about 60× and 10× magnification should be suitable for providing high resolution imaging of a meibomian gland. The field of view listed in TABLE 1 refers to the diameter of the viewable area of the sample.

TABLE 1

| | Objective | | | | | |
| --- | --- | --- | --- | --- | --- | --- |
| | 63X | 40X | 20X | 10X | 5X | 2.5X |
| Numerical Aperture | 1.32 | 0.75 | 0.5 | 0.3 | 0.15 | 0.075 |
| Resolution (microns) | 0.42 | 0.73 | 1.10 | 1.83 | 3.66 | 7.32 |
| Field of View (microns) | 317 | 500 | 1000 | 2000 | 4000 | 8000 |

It should be noted that if one wished to see the total lid of 30 mm, a field of view of about 30,000 mm would be needed—consider in view of legal considerations. It is further noted that the total image magnification can increased by a factor of 10× with a 10× eyepiece on the microscope, however the resolution is determined by the objective lens.

In certain embodiments, the NIR camera has an objective lens magnification of between about 60× and 10× between about 650 and 900 nm wavelength. As an example the range of 16× to 25× is the most common range used with a slit lamp for imaging one or several glands. However, it would also be desirable to image the entire lid to see the general characteristics of all of the meibomian glands. This can be performed in the range of 10× to 16×. Also, if imaged on a video screen consider the magnification assume the lid is 30 mm wide=1.2 inches—One could only use 10× to see the entire lower lid if the screen were 12". Thus extend magnifications to preferred 10× to 25×, and range as great as you decide would not compromise patent—60 is on the high side since the use of any magnification over 25 and certainly 40× is difficult because of exaggeration of movement. In certain embodiments, the imaging is carried out using NIR optical imaging approximately in the 0.650 to 2.5 micron wavelength range. In certain embodiments, the imaging is carried out using trans-illumination photography. In certain embodiments, the trans-illumination is produced by oblique illumination of the eyelid from an anterior surface thereof. In certain embodiments, the trans-illumination is produced by lighting the eyelid from a posterior surface thereof. In certain embodiments, the trans-illumination is produced by use of a scleral lens serving as a light source from the posterior surface of the eyelid. In certain embodiments, the trans-illuminating is carried out using a lenspiece comprises an array of light emitting elements mounted to a substrate suitable for contact with eyeball. In certain embodiments, the NIR radiation includes radiation having wavelength that is either absorbed or transmitted preferentially through lipid rich material versus tissue surrounding lipid rich tissue. In certain embodiments, at least one of the imaging and re-imaging is carried out while pressure is applied to the eyelid that simulates an amount of pressure caused by blinking the eyelid.

Thus, a method of near infrared (NIR) imaging of a meibomian gland involves illuminating the meibomian glands with NIR radiation using an NIR light source; focusing an NIR camera on a region of an eyelid containing the meibomian gland; making a first NIR image of the meibomian gland; applying a pressure suitable for simulating blinking pressure on the meibomian gland; optionally refocusing the NIR camera on the region of the eyelid containing the meibomian gland; and making a second NIR image of the meibomian gland while the pressure is being applied. The method is preferably carried out with the NIR camera having an objective of between about 60× and 10× between about 650 and 900 nm wavelength. Light emitting diodes (LEDs) producing light in or about this range may provide useful sources for illumination, and some leeway should be provided to account for the limited spectrum that can be produced by LEDs.

Figure 23:
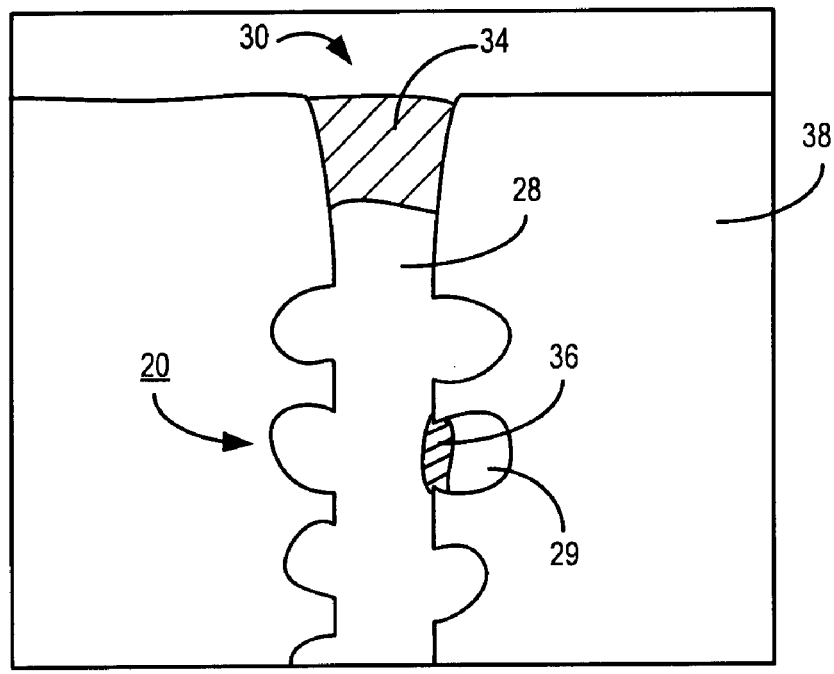
FIG. 23 is an example representation of an IR image of an occluded meibomian gland consistent with certain embodiments of the present invention.

FIG. 23 depicts an exemplary image that might be obtained via optical near infrared photography. In this image, simplified for purposes of this illustration to demonstrate only anatomical features of interest, it is expected that an image of an occluded meibomian gland will transmit IR radiation at differing intensities at the location of the occluded orifice 30 (at 34) and the occluded acini 29 (at 36) than would be expected at a normally functioning gland. Thus, the image can be processed to present a different density or color of the image at orifice 30 and occlusion 34 and acini 29, central duct 28 and occlusion 36 than of the remainder of gland 20 and surrounding tissue of the eyelid 24. Note that while FIG. 23 illustrates a single meibomian gland, this is for illustrative purposes only since one, more or all of the glands or the entire eyelid or both eyelids may be imaged in a single image or multiple images in various embodiments.

Figure 24:
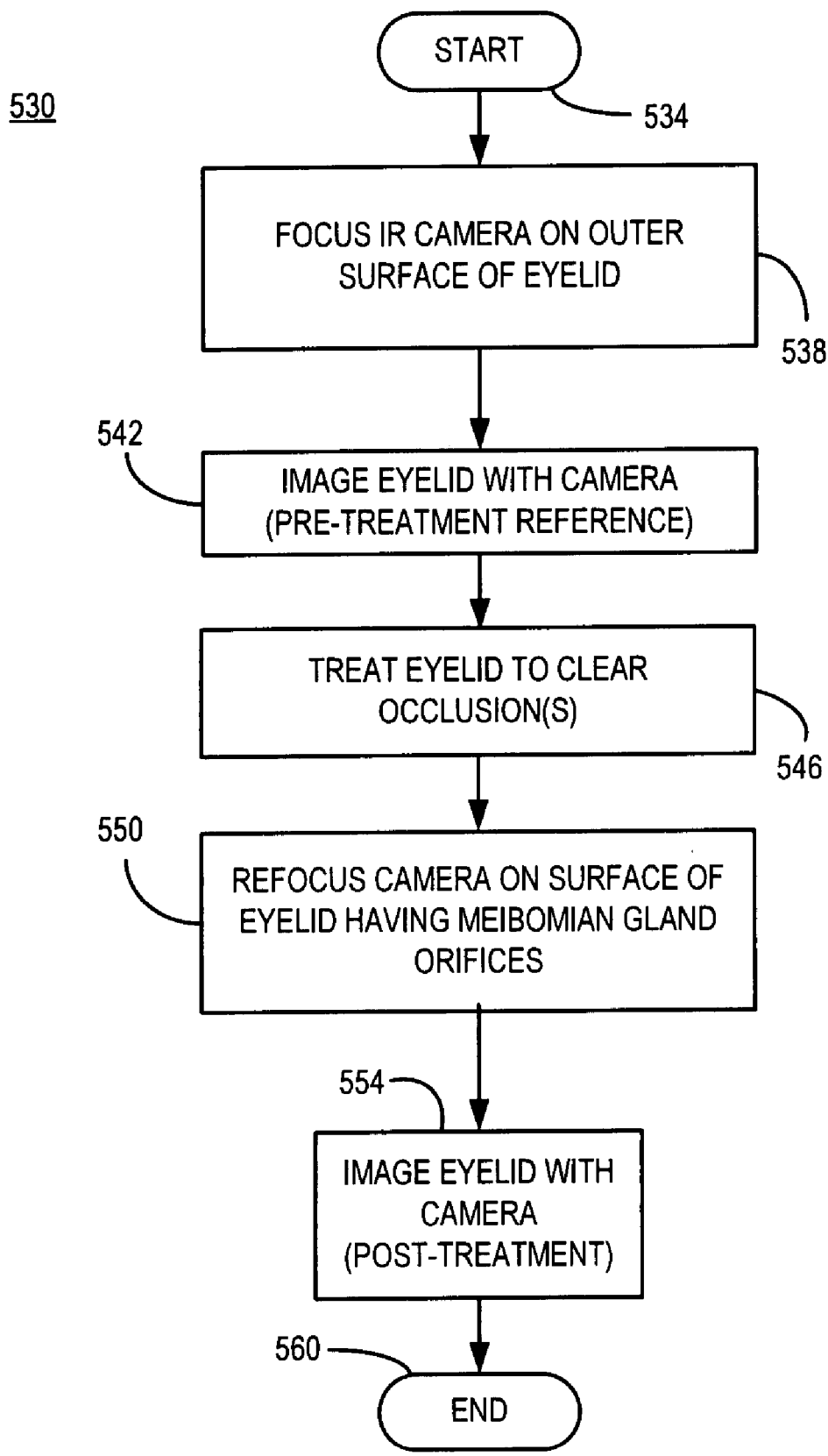
FIG. 24 is a flow chart depicting an exemplary method of use for the IR visualization techniques consistent with embodiments of the present invention, but with simple modification is applicable to any of the techniques described herein.

FIG. 24 depicts an exemplary process 530 for imaging the meibomian glands using near infrared photography in a manner consistent with certain embodiments of the present invention starting at 534 after which the NIR camera is focused on the surface of the eyelid (or on the MG where possible). (For other imaging techniques, analogous processes can be utilized with suitable modification e.g., using a visible light camera or ultrasound device rather than an IR camera.) An image is then created at 542 to create a pre-treatment reference image. This image may be processed as described above, either by fully automated means of with the assistance of manual intervention to highlight significant attributes by color assignment or enhancement. The glands may then be treated using any suitable treatment mechanism at 546. The effectiveness of the treatment can then be evaluated by imaging the eyelid in the same manner as previously by refocusing the IR camera on the eyelid at 550 and re-imaging the eyelid using infra-red photography and enhancement as needed at 554. The process ends at 560. As has been previously discussed, the application of pressure may also be used during the imaging process to augment the process and determine the state of function of the glands. Either still or moving images may be used in the imaging process, and pressure can be applied as described above to mimic blinking pressures.

As noted above, in one embodiment, the IR camera may be fitted with a lens designed to correct for the curvature of the human eye. While there is variation in the size and curvature of the human eye, a lens designed for the average can likely be used across the spectrum of eye sizes with adequate performance.

As is the case with any microscopic imaging process, the image should preferably be produced under circumstances wherein the object being imaged is as stable as possible. In this case, the head can be stabilized in a conventional manner using conventional ophthalmologic chin and forehead braces as are used in conventional ophthalmologic exams, with the examination braces fitted with suitable infrared photography instruments as described above.

Trans-Illumination

A new form of trans-illumination can be used to image the meibomian glands in one of several ways. In one variation illuminating light can be directed at the outer anterior surface of the eyelid at an angle, with imaging also taking place from the outer anterior surface of the eyelid. This is referred to as oblique illumination. In a second variation, light can be directed from behind the eyelid through the eyelid with imaging taking place through the outer surface of the eyelid. In a third variation, the surface is illuminated from the front in a manner such that the light source partially blocks the image being recorded, with averaging, adding or otherwise combining of multiple images being used to produce a complete image. In each instance, the meibomian gland is illuminated in order to visually examine the gland using light transmitted through the eyelid tissue. The eyelid can then be imaged using still or moving photography (visible light, NIR or IR or other suitable light wavelength) in a manner similar to that depicted above.

Figure 25:
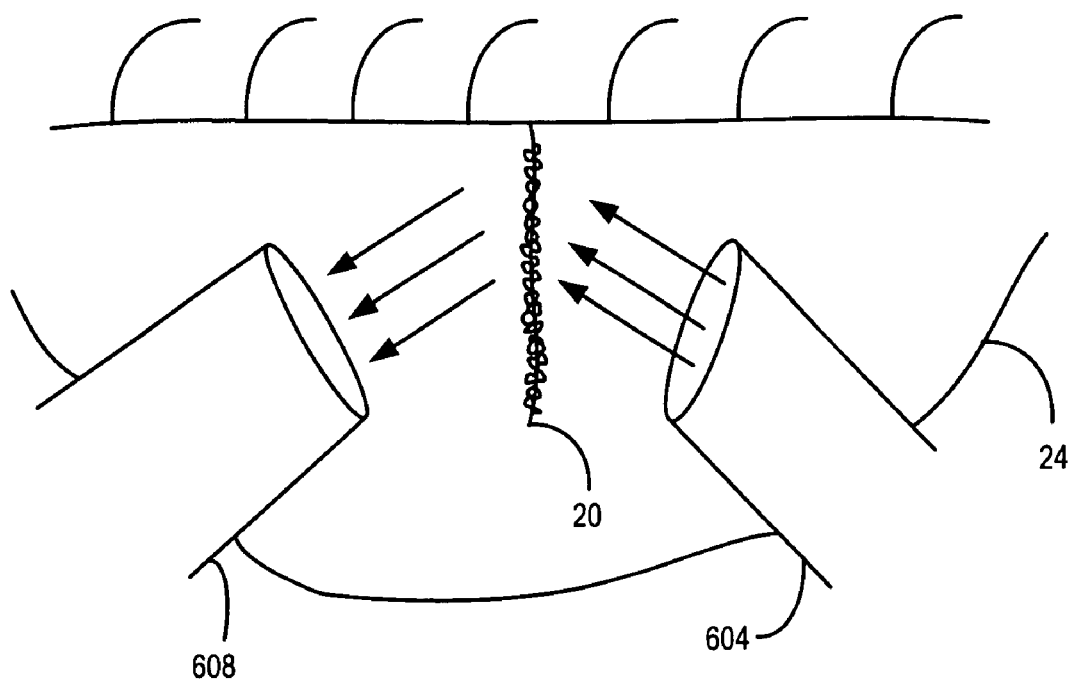
FIG. 25 is an illustration of an exemplary system for oblique illumination for trans-illumination imaging of an eyelid in a manner consistent with certain embodiments of the present invention.
Figure 26:
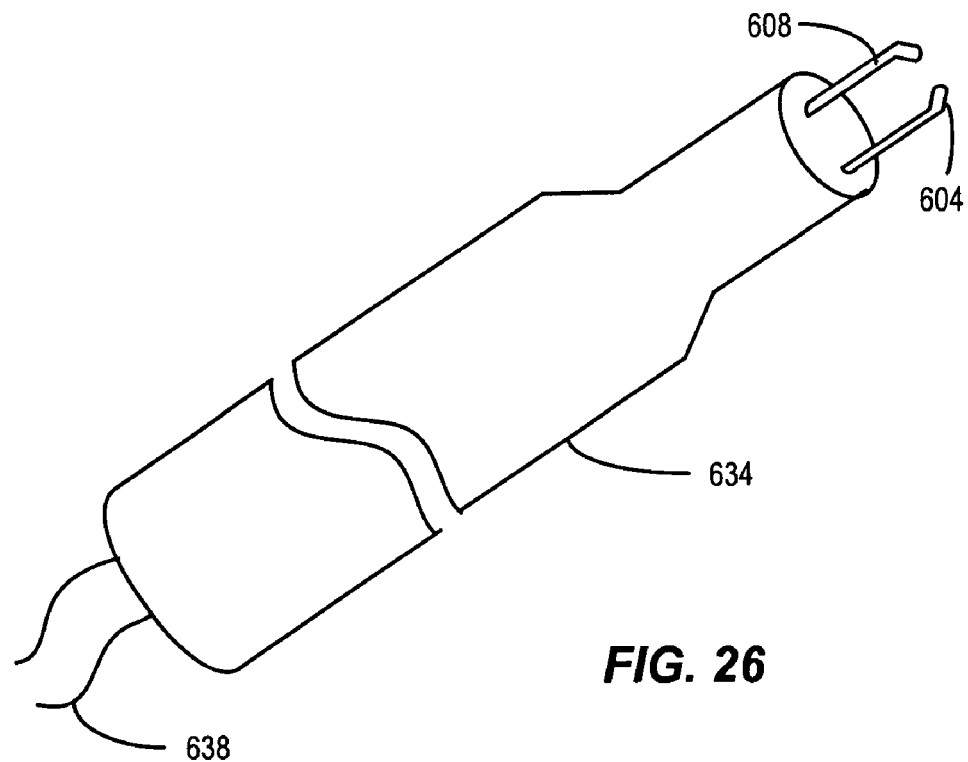
FIG. 26 depicts an exemplary hand-held instrument for manual imaging of a portion of the eyelid using oblique illumination consistent with certain embodiments of the present invention.

The first variation of this technique is depicted in FIGS. 25-26. With reference first to FIG. 25 the basic concept of oblique trans-illumination for imaging the eyelid and associated glands is depicted. In this illustration, light is directed toward the eyelid at a suitable angle to cause a section of the flesh of the eyelid to be trans-illuminated by transmission of light through the flesh itself. In this case, a light source 604 is simply depicted as a light conducting fiber that directs light to a desired location of the outer surface of the eyelid. The light can be of any suitable wavelength including near IR radiation. A light receiving element (which again is depicted as an optical fiber) 608 is positioned on the same outer surface of the eyelid in order to image the trans-illuminated area of the eyelid and one or more meibomian glands such as 20. In certain embodiments, this technique can be used to completely manually probe the eyelid as with the manual probe depicted in FIG. 26, while in other embodiments; the eyelid can be scanned by moving the probe (light source and receiver) in an organized manner (e.g., under computer control) over the eyelid and electronically assembling a larger image of the eyelid.

In accordance with various embodiments, the source fiber 604 and the receiver fiber 608 can be individually manipulated, or may be contained in a single hand-held probe 634 as depicted in FIG. 26. In such a probe, both fibers can be optically isolated and stress relieved in a single cable 638 that is attached to a combined light source 612 and optical receiver unit 616 as shown separately in FIG. 27. The tips of the probe can be of such design as to capture the image of a small (e.g., approximately circular, oblong, rectangular, etc.) region of the eyelid using a single imaging element or a small array of imaging elements (e.g., CCDs), or a vertical or horizontal stripe of the eyelid so as to capture the length of an individual or set of meibomian glands by using a rectangular array of imaging elements, or any other suitable array of elements. Additionally, a full or partial image of the eyelid can be assembled electronically by stitching, adding, averaging or otherwise electronically combining overlapping images using photographic stitching or combining techniques. The imaging element or elements should be matched to the wavelength of light that is to be captured. In certain embodiments, NIR radiation is used and hence, the imaging elements can be suitable for receipt of light in the NIR spectrum.

Figure 27:
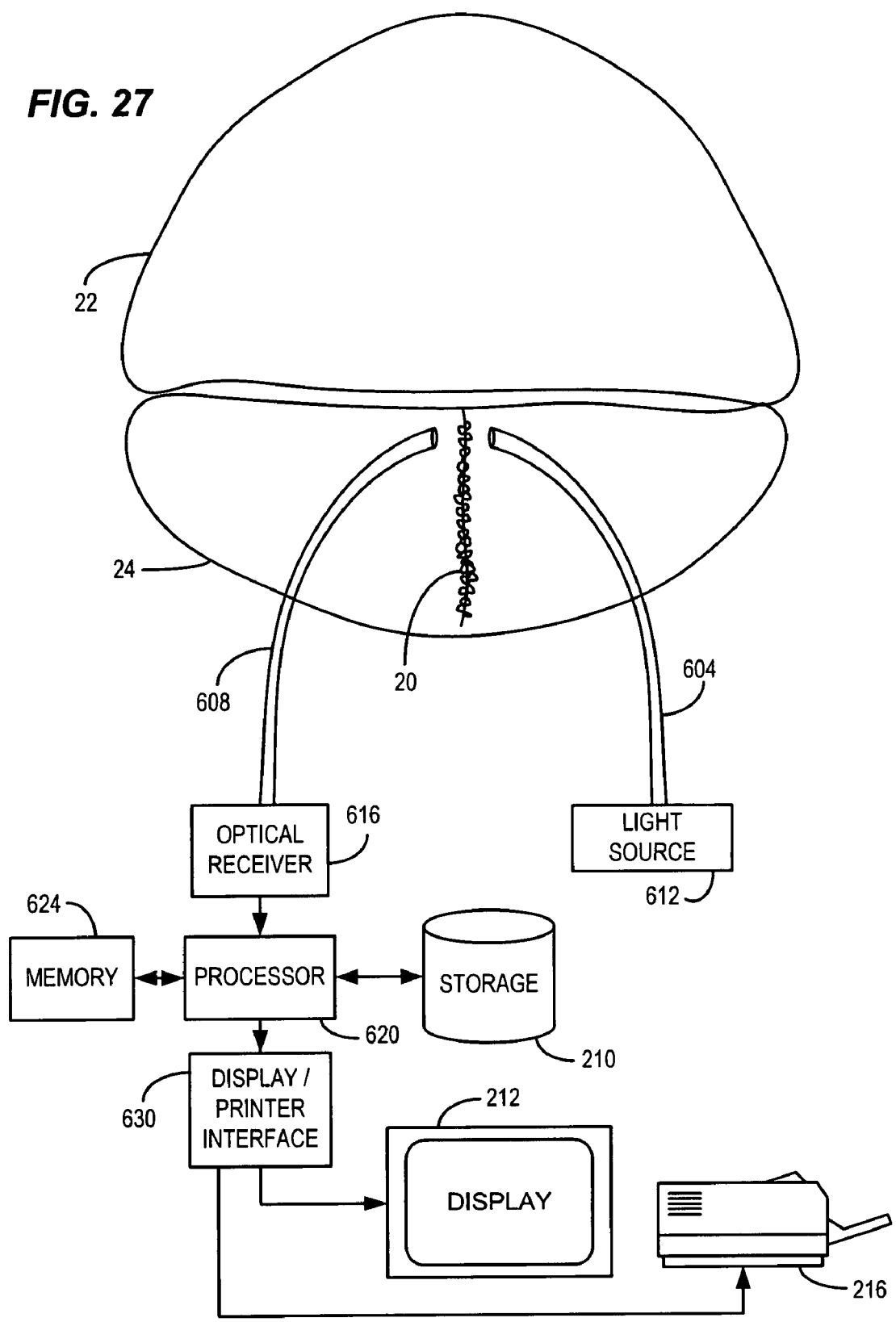
FIG. 27 is an illustration of a trans-illumination system consistent with certain embodiments of the present invention.

FIG. 27 depicts a more complete image of the imaging setup in which fiber 604 directs light from a suitable light source such as a light emitting diode, laser, NIR source, incandescent or halogen source 612 to the eyelid. The resulting image is received via light conduit 608 that is matched to the light source at an optical receiver 616 (also matched to the light source) which delivers a digital representation of the image to a processor such as a microcomputer 620 having associated working memory 624 and mass storage such as disc drive storage 210. The image can be stored at storage 210 for later retrieval, processing or enhancement. The image can also be viewed in real time or at a later time on display 212, or can be printed on printer 216, each of which is connected to the processor 620 via a suitable display and/or printer interface 630.

In certain embodiments, as described previously, the light source and optical receiver can be moved across the eyelid in an organized manner using an X-Y (or X-Y-Z) controller and a suitable servo motor arrangement (not shown in this illustration) under control of the processor 620 in order to scan a larger surface. Scanning the eyelid can be accomplished manually or by use of an X-Y control system as illustrated. In such an embodiment, the light source 612 and optical receiver 616 may be scanned across the eyelid in a suitable pattern to produce a full X-Y scan under control of X-Y scan controller 658 driving a servo arrangement 662, while high resolution camera 650 records the results.

Figure 28:
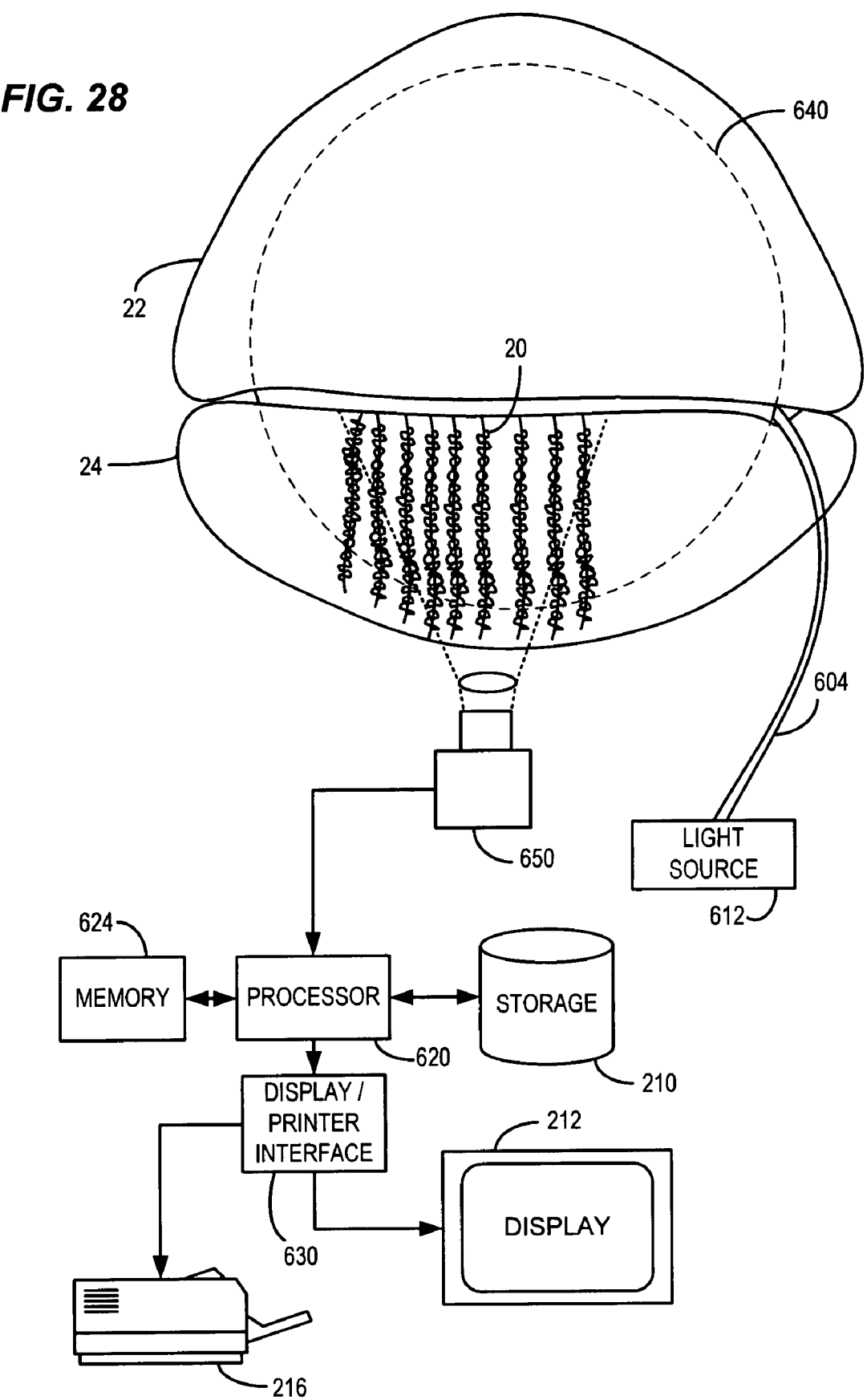
FIG. 28 is an illustration of an exemplary rear trans-illumination system consistent with certain embodiments of the present invention.

In another variation of the trans-illumination technique, depicted in FIG. 28, a device similar to a contact lens or scleral lens 640 is temporarily placed in the eye to act as a source of light that is fed by light source 612 via fiber 604. Fiber 604 is shown as illuminating the lens at an edge, but could also illuminate the lens near the center or from multiple locations without limitation in order to shine light through the eyelid from behind. The light can be of any suitable frequency matched to the imaging process, including white light or NIR radiation. This contact lens 640 can resemble a small eye shield similar to a scleral lens. A high resolution camera 650 can then be used to image the eyelid or the eyelid can be observed during illumination through a slit lamp microscope. Preferably, the contact lens has a reflective back side to protect the eye from exposure to high intensity light, coupled to a frosted lens element that scatters the light directed thereto by the light fiber 604 which is optically coupled to the frosted lens element or other dispersive arrangement such that the light of desired wavelength is scattered throughout the lens. Multiple sizes of the lens can be provided to approximately accommodate eyes of various sizes, but need not be a perfect fit since the duration of need for installation of the lens against the eye is short term, and should result in minimal discomfort. Local anesthetic can also be used to minimize discomfort.

The lens 640 is illuminated by light of the desired wavelength (e.g., NIR or visible) passing through fiber 604 so that light is thereby passed from the posterior surface of the eyelid through the eyelid itself to illuminate the interior surface of the eyelid for imaging. This produces an image of the interior of the eyelid that can be captured in much the same manner as an image produced by shining a bright flashlight through a human hand (wherein, bones are readily visible through the flesh). Light of various colors or color combinations (including visible, UV, IR, NIR or combinations thereof) can be used in this embodiment.

Therefore, the present trans-illumination techniques can provide more consistent results with greater patient comfort than the technique in current use. In addition, automatic image capture and analysis can be incorporated. In this embodiment, a light source built into a small eye shield 640 similar to a scleral lens as described above provides the illumination source without providing a significant amount of heat. Then high resolution camera 650 is used to visualize the resulting image. Various techniques can be used to increase the signal to noise ratio under low light conditions. Some of these techniques can produce motion artifacts in the image that should be noted in considering or image processing the output image. Image processing can be utilized to minimize such artifacts.

Figure 29:
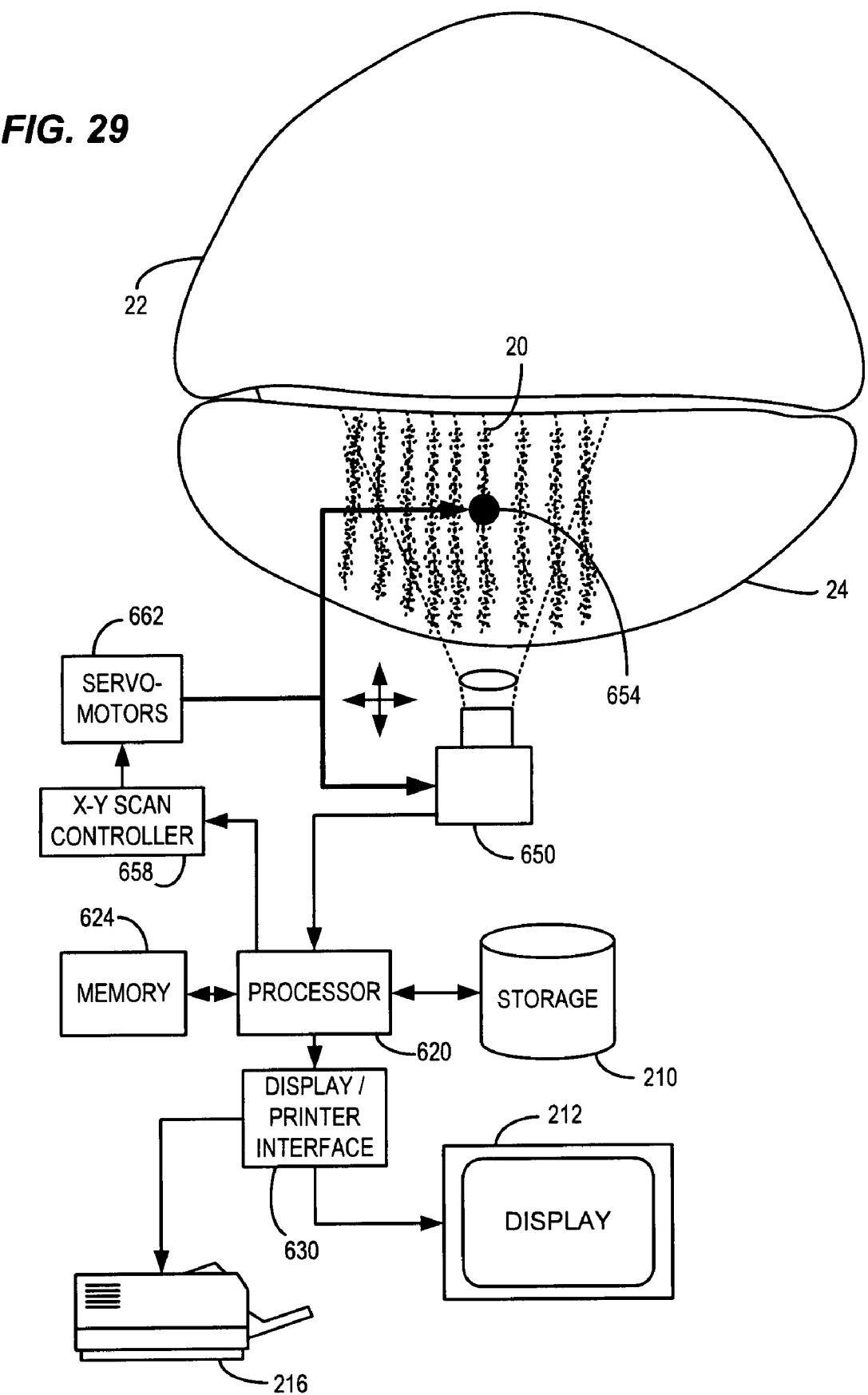
FIG. 29 depicts another exemplary trans-illumination technique consistent with certain embodiments of the present invention.

In a third alternative embodiment, as depicted in FIG. 29, an LED light source (or other suitable light source or light conduit therefrom such as a NIR light source) 654 can be placed close to or in contact with the outside of the eyelid (e.g., 24). The light source 654 is then manually or automatically scanned across the eyelid in a suitable pattern to produce a full X-Y scan under control of X-Y scan controller 658 driving a servo arrangement 662, while high resolution camera 650 records the results. The various image frames taken during the scan are then combined (e.g., stitched, averaged or added) together at processor 620 resulting in a composite trans-illuminated image. Alternately, the image of the light source can be subtracted from the resulting images. The theory behind this technique is similar to shining a flashlight on your hand and looking at the hand from the same surface as the light source is illuminating. You can see the tissue around the flashlight but you cannot see through the flashlight itself because it is blocking your field of view. However, if you move the flashlight around and record images at many positions, it is then possible to eliminate the flashlight body from your image by combining all of the resulting images together. Further image processing may also be carried out to enhance the resultant image. For example, in one embodiment, image recognition techniques can be used to recognize the shape of light source 654, and subtract that image from each image. Data from other images can then be inserted into the image from which the light source is subtracted. The process may be potentially further enhanced by experimentation with various illumination wavelengths.

In the above example, light is provided directly in front of the camera, while in prior examples, light was provided at the side of the camera or behind the eyelid. Hence, it will be evident that the light source can be placed in any suitable location with respect to the eyelid and the camera in order to produce trans-illumination of the meibomian gland or glands without limitation.

Figure 30:
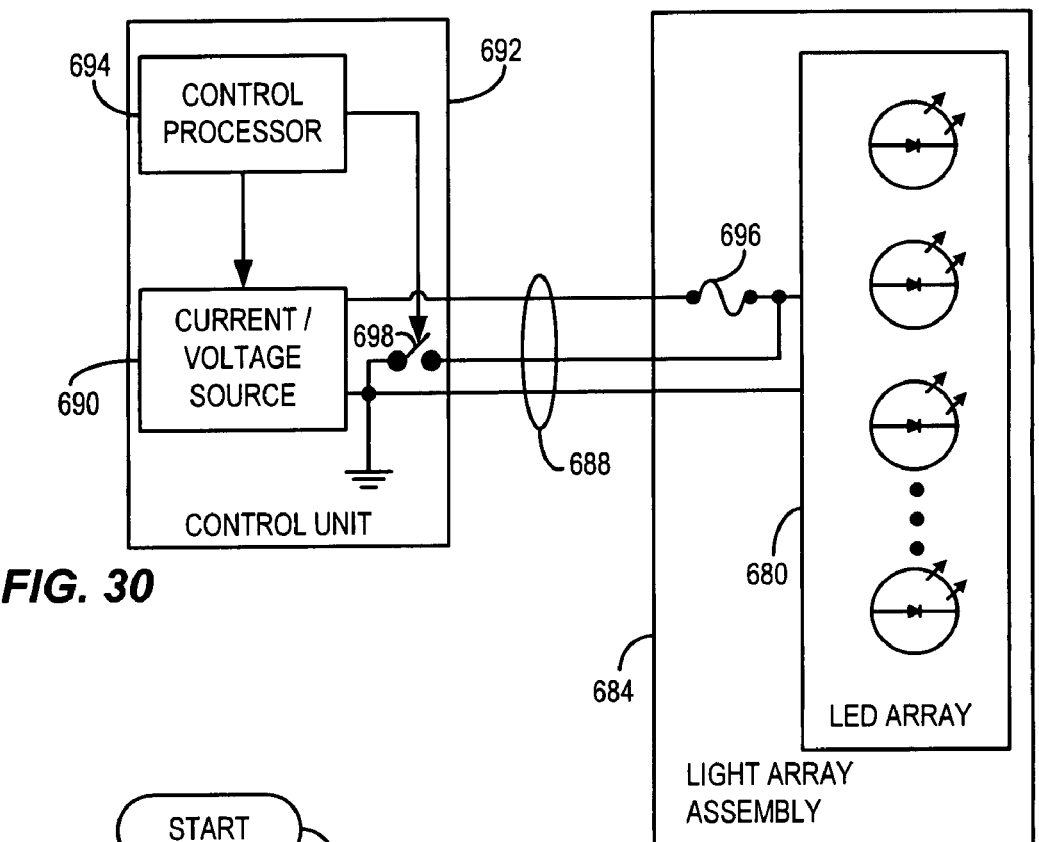
FIG. 30 is a circuit diagram for a trans-illumination apparatus consistent with certain embodiments of the present invention.

Referring now to FIG. 30, another embodiment of a trans-illumination apparatus is depicted schematically which can provide not only a high level of light transmission through the eyelid, but also can have therapeutic benefits of providing heat. In this embodiment, an array of light sources such as Light Emitting Diodes (LEDs) 680 are arranged on a light array assembly 684 which is then mounted to a lenspiece (e.g., again resembling a scleral lens) that is placed in contact with the eye and the eyelid covering the assembly. Wiring then passes through a suitable type of wiring harness mechanism (wires or a connector of any suitable design) to a power source (e.g., voltage or current source) 690 that forms a part of a controller device 692. In this embodiment, power source 690 operates under control of control processor 694 to supply a controlled suitable combination of current and voltage to the light array assembly to produce the desired illumination. The power source may be current limited or may include a series resistance or use other techniques to assure that the LEDs are not damaged by excess current.

In addition to providing a high level of trans-illumination, the present apparatus further provides heating of the tissue of the eyelid, which has been found to be therapeutic in melting or otherwise relieving occlusions of the meibomian glands and other abnormalities of the eye and eyelid. Since LEDs are generally about 5-7% efficient in generation of light, and the remainder of the power sent to the LED array 680 is converted to heat, the trans-illumination can accompany heat generation and therapy. U.S. Provisional Patent Application No. 60/880, 850 filed Jan. 17, 2007 describes a device in which heating elements are used as a part of a scleral lens-like assembly, and the present light array assembly can serve the purpose of the heating elements described in that application and may further provide the desired trans-illumination effect discussed above.

Since the light array assembly 684 is used in intimate contact with eyes and may carry a risk of contamination if reused, it is desirable that the assembly 684 is configured to be a one-time use assembly. In order to facilitate this, it is further desirable that the assembly be disabled so as to discourage further use once the device has served its purpose on a single patient, thereby providing protection against transmission of disease. Hence, in one embodiment, a fusable link is provided in the path that supplies power to the LED array 680. At the end of a treatment or diagnosis cycle, the control processor 694 can close a switch 698 in order to intentionally blow the fusable link 696 rendering the light array assembly inoperative. In certain embodiments, the fusable link may be realized by providing a narrow segment of a flex circuit trace that is inherently less capable of carrying higher levels of current than a larger trace. In other embodiments, a separate circuit element may be used.

In some embodiments, blowing the link can be accomplished as shown with grounding the LED array 680 side of the fusable link 696 so that positive current flow is shorted to ground directly through the link bypassing the LED array 680. In such a configuration, it may also be desirable to provide a diode in the path toward ground (toward the switch) in the light array assembly to assure that power cannot be supplied surreptitiously to the light array assembly in a path that bypasses the fusable link without considerable difficulty and rework. While three contacts or connections between the control unit 692 are shown, other connections can also be provided in order to permit the control processor to monitor temperature or carry out other functions, as will be appreciated upon consideration of the teachings of the above Provisional Patent Application.

Figure 31:
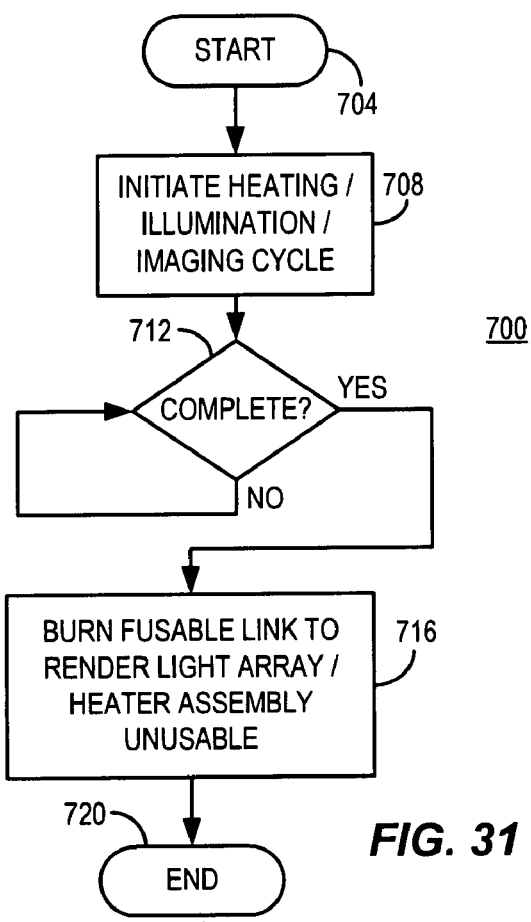
FIG. 31 is a flow chart depicting an illumination or heating process having the burning of a fusable link at the end of the cycle in a manner consistent with certain embodiments of the present invention.

The process just described is presented as process 700 of shown in the flow chart of FIG. 31 starting at 704. The processor 694 instructs the heating and/or illumination device 684 to operate through a cycle of illumination and/or heating actions in any suitable manner at 708. Once the cycle of heat treating or illuminating is completed at 712, the processor 694 closes switch 698 in order to burn out fusable link 694 (or takes any other suitable action to disable the light array assemble thereby preventing reuse) and the process ends at 720.

FIG. 32 depicts the physical and mechanical configuration of the light array assembly 684 in accord with one embodiment. In this embodiment, the lenspiece 724 resembling a scleral lens in shape (i.e., somewhat hollow dome shaped) is designed to fit over the eyeball on the concave side and is configured to carry LED array 680 on the convex side. The LED array 680 is configured to provide a sub-array adjacent the lower eyelid margin and a sub-array adjacent the upper eyelid margin as depicted as 680A and 680B respectively. A male connector member 728 extends outward approximately normal to an approximately centralized area of the convex surface of lenspiece 724 and provides an array of electrical contacts 732 that can be connected to a female electrical connector 734. In this embodiment, the female connector 734 is configured to receive the male connector member 728 and clamp to it by engaging a flexible snap-together portion 738 with a contact portion 742 that carries pins or other contacts that electrically engage the contact array 732. The connector provides an electrical cable that is electrically connected to the contact portion in order to send and receive electrical signals to the light array assembly 684. Desirably, connection should be made to the male connector member without applying significant pressure to the eyeball through the lenspiece.

Figure 33:
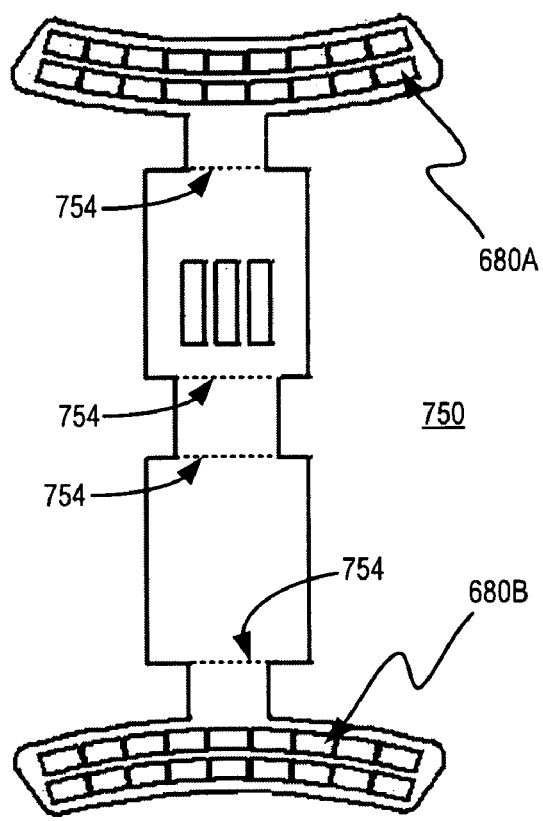
FIG. 33 illustrates a flex circuit used in an embodiment of the light array assembly consistent with certain embodiments of the present invention.

FIG. 33 depicts a flex circuit 750 (i.e., a thin, flexible substrate carrying circuit traces and electronic components) that is used in certain embodiments to realize a portion of the light array assembly 684. The flex circuit 750 depicted has an array of surface mounted LED elements that form sub-arrays 680A and 680B. These sub-arrays form the LED array 680 and can be electrically configured in any suitable series and/or parallel configuration to permit application of power to the array so as to create the desired illumination. The flex circuit 750 also carries the array of electrical contacts 632 that are used to interconnect with the LED array 680. For clarity, no particular electrical connection is specifically shown, since any suitable series and/or parallel arrangement can be used if appropriately supplied with power. The flex circuit can also be provided with other electronic circuit elements as desired to carry out other functions, including temperature monitoring and fusable link. The fusable link can be fabricated by making a narrow trace on the flex circuit.

The dashed lines 754 depict folds or creases that are made in the flex circuit in order to mount the flex circuit 750 to the lenspiece assembly 684. This is further depicted in FIG. 34 which illustrates the folds made in flex circuit 750 to conform to the shape of male connector member 728 and eyepiece 724. Once the folds are made, the flex circuit 750 can be bonded to the eyepiece 724 and the connector member 728 using any suitable adhesive mechanism. Since the surface mount LEDs that form LED array 680 protrude above the surface of the flex circuit 750, they may provide a rough edge that will be uncomfortable to the wearer. In order to minimize this, an over-molding or coating, for example of a plastic, or other coating designed to smooth the surface can be applied to the assembly to make the outer surface thereof smoother. The thickness that can be tolerated with reasonable comfort for short periods of time by a human subject of such a light array assembly is surprisingly thick. The approximate thickness of the embodiment of assembly 684 depicted that is placed between the eye and the eyelid can be between about 0.5 mm and about 6 mm and should be readily tolerated for short time periods by human subjects. The 6 mm upper limit of the range is possible for many, but at upper limit for most eyes is more desirably in the range of up to 3.5 mm FIG. 35 depicts another embodiment of the light array assembly depicted generally as 770 which is functionally equivalent to assembly 684 and interchangeable therewith. In this embodiment, the lenspiece has a flex circuit similar to 750 applied to a convex surface thereof, but does not incorporate a connector member 728. Instead, wires 746 are directly attached to the flex circuit and are connected using any suitable connection method (e.g., soldering or conductive adhesive connection) to the control unit 692. A connector may advantageously interposed between assembly 770 and the control unit to facilitate reuse of the control unit and disposal of assembly 770. In accordance with this embodiment, the central portion of the flex circuit 750 is shortened as compared with the circuit shown on FIG. 33, and provided with contact areas for direct connection to the wires 746.

In this embodiment, the lenspiece is preferably opaque to protect the eyeball from the highly intense light of the light array assembly. Additionally, the flex circuit is preferably white or reflective to assist in providing a uniform light source. The coating should be biologically acceptable for placement between the eyeball and eyelid and may be tailored to provide multiple purposes. In addition to providing a smoother surface for contact with the sensitive underside of the eyelid, it can provide light scattering properties by being translucent or otherwise diffusive, or may provide color filtering properties if desirable, or may be clear for maximum light transfer without departing from embodiments consistent with the present invention.

Figure 36:
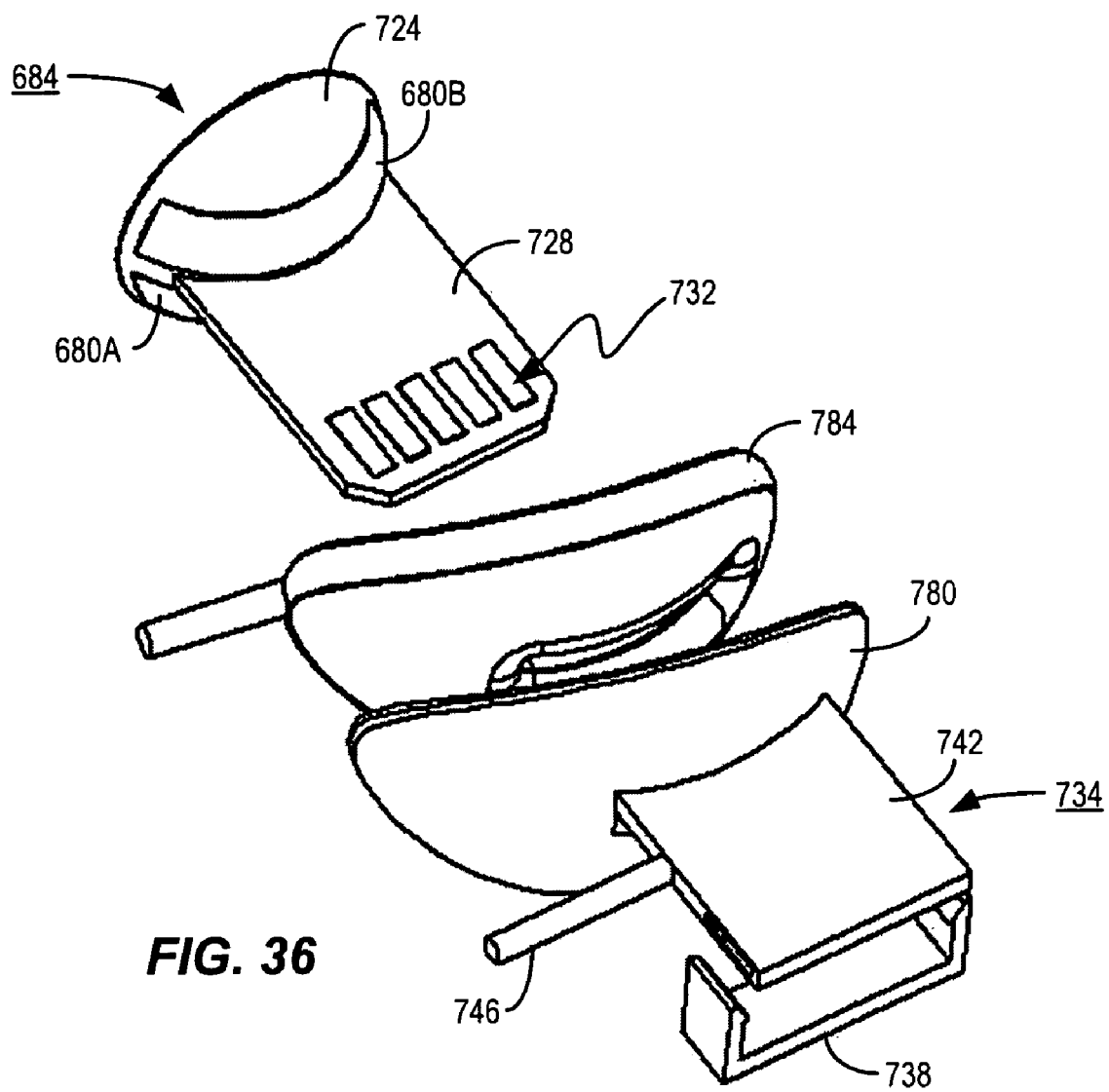
FIG. 36 illustrates a combined light array assembly eyepiece with a mechanism for producing pressure on the eyelid using a bladder in a manner consistent with certain embodiments of the present invention.

U.S. Provisional Patent Application No. 60/880,850 filed Jan. 17, 2007 describes a heat treatment apparatus for treatment of the eye. The assembly of FIG. 32 above can be adapted for use as a treatment device in the same manner as that of the provisional application as illustrated in FIG. 36 by addition of an eye shield or eyecup 780 and a fluid bladder 784 which provides for mechanical manipulation of the eyelid in order to assist in expressing melted obstructive material from the meibomian glands. In this case, the light producing devices also produce heat, and by regulating that heat, the heater assembly as shown in the provisional application, in all embodiments, is simply substituted with the light array assembly. In such embodiments where the light source also provides (or is provided as a part of) a heat source, the eyepiece serves as an insulator that prevents the heat treatment from and a mechanism is provided for applying pressure to the eyelid or lenspiece 724.

In the most basic form, lenspiece/insulator 684 is concave in shape on the eyeball side and mirrors the curvature of the eyeball, substantially similar to a contact lens. As employed herein, the term "insulator" is intended to include any component or material wherein there is greater resistance to thermal conduction or radiation towards the surface of the eye than towards the eyelid. Stated alternatively, in the insulator thermal energy radiates more easily towards the eyelid than towards the eyeball surface in order to minimize the possibility of causing injury to the eyeball. In a model that supplied heating alone, the diameter was sufficient to more than cover the cornea or in the approximate range of 15 mm to 25 mm would be sufficient for most eyes assuming a corneal relief zone of approximately 16 mm. It will be noted however, that the diameter of the insulator can vary beyond the ranges stated above. Further, the lenspiece 684 is constructed from a biocompatible material such as polymethylmethacrylate (PMMA) or in the case of the prototype that was constructed, epoxy or other materials well known to those skilled in the art. The insulator may be flexible, but ideally should be only minimally compressible, as will become clear from the discussion that follows.

According to certain embodiments of the invention, the lenspiece insulator 684 is inserted on the surface of the eye, behind the rear surface of the eyelid and should include smooth edges so as not to scratch or cut either the eyelid or the eye. As used herein the term "eyelid" or "eyelids" is intended to include the upper lid and the lower lid, either in singly or in combination. The insulator provides a back plate against which pressure may be applied. In limited circumstances when the obstruction in the meibomian gland channel is minimal, the meibomian gland may be cleared merely through the application of pressure externally applied to the eyelid, such as gentle finger pressure. More specifically, with the insulator in place behind the eyelid, finger pressure is applied to the external surface of the eyelid, the eyelid being sandwiched between the finger and the insulator.

In other instances, the meibomian gland obstruction may be blocked to a degree greater than can be treated with simple pressure alone. In such cases it is necessary to apply thermal energy to the eyelid in order to loosen, break up, fracture, soften or liquefy at least a portion of the occlusion. Thermal energy may be applied by any one of the well known means for applying thermal energy such as modalities such as resistive, IR (infrared), ultrasonic heating, microwave, any one of the numerous "hot pads" that chemically produce an exothermic reaction or in the simplest form a hot compress. In the present embodiment, at least a portion of the heat may be provided by the excess heat generated in the LEDs. Experimentation has revealed that in order to be clinically effective the eyelid should be heated to a temperature of between about 35 degrees Celsius and 47 degrees Celsius. The length of time for which thermal energy, i.e., heat is applied to the eyelid depends upon the extent that the obstruction blocks the meibomian gland channel as well as the composition of the obstruction. In very minor cases, heat may be applied to the eyelid for less than three minutes or even as little as five to fifteen seconds. On the other hand, extreme blockage may require as much as thirty minutes of heating to soften the obstruction prior to the application of pressure to the eyelid to express the softened obstruction.

Experimentation has further revealed that the eyelids are efficient heat exchangers with circulating blood acting as the cooling mechanism and that the eyelid temperature returns to normal in less than two minutes at which time the obstruction re-hardens making extraction difficult. It is therefore necessary to apply the aforesaid expressive force to the eyelid within that time frame in order for the treatment to be successful. Thus, gentle finger pressure, preferably in a milking type action, to urge the obstruction upward and out of the meibomian gland orifice should be employed. Again, depending on the nature and location of the obstruction, mere compressive force may be effective in some instances.

In a further embodiment, the insulator is inserted between the rear of the eyelid on the surface of the eyeball as previously described. An eyecup 780 is employed to provide pressure to the eyelid. In one embodiment, thermal energy is applied as described above, an eyecup 780 (which may be unheated) is placed on the outer surfaces of the eyelid and pressure is applied thereto to express the softened obstruction. The eyecup mirrors the size and shape of the eyelids when closed.

Eyecup 780 is adapted to overlie the outer surface of the eyelid, substantially conforms to the surface shape thereof and is adapted to cooperate with the lenspiece insulator 724. Eyecup 780 includes a centrally located longitudinal slot which receives the male connector member 728. In certain embodiments, positioned on the underside of the eyecup 780 is a diaphragm arrangement as described in the provisional application and shown as 784. The pair of diaphragms 784 are in fluid communication with each other and include an inlet or inlet. Diaphragms 784 are attached to the eyecup 780 via conventional means such as glue (not shown). It will be noted that the eyecup could be provided with a single diaphragm with a hole defining an opening through male connector member 728 may pass.

Diaphragms 784 may be fabricated from a biocompatible material such as polyurethane foam (open or closed cell), a sealed air balloon, a gel-filled bladder. Again, depending upon the type and degree of obstruction, the diaphragms will vary in thickness and/or durometer. In an alternate embodiment, diaphragms 784 may comprise bladders which may be fabricated from any flexible expandable material such as rubber or plastic, however, it is preferred that the coefficient of expansion be linear with respect to the amount of fluid added. The bladders may be partially filled with a constant amount of fluid or they may be provided with a rudimentary pump connected to inlet 305 such as is used with a perfume aerosolizer. The fluid is preferably air, but may also be a liquid such as water, saline, etc. Further, while not shown, the fluid may also be heated in order to assist in the softening of any meibomian gland obstructions which may be present. It will be noted that for any given patient, the either or both of the insulator and fluid may be heated as required in order to soften any given obstructed meibomian glands. While not illustrated, the bladders could be fabricated in such a manner that as they inflate pressure is applied which urges the softened gland obstructive material up the gland channel and out of the gland orifice to clear the gland. One method would be to increase the thickness of the bladders such that there is less resistance (less thickness) to inflation near the bottom of the gland and the resistance increases (greater thickness) as one reaches the gland orifice.

In operation, the lenspiece insulator 724 is placed on the sclera of the eye in much the same manner as a contact lens is inserted. The eyecup 780 and bladder 784 are then positioned with the concavity facing the eyelid. The connector 734 is then used to couple lenspiece 724 to the eyecup 780. Heat is then activated by a switch or control processor 692 or other means to which the heated fluid in the bladders 784 may be added simultaneously or serially for the preselected period of time, for example, two minutes. Thereafter, or simultaneously with the application of heat the bladders 784 may be expanded which will urge the softened meibomian gland sebum up and out of the gland channel towards the gland orifice, thus, unblocking the gland. When treatment is complete, the connector 734 is disengaged and the lenspiece 724 and bladders 784 are removed. The assembly 684 can then be readily removed from the eyeball and treatment is complete.

It will be noted that various mechanisms to lock the insulator to the eyecup could be employed such as a ratchet type mechanism, a press fit as well as other mechanisms well known to those skilled in the art, not discussed herein. While not specifically required, it is preferable that the locking mechanisms be near "zero insertion" force in order to minimize the potential for eye injury.

Figure 37:
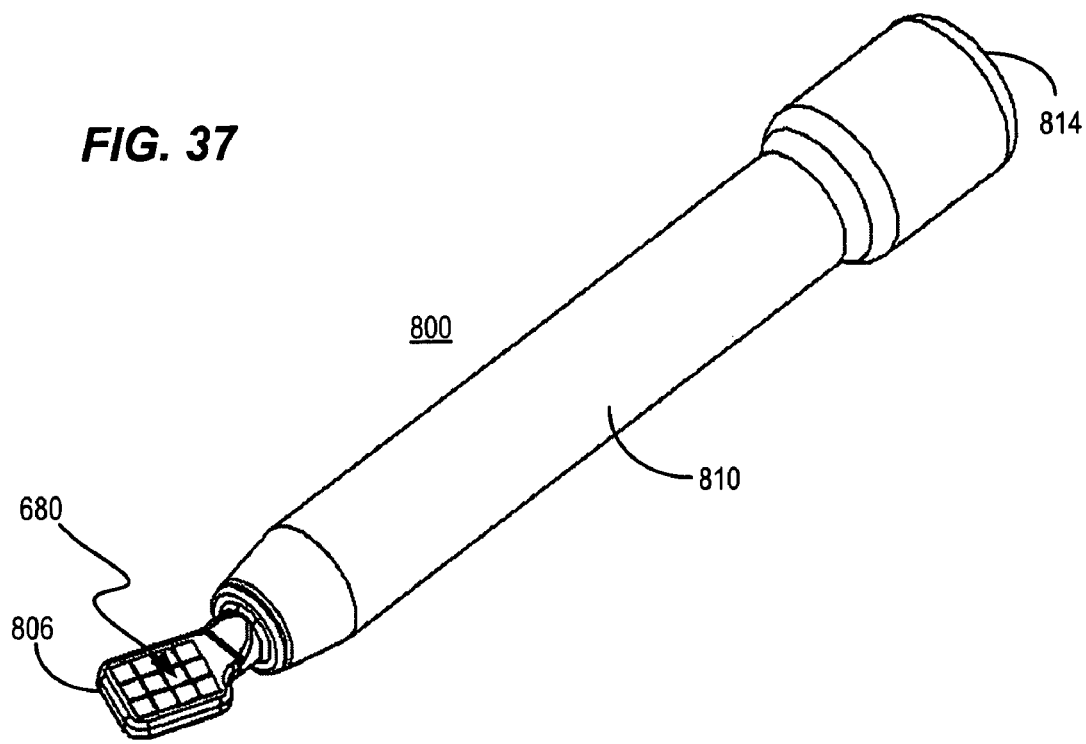
FIG. 37 depicts a hand held trans-illumination device consistent with certain embodiments of the present invention.

Yet a further embodiment of a tool for use in trans-illumination of the eyelid is depicted in FIG. 37. In this embodiment, the device 800 is manually manipulated by a physician, technician, etc. to provide illumination to an isolated portion of the eyelid. In this embodiment, a small paddle-like eye shield 806 provides a surface for mounting of the LEDs in LED array. The eye shield is opaque to permit light to shine only toward the inner surface of the eyelid while shielding the eye from the bright light. The paddle-like eye shield is mounted to the end of a handle 810 that serves as a battery holder that can hold several batteries used to power the LEDs, in which case an end cap 814 may be removed to access the batteries in the manner of a flashlight, or may serve to couple externally supplied power to the LEDs.

In use, the eyelid is lifted away from the eyeball and the paddle is inserted between the eyelid and the eyeball pulling the eyelid outward to trans-illuminate a portion of the eyelid. Additionally, the paddle-like eye shield can be used as a surface against which to apply pressure through the eyelid to express fluid from the meibomian glands or abnormal structures of the eye such as a stye, pimple, chalazion and hordeolum or other abnormalities that can be treated by heat, pressure, light or release of trapped fluids. This pressure can be applied using the tool depicted in FIGS. 13-21 or by use of a finger or other tool.

Once trans-illuminated, by any of the methods depicted, the meibomian glands or other eyelid structures can be visualized or imaged using any of the arrangements previously described. Any motion artifacts should be considered in evaluation of the images, or processed out of the images.

As described above, NIR imaging can be carried out by use of trans-illumination techniques as described above. This technique can be carried out by use of a light source placed behind the eyelid. In the embodiment described above, this light source takes the form of a scleral lens 640 that receives light from a source, such as a NIR light source, and directs light outward through the eyelid to facilitate visual or photographic observation of the condition of the meibomian glands. This observation can be made by either microscopy or microscopic photography.

U.S. Provisional patent application No. 60/880,850 filed Jan. 17, 2007 describes a device that uses a heated lenspiece (i.e., a device resembling a scleral lens in that it is placed in contact with the eyeball between the eyeball and the eyelid) which is placed behind the eyelid and is used for treatment of the eyelids for MGD. In another embodiment, this device can be adapted to use a similarly configured lenspiece, but replaces the heater element with a light source to enable trans-illumination of the eyelid while the eyelid remains in its normal position. This light source can be designed to provide illumination using visible light, IR light, NIR light, UV light or any combination thereof that is found suitable for visualization of the MG structures or other features of the eyelid.

In order to provide manual trans-illumination to visualize the vessels and glands within the eyelid, a great deal of skill and dexterity is normally required on the part of the physician. In the conventional technique, the eyelid is manipulated around the light source to provide lighting from the outer surface of the eyelid (which is inverted) and observed from the inner surface. This generally requires two hands. The first hand holds the light source in place on the outside of the eyelid while the second hand pulls the eyelid over the light source and bends it into a position where the desired areas can be visualized using a slit lamp microscope or photographically imaged. The technique is difficult to administer and due to its very nature will not allow the physician to visualize the vessels and glands in their normal anatomical state due to the manipulation required to invert and bend the eyelid over the light source. Use of any of the devices such as depicted in FIG. 30, or 32-25 or 37, the disclosed device solves the "ease of use" problem and will allow the glands to be visualized in their nearly normal anatomical state. The physician's hands are free to adjust the slit lamp magnification and/or perform any desired lid manipulation. Additionally, the light source illuminates the entire upper and lower eyelid simultaneously.

Since the light source is placed on the back of the eyelid and aimed outward, the chance of accidental exposure of the eye to any harmful light source is minimized. The light source can be tuned to different frequencies which would more readily be transmitted or absorbed into the tissue. The light source can also be tuned to provide some heating to the eyelid as well as providing the trans-illumination function. By providing such heating, the therapeutic effects of the device can be carried out while simultaneously providing the ability to observe the MGs. Moreover, if the heating is appropriately tuned, to provide enough heating power, a single lenspiece could be used to replace the heated lenspiece portion of the device depicted in the provisional application. The particular light source being used can be tuned to balance the amount of light provided by adjustment of absorption and penetration properties of the device to strike a desired balance between providing illumination and providing heating.

Research has been conducted on photothermolysis where it has been shown that certain light wavelengths absorb more in lipid rich material. This implies that selection a wavelength could allow the illuminated lenspiece to provide a level of heating to lipid-rich meibomian glands while providing a reduced level of heat to the surrounding tissue. This would in turn cause the glands to appear darker while trans-illuminating thereby visually tagging lipid rich areas and thus facilitating visualization. Additional research and experimentation can be conducted to verify this benefit in MGD treatment and visualization, however, it is noted that U.S. Pat. No. 7,060,061 to Altshuler et al. indicates that lipid rich material has a preferential absorption wavelength of light.

In the exemplary embodiments depicted, the light source depicted can be embodied as an array of Light Emitting Diodes (LEDs) components mounted on a flexible circuit or a series of light pipes. By illuminating the eyelid from the inside surface the physician will be able to use his standard slit lamp microscope to visualize the Tran illuminated tissue without manipulating the eyelid.

By replacing the heater assembly shown in the provisional application with a series of LEDs the lenspiece serves as a light source. The lenspiece, once placed on the eye, will illuminate the eyelid. The physician, technician, etc. can visualize the light as it passes through the eyelid by use of a slit lamp microscope or can capture images as described above using a suitable camera arrangement. The resulting image will show darker areas where light is absorbed more than other areas. The present device therefore provides a hands free method and allowing the physician to view the glands while they are oriented in their normal anatomical position.

Certain wavelengths of light, as noted above, appear to be more preferentially absorbed by lipid rich material. The field of selective photothermolysis has performed studies in this area that indicate that the wavelengths of 880 nm to 935 nm; 1160 nm to 1230 nm; 1690 nm to 1780 nm; and 2250 nm to 2450 nm may have higher absorption in lipid than the surrounding tissue. Hence, use of light in these wavelengths would likely assist in providing a visual tag on the lipids by making the area of lipid rich material appear darker than the tissue areas surrounding it. Alternatively, it appears likely that there are particular wavelengths of light that is more likely to preferentially pass light through lipid rich material while preferentially being absorbed in the surrounding tissue. A wavelength with that particular characteristic would show the glands a being lighter than the surrounding tissue. Again, experimentation with various light sources can be done to identify a light wavelength range that provides enhancement of contrast between the MGs and surrounding. Additionally, such contrast may be enhanced by using a broader spectrum of light and filtering the light to enhance the contrast.

If a light wavelength is selected which absorbs into tissue then heating will result. Infra red wavelengths have such properties and would be an alternative to a resistively heated lenspiece. The infrared light penetrates the eyelid and heat will be generated as it is passes through. A temperature sensor placed at or near the inner eyelid and another sensor placed at or near the outer eyelid can be used to regulate the temperature in much the same manner as that disclosed in the above-referenced provisional application. The portion of electrical energy which does not convert to light will be translated into heat much the same as the existing heating element. Therefore, not only will the LED assembly provide a penetrating heat source, it will also provide a contact heat source with the added benefit of illuminating the eyelids.

The illumination effect will enable the ophthalmologist, optometrist, technician, etc., to view the vessels and glands within the eyelid under the magnification of their slit lamp microscopes. The trans-illumination process will potentially enable visualization of the glands before use of the device depicted in the provisional application procedure or other therapeutic procedure and after the procedure without needed any additional specialized equipment. The LED lenspiece is simply placed onto the patients eye, then the lenspiece is provided with power and a simple slit lamp microscopic examination of the eyelid will provide a "before" look at the eyelid vessels and glands. The eyecup portion is then attached to the device depicted in the provisional application and performs the procedure using the illuminated lens to provide the therapeutic heat. Once finished they simply remove the eyecup while leaving the lens in place and use the trans-illumination effect of the lens to perform an "after" examination of the eyelid vessels and glands.

Thus, in one embodiment consistent with the present invention, a method of imaging a mammalian meibomian gland or other section of an eyelid involves shining a light on the outer surface of the eyelid in order to trans-illuminate a portion of the eyelid with oblique illumination; and from the outer surface of the eyelid, capturing an image of trans-illuminated portion of the eyelid.

In certain embodiments, the captured image is stored in an electronic storage medium and/or displayed on a video display. In certain embodiments, the shining and capturing are repeated at an adjacent location of the outer surface of the eyelid. In certain embodiments, the images from the first and adjacent locations are combined. In certain embodiments, the combining includes stitching, adding, or averaging the images from the first and adjacent locations to produce a resultant image of a larger area of the eyelid. In certain embodiments, the light includes infrared light radiation and capturing the image is carried out using infrared photography. In certain embodiments, the light includes visible light radiation and capturing the image is carried out using visible light photography. In certain embodiments, a computer readable storage medium can store instructions which, when executed on a programmed processor, carry out these methods.

In another embodiment, a method of imaging a mammalian patient's meibomian gland or other section of an eyelid of an eye involves placing a contact lens in contact with the eye; having the patient close the eye; illuminating the contact lens to generate light emitting from the lens through the eyelid from the posterior surface of the eyelid; and from the outer surface of the eyelid, capturing an image of a trans-illuminated portion of the eyelid. In certain embodiments, the captured image is stored in an electronic storage medium and/or displayed on a video display or otherwise rendered. In certain embodiments, the method further involves repeating the illumination and capturing of an image at a second location on the eyelid, and processing the images to produce a single composite image. In certain embodiments, the light includes infrared light radiation and capturing the image is carried out using infrared photography. In certain embodiments, the light includes visible light radiation and capturing the image is carried out using visible light photography. In certain embodiments, a computer readable storage medium can store instructions which, when executed on a programmed processor, carry out these methods.

In another embodiment, a method of imaging a mammalian meibomian gland or other section of an eyelid involves placing a light source at a first position adjacent an outer surface of the eyelid in order to trans-illuminate a portion of the eyelid from an outer surface thereof; from the outer surface of the eyelid, capturing a first image of trans-illuminated portion of the eyelid, the first image containing at least a portion of the light source; repositioning the light source to a second position adjacent an outer surface of the eyelid in order to trans-illuminate a portion of the eyelid from an outer surface thereof; from the outer surface of the eyelid, capturing a second image of trans-illuminated portion of the eyelid, the second image containing at least a portion of the light source; and computing a composite of the first and second image to produce a resulting image.

In certain embodiments, a computer readable storage medium can store instructions which, when executed on a programmed processor, carry out these methods. In certain embodiments, the computing of the composite image is carried out by a process of averaging, stitching or adding the first and second images. In certain embodiments, a composite image is computed by subtracting a light source obstruction from the image. In certain embodiments, the resulting image is stored in an electronic storage medium and/or displayed on a video display or otherwise rendered. In certain embodiments, the light source includes an infrared light radiation source and capturing the images is carried out using infrared photography. In certain embodiments, the light source includes a visible light radiation source and capturing the images is carried out using visible light photography.

In another embodiment consistent with the present invention an apparatus for imaging a portion of a mammalian eyelid has a light source suitable for directing light to a portion of the outer surface of the eyelid using oblique illumination in order to trans-illuminate the portion of the eyelid. An optical receiver is provided that is suitable for receiving light transmitted through a portion of the eyelid and producing an output signal related to characteristics of the trans-illuminated portion of the eyelid, the light receiver receiving light from the outer surface of the eyelid. An image processor receives the output signal and captures an image from the light receiver.

In certain embodiments, an electronic storage device stores the captured image. In certain embodiments, a display displays the captured image. In certain embodiments, the light source directs light to the portion of the outer surface of the eyelid via a first optical fiber. In certain embodiments, the optical receiver receives light from the outer surface of the eyelid via a second optical fiber. In certain embodiments, the light source directs light to the portion of the outer surface of the eyelid via a first optical fiber, and the optical receiver receives light from the outer surface of the eyelid via a second optical fiber, and the first and second optical fibers are positioned in a fixed geometric relationship with one another. In certain embodiments, the first and second optical fibers are positioned to direct light at a specified angle and receive the light at the specified angle as measured from a plane approximation of the surface of the eyelid. In certain embodiments, the first and second optical fibers are commonly contained in a single handpiece that holds the first and second optical fibers in the fixed geometric relationship with one another. In certain embodiments, multiple adjacent locations of the outer surface of the eyelid are imaged. In certain embodiments, a processor combines the images from the multiple adjacent locations. In certain embodiments, a processor stitches the images from the multiple adjacent locations to produce a resultant image of a larger area of the eyelid. In certain embodiments, a processor sums the images from the multiple adjacent locations. In certain embodiments, the light source comprises an infrared light source and wherein the optical receiver is compatible with infrared light. In certain embodiments, the light source comprises a visible light source and wherein the optical receiver is compatible with visible light.

In another embodiment, an apparatus for imaging a portion of a mammalian eyelid has a light source. A contact lens is configured to receive light from the light source and direct the light through an eyelid from posterior to anterior surface to thereby trans-illuminate the eyelid, when the light source illuminates the contact lens, a camera records an image of the eyelid as it is trans-illuminated. In certain embodiments, an image processor, receives an output signal from the camera and processes the output signal to enhance the image. In certain embodiments, an electronic storage device stores the captured image. In certain embodiments, a display displays the captured image. In certain embodiments, the light source includes an infrared light source and wherein the camera is compatible with infrared light. In certain embodiments, the light source includes a visible light source and wherein the camera is compatible with visible light.

In another embodiment, an apparatus for imaging a portion of a mammalian eyelid has a light source configured to direct light through an eyelid from an anterior surface to thereby trans-illuminate the eyelid. A camera records an image of the eyelid as it is trans-illuminated. A positioning mechanism automatically positions the light source at a plurality of locations adjacent the eyelid and record a plurality of images at each of said plurality of locations using the camera. A processor averages the plurality of images to produce a resultant image.

In certain embodiments, an electronic storage device stores the resultant image. In certain embodiments, a display displays the resultant image. In certain embodiments, the light source comprises an infrared light source and wherein the camera is compatible with infrared light. In certain embodiments, the light source includes a visible light source and wherein the camera is compatible with visible light.

Figure 38:
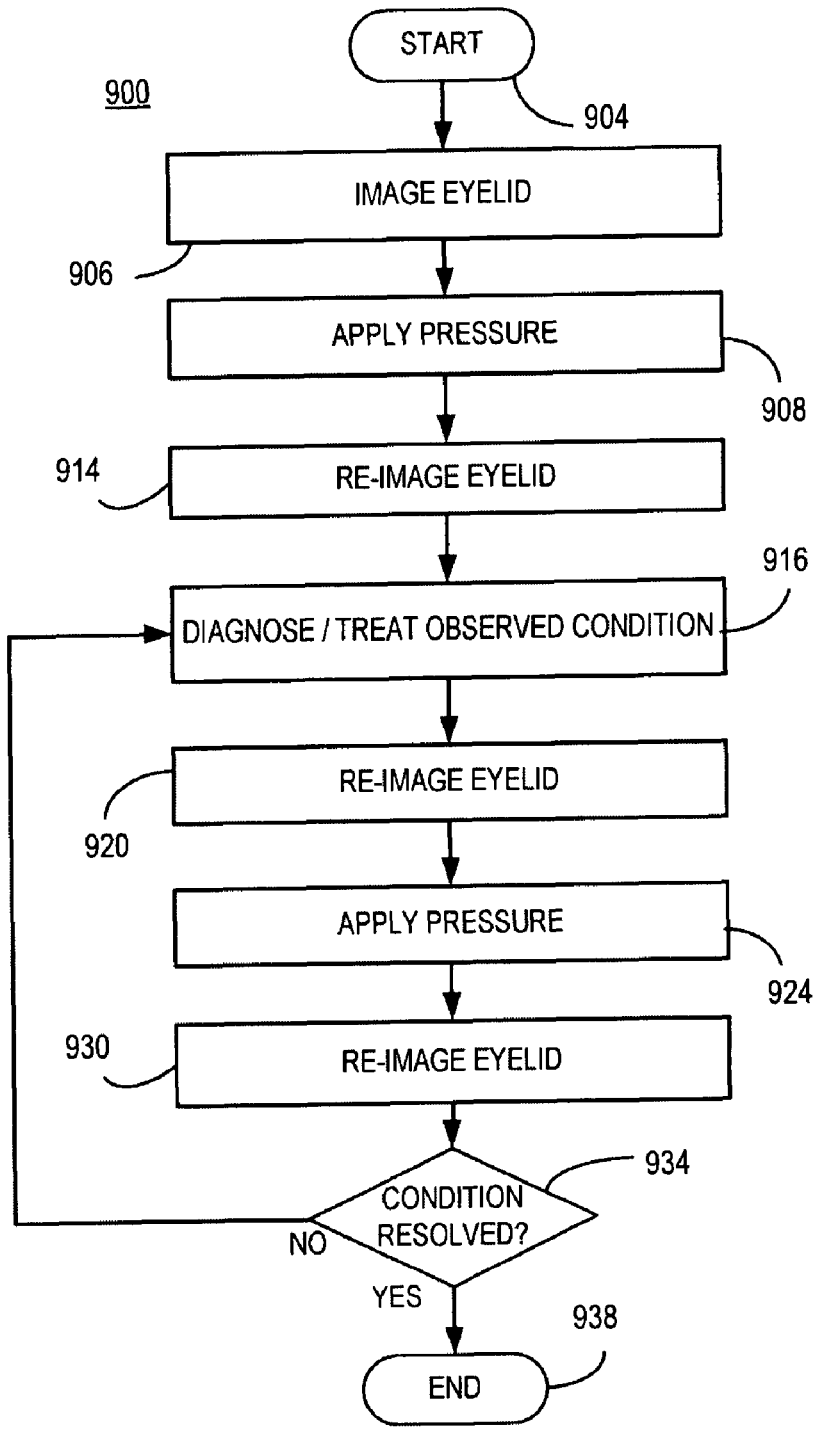
FIG. 38 is a flow chart depicting a method of use for the visualization techniques consistent with embodiments of the present invention.

FIG. 38 depicts an exemplary comprehensive imaging and treatment process 900 that can be used for diagnosis and treatment of MGD using any of the imaging techniques disclosed herein starting at 904. At 906, the eyelid is imaged without any application of force to the eyelid itself. Process 906 may not be possible since the contact with the eyelid by the imaging device may meet or exceed the pressure of blinking. At 908, pressure is applied to the eyelid and the eyelid is re-imaged at 914 while the pressure is present. Once the imaging is completed, a diagnosis can be made and an appropriate course of treatment can be carried out in an effort to resolve the condition observed. The effectiveness of the treatment can then be evaluated by re-imaging the eyelid at 920 without pressure, as well as applying pressure at 924 and re-imaging the eyelid under pressure at 930. A determination can then be quantitatively made at 934 as to the effectiveness of the treatment and either the process can end at 938 or further diagnosis and treatment carried out at 916. It is noted that for ultrasound imaging, processes 908 and 920 may not be possible since the contact with the eyelid may meet or exceed the pressure of blinking. However, the application of pressure in this application may permit imaging of the MG while in the act of secreting when the gland is at least partially properly functioning and not fully occluded. Many variations are possible including only imaging with or without pressure applied to the eyelid at any stage according to the preferences of the physician, experiences with the patient, imaging technique used or other factors.

In order to use any of the above embodiments of imaging techniques and apparatus, it is possible (likely in many instances) that the patient will be more comfortable and thus the imaging process can proceed easier if a topical anesthetic is applied to the outer surfaces of the eyes and to the eyelids. This facilitates greater comfort when the images are created and while the eyelids are manipulated where such manipulation is needed. Moreover, such anesthetic may be beneficial in minimizing patient blinking.

Those skilled in the art will appreciate, upon consideration of the present teachings, that any of the above techniques described can be used to provide reference, pre-treatment and post treatment images of one or more meibomian glands or the eyelid so as to provide diagnosis and records of treatment success.

Those skilled in the art will recognize, upon consideration of the above teachings, that certain of the above exemplary embodiments are based upon use of a programmed processor. However, the invention is not limited to such exemplary embodiments, since other embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Certain embodiments described herein, are or may be implemented using a programmed processor of any suitable design including general purpose, RISC, special purpose and other programmable processor types executing programming instructions that are broadly described above in flow chart form that can be stored on any suitable electronic or computer readable storage medium and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention. Such variations are contemplated and considered equivalent.

Software and/or firmware embodiments may be implemented using a programmed processor executing programming instructions that in certain instances are broadly described above in flow chart form that can be stored on any suitable electronic or computer readable storage medium (such as, for example, disc storage, Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies) and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention. Such variations are contemplated and considered equivalent.

Ranges provided, for magnification and light wavelengths for example, are to be interpreted to include all possible sub-ranges within the disclosed ranges.

While certain illustrative embodiments have been described, it is evident that many alternatives, modifications, permutations and variations will become apparent to those skilled in the art in light of the foregoing description.

What is claimed is:

1. A method of near infrared (NIR) imaging of a meibomian gland, comprising:
   illuminating the meibomian gland with NIR radiation using an NIR light source;
   focusing an NIR camera on a region of an eyelid containing the meibomian gland;
   making a first NIR image of the meibomian gland;
   applying a pressure suitable for simulating blinking pressure on the meibomian gland;
   optionally refocusing the NIR camera on the region of the eyelid containing the meibomian gland; and
   making a second NIR image of the meibomian gland while the pressure is being applied,
   wherein at least one of making the first NIR image and making the second NIR image comprises imaging at least a portion of a meibomian gland channel of the meibomian gland below a meibomian gland orifice of the meibomian gland to allow visualization of a flow or lack of flow of secretory material from within the meibomian gland channel and through the meibomian gland channel toward the meibomian gland orifice.

2. The method according to claim 1, wherein the NIR camera has an objective lens magnification of between about 60× and 10× at between about 650 and 900 nm wavelength.

3. The method according to claim 1, wherein the NIR imaging is carried out using NIR optical imaging in approximately the 0.650 to 2.5 micron wavelength range.

4. The method according to claim 1, wherein the NIR imaging is carried out using trans-illumination photography.

5. The method according to claim 4, wherein trans-illumination is produced by oblique illumination of the eyelid from an anterior surface thereof.

6. The method according to claim 5, wherein the trans-illumination is produced by lighting the eyelid from a posterior surface thereof.

7. The method according to claim 6, wherein the trans-illumination is produced by use of a scleral lens serving as a light source from the posterior surface of the eyelid.

8. The method according to claim 6, wherein the trans-illuminating is carried out using a lenspiece comprising an array of light emitting elements mounted to a substrate suitable for contact with an eyeball.

9. The method according to claim 1, wherein the NIR radiation includes radiation having wavelength that is either absorbed or transmitted preferentially through lipid rich material versus tissue surrounding lipid rich tissue.

10. The method according to claim 1, wherein the step of making a first NIR image is performed while pressure is applied to the eyelid that simulates an amount of pressure caused by blinking the eyelid.

11. A method of imaging a mammalian meibomian gland or other section of an eyelid, comprising:
    shining a near infrared (NIR) light on the eyelid in order to trans-illuminate at least a portion of the eyelid with NIR illumination; and
    from an outer surface of the eyelid, imaging the trans-illuminated portion of the eyelid using NIR microscopic imaging,
    wherein imaging the trans-illuminated portion of the eyelid comprises imaging at least a portion of a meibomian gland channel of the meibomian gland below a meibomian gland orifice of the meibomian gland to allow visualization of a flow or lack of flow of secretory material from within the meibomian gland channel and through the meibomian gland channel toward the meibomian gland orifice.

12. The method according to claim 11, wherein the shining and imaging are repeated at an adjacent location of the outer surface of the eyelid and further comprising combining the images from a first location and the adjacent location.

13. The method according to claim 12, wherein the combining is selected from the group consisting of stitching, adding, and averaging the images from the first and adjacent locations to produce a resultant image of a larger area of the eyelid.

14. The method according to claim 11, wherein the NIR microscopic imaging is carried out using a camera having an objective lens magnification of between about 60× and 10× at between about 650 and 900 nm wavelength.

15. The method according to claim 11, wherein the imaging is carried out using NIR optical imaging in approximately the 0.650 to 2.5 micron wavelength.

16. The method according to claim 11, wherein trans-illumination is produced by lighting the eyelid from a posterior surface thereof.

17. The method according to claim 16, wherein the trans-illumination is produced by use of a scleral lens serving as a light source from the posterior surface of the eyelid.

18. The method according to claim 16, wherein the trans-illumination is produced by use of a contact lenspiece comprising an array of light emitting elements mounted to a substrate suitable for contact with an eyeball.

19. The method according to claim 11, further comprising providing NIR radiation to the eyelid, wherein the NIR radiation includes radiation having wavelength that is either absorbed or transmitted preferentially through lipid rich material versus tissue surrounding lipid rich tissue.

20. A method of imaging a mammalian patient's meibomian gland or other section of a closed eyelid of an eye, comprising:
    placing a contact light source in contact with the closed eyelid;
    illuminating the contact light source such that light emitting from the contact light source through the closed eyelid from a posterior surface of the eyelid trans-illuminates a portion of the closed eyelid; and
    from an outer surface of the closed eyelid, imaging the trans-illuminated portion of the closed eyelid,
    wherein imaging the trans-illuminated portion of the closed eyelid comprises imaging at least a portion of a meibomian gland channel of the meibomian gland below a meibomian gland orifice of the meibomian gland to allow visualization of a flow or lack of flow of secretory material from within the meibomian gland channel and through the meibomian gland channel toward the meibomian gland orifice.

21. The method according to claim 20, further comprising repeating the illumination and capturing of an image at a second location on the eyelid, and processing the images to produce a single composite image.

22. The method according to claim 20, wherein the contact light source produces NIR light and wherein imaging is carried out using a NIR camera having an objective lens magnification of between about 60× and 10× at between about 650 and 900 nm wavelength.

23. The method according to claim 22, wherein the imaging is carried out using NIR optical imaging in approximately the 0.650 to 2.5 micron wavelength.

24. The method according to claim 20, wherein the trans-illumination is produced by lighting the eyelid from the posterior surface thereof.

25. The method according to claim 20, wherein the trans-illumination is produced by use of a scleral lens serving as a light source from the posterior surface of the eyelid.

26. The method according to claim 24, wherein the trans-illumination is produced by a contact lenspiece that comprises an array of light emitting elements mounted to a substrate suitable for contact with an eyeball.

27. The method according to claim 20, further comprising providing NIR radiation to the eyelid, wherein the NIR radiation includes radiation having wavelength that is either absorbed or transmitted preferentially through lipid rich material versus tissue surrounding lipid rich tissue.

28. An apparatus for imaging a portion of a mammalian eyelid, comprising in combination:
a light source suitable for directing near infrared (NIR) light to a portion of the eyelid to illuminate a portion of the eyelid;
a microscopic optical receiver suitable for receiving light reflected from the eyelid and producing an output signal depicting an NIR image of the eyelid, the microscopic optical receiver receiving light reflected from an outer surface of the eyelid; and
an image processor, receiving the output signal, that captures the NIR image from the microscopic optical receiver,
wherein the NIR image captured by the image processor comprises an image of at least a portion of a meibomian gland channel of a meibomian gland in the eyelid below a meibomian gland orifice of the meibomian gland to allow visualization of a flow or lack of flow of secretory material from within the meibomian gland channel and through the meibomian gland channel toward the meibomian gland orifice.

29. The apparatus according to claim 28, wherein the light source is arranged to provide oblique illumination in order to trans-illuminate the portion of the eyelid.

30. The apparatus according to claim 28, wherein the light source directs light to the portion of the outer surface of the eyelid via a first optical fiber.

31. The apparatus according to claim 30, wherein the microscopic optical receiver receives light from the outer surface of the eyelid via a second optical fiber.

32. The apparatus according to claim 28, wherein trans-illumination is produced by lighting the eyelid from a posterior surface thereof.

33. The apparatus according to claim 28, wherein the light source comprises a scleral lens serving as a light source from the posterior surface of the eyelid.

34. The apparatus according to claim 28, wherein the light source produces light having wavelength that is either absorbed or transmitted preferentially through lipid rich material versus tissue surrounding lipid rich tissue.

35. The apparatus according to claim 28, wherein the light source comprises a lenspiece having an array of light emitting elements mounted to a substrate suitable for contact with an eyeball.

36. The apparatus according to claim 28, wherein the light source directs light to the portion of the outer surface of the eyelid via a first optical fiber, and wherein the microscopic optical receiver receives light from the outer surface of the eyelid via a second optical fiber, and wherein the first and second optical fibers are positioned in a fixed geometric relationship with one another.

37. An apparatus for imaging a portion of a mammalian eyelid, comprising in combination:
an eye contact lenspiece configured to direct light from a light source through an eyelid from posterior to anterior surface to thereby trans-illuminate the eyelid, wherein light from the light source illuminates the eye contact lenspiece; and
an imaging device that captures an image of the eyelid as it is trans-illuminated,
wherein the NIR image captured by the imaging device comprises an image of at least a portion of a meibomian gland channel of a meibomian gland in the eyelid below a meibomian gland orifice of the meibomian gland to allow visualization of a flow or lack of flow of secretory material from within the meibomian gland channel and through the meibomian gland channel toward the meibomian gland orifice.

38. The apparatus according to claim 37, further comprising an image processor, receiving an output signal from the imaging device and processes the output signal to enhance the image.

39. The apparatus according to claim 37, wherein the light source comprises an infrared light source and wherein the imaging device is compatible with infrared light.

40. The apparatus according to claim 37, wherein the light source comprises a visible light source and wherein the imaging device is compatible with visible light.

41. The apparatus according to claim 37, wherein trans-illumination is produced by lighting the eyelid from a posterior surface thereof.

42. The apparatus according to claim 37, wherein the light source comprises a scleral lens serving as a light source from the posterior surface of the eyelid.

43. The apparatus according to claim 37, wherein the light source produces light having wavelength that is either absorbed or transmitted preferentially through lipid rich material versus tissue surrounding lipid rich tissue.

44. The apparatus according to claim 37, wherein the light source comprises a lenspiece having an array of light emitting elements mounted to a substrate suitable for contact with an eyeball.

45. An apparatus for imaging a portion of a mammalian eyelid, comprising in combination:
a light source configured to direct near infrared (NIR) light through an eyelid to thereby trans-illuminate the eyelid;
a NIR microscopic camera that records an image of the eyelid as it is trans-illuminated;
means for automatically positioning the light source at a plurality of locations adjacent the eyelid and record a plurality of images at each of said plurality of locations using the NIR microscopic camera; and a processor that averages the plurality of images to produce a resultant image, wherein at least one of the plurality of the recorded images comprises an image of at least a portion of a meibomian gland channel of a meibomian gland in the eyelid below a meibomian gland orifice of the meibomian gland to allow visualization of a flow or lack of flow of secretory material from within the meibomian gland channel and through the meibomian gland channel toward the meibomian gland orifice.

46. The apparatus according to claim 45, wherein the NIR microscopic camera has an objective lens magnification of between about 60× and 10× at between about 650 and 900 nm wavelength.

47. The method according to claim 46, wherein the imaging is carried out using NIR optical imaging in approximately the 0.650 to 2.5 micron wavelength.

48. The apparatus according to claim 45, wherein transillumination is produced by lighting the eyelid from a posterior surface thereof.

49. The apparatus according to claim 45, wherein the light source comprises a scleral lens serving as a light source from the posterior surface of the eyelid.

50. The apparatus according to claim 45, wherein the light source comprises a lenspiece having an array of light emitting elements mounted to a substrate suitable for contact with an eyeball.

51. The apparatus according to claim 45, wherein the light source produces light having wavelength that is either absorbed or transmitted preferentially through lipid rich material versus tissue surrounding lipid rich tissue.

* * * * *